US006559152B2

(12) United States Patent
Markwalder et al.

(10) Patent No.: US 6,559,152 B2
(45) Date of Patent: *May 6, 2003

(54) 6-SUBSTITUTED PYRAZOLO[3,4-D] PYRIMIDIN-4-ONES USEFUL AS CYCLIN DEPENDENT KINASE INHIBITORS

(75) Inventors: Jay A. Markwalder, London University, PA (US); Steven P. Seitz, Swarthmore, PA (US); Susan R. Sherk, Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/794,825

(22) Filed: Feb. 27, 2001

(65) Prior Publication Data

US 2002/0013328 A1 Jan. 31, 2002

Related U.S. Application Data

(63) Continuation-in-part of application No. 09/416,584, filed on Oct. 12, 1999.
(60) Provisional application No. 60/103,957, filed on Oct. 13, 1998.
(51) Int. Cl.[7] ...................... A61K 31/519; A61K 31/44; C07D 487/00; C07D 237/26; C07D 471/02
(52) U.S. Cl. .................. 514/262.1; 514/253; 514/303; 544/235; 544/262; 546/119; 546/120
(58) Field of Search ................................ 546/119, 120; 544/262, 238; 514/262.1, 303, 253

(56) References Cited

U.S. PATENT DOCUMENTS 3,211,731 A * 10/1965 Schmidt et al. .......... 260/256.4
3,211,732 A 10/1965 Schmidt et al.
5,593,997 A 1/1997 Dow et al.

FOREIGN PATENT DOCUMENTS

| EP | 0773023 | 5/1997 |
| WO | WO94/13677 | 6/1994 |
| WO | 9805335 | 2/1998 |
| WO | WO00/21926 | 4/2000 |

OTHER PUBLICATIONS

Shaw, Gordon et al., Chemical Abstracts, 1971, 75, No. 1, Abstract No. 5837.
Paveltich, Nature 382:325–331, 1996.
Kamb et al, Science 264: 436–440, 1994.
Sherr, Cell 73:1059–1065, 1993.
Jiang, Proc. Natl. Acad. Sci. USA 90:9026–9030, 1993.
Beach, Nature 336:701–704, 1993.
Wang, Nature 343:555–557, 1990.
Draetta, Trends Biochem. Sco, 15:378–382, 1990.
Paradee, Science 246:603–608, 1989.
Miyashit a et al., Heterocycles, vol. 31, No. 7, 1309–1314, 1990.
Senga et al., Journal of Heterocyclic Chemistry, vol. 19, No. 6, 1565–1567, Nov.–Dec. 1982.
Reddy et al., Chemical Abstract No. 174107u, vol. 116, 860, Apr. 1992.

* cited by examiner

Primary Examiner—Mukund J. Shah
Assistant Examiner—Tamthom N. Truong
(74) Attorney, Agent, or Firm—Rena Patel

(57) ABSTRACT

The present invention relates to the synthesis of a novel class of pyrazolo[3,4-d]pyrimidin-4-ones of formula (I), alternatively represented by the tautomer (II):

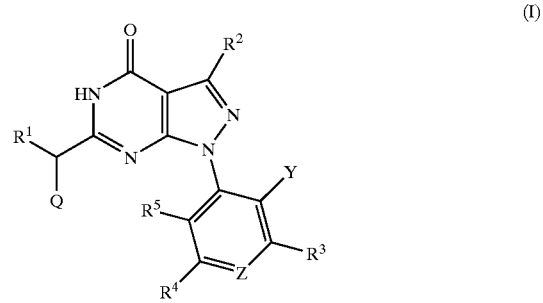

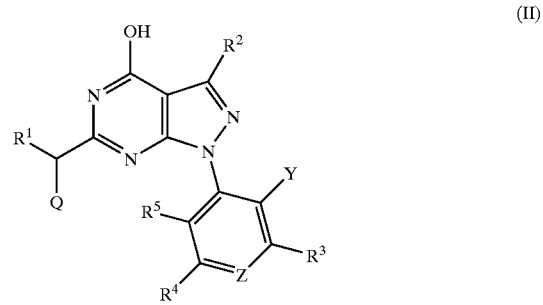

that are potent inhibitors of the class of enzymes known as cyclin dependent kinases, which relate to the catalytic subunits cyclin dependent kinase 1–8 and their regulatory subunits know as cyclins A–H, K, N, and T.

This invention also provides a novel method of treating cancer or other proliferative diseases by administering a therapeutically effective amount of one of these compounds or a pharmaceutically acceptable salt form thereof. Alternatively, one can treat cancer or other proliferative diseases by administering a therapeutically effective combination of one of the compounds of the present invention and one or more other known anti-cancer or anti-proliferative agents.

8 Claims, No Drawings

6-SUBSTITUTED PYRAZOLO[3,4-D] PYRIMIDIN-4-ONES USEFUL AS CYCLIN DEPENDENT KINASE INHIBITORS

RELATED APPLICATIONS

This is a continuation-in-part application of Ser. No. 09/416,584, filed Oct. 12, 1999, in the name of Markwalder et al. the disclosure of which is herein incorpoarted by reference as though set forth in full.

FIELD OF THE INVENTION

This invention relates to 6-substituted pyrazolo[3,4-d] pyrimidin-4-ones useful as cyclin dependent kinase (cdk) inhibitors, pharmaceutical compositions comprising the same, methods for using these compounds for treating cancer and proliferative diseases, and intermediates and processes for making the same.

BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Overexpression of the tumor promoting components or the subsequent loss of the tumor suppressing products will lead to unregulated cellular proliferation and the generation of tumors (Pardee, Science 246:603–608, 1989).

Cyclin dependent kinases play a key role in regulating the cell cycle machinery. These complexes consist of two components: a catalytic subunit (the kinase) and a regulatory subunit (the cyclin). To date, eight kinase subunits (cyclin dependent kinase 1–8) have been identified along with several regulatory subunits (cyclins A–H, K, N, and T). Each kinase associates with a specific regulatory partner and together make up the active catalytic moiety. Each transition of the cell cycle is regulated by a particular cyclin dependent kinase complex: G1/S by cyclin dependent kinase2/cyclin E, cyclin dependent kinase4/cyclin D1 and cyclin dependent kinase6/cyclinD2; S/G2 by cyclin dependent kinase2/cyclin A and cyclin dependent kinase1/cyclin A; G2/M by cyclin dependent kinase1/cyclinB. The coordinated activity of these kinases guides the individual cells through the replication process and ensures the vitality of each subsequent generation (Sherr, Cell 73:1059–1065, 1993; Draetta, Trends Biochem. Sci. 15:378–382, 1990).

An increasing body of evidence has shown a link between tumor development and cyclin dependent kinase related malfunctions. Over expression of the cyclin regulatory proteins and subsequent kinase hyperactivity have been linked to several types of cancers (Jiang, Proc. Natl. Acad. Sci. USA 90:9026–9030, 1993; Wang, Nature 343:555–557, 1990). More recently, endogenous, highly specific protein inhibitors of cyclin dependent kinases were found to have a major affect on cellular proliferation (Kamb et al., Science 264:436–440, 1994; Beach, Nature 336:701–704, 1993). These inhibitors include p16$^{INK4}$ (an inhibitor of cyclin dependent kinase4/D1), p21$^{CIP1}$ (a general cyclin dependent kinase inhibitor), and p27$^{KIP1}$ (a specific cyclin dependent kinase2/E inhibitor). A recent crystal structure of p27 bound to cyclin dependent kinase2/A revealed how these proteins effectively inhibit the kinase activity through multiple interactions with the cyclin dependent kinase complex (Pavletich, Nature 382:325–331, 1996). These proteins help to regulate the cell cycle through specific interactions with their corresponding cyclin dependent kinase complexes. Cells deficient in these inhibitors are prone to unregulated growth and tumor formation.

Schmidt et al. describe in U.S. Pat. No. 3,211,731 (issued Oct. 12, 1965) pyrazolo[3,4-d]pyrimidines of the formula:

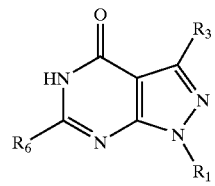

where:

$R_1$ represents hydrogen, alkyl, cycloalkyl, aralkyl, oxalkyl, hydroxyalkyl, halogenoalkyl, cycloalkylalkyl, heteroaralkyl, mono- or binuclear aryl or heteroaryl;

$R_3$ represents hydrogen or lower alkyl;

$R_6$ represents substituted or unsubstituted aralkyl or heteroaralkyl.

These compounds are claimed to have utility as coronary dilating agents. Schmidt et al. disclose as intermediates, in U.S. Pat. No. 3,211,732 (issued Oct. 12, 1965) pyrazolo[3,4-d]pyrimidines within the above scope.

The two references cited above do not describe compounds in which the $R^1$ group is a substituted phenyl or pyridyl.

SUMMARY OF THE INVENTION

The present invention is directed to 6-substituted pyrazolo [3,4-]pyrimidin-4-ones or pharmaceutically acceptable salt or prodrug forms thereof, that are inhibitors of the class of enzymes known as cyclin dependent kinases.

The present invention is also directed to methods of treating cancer or other proliferative diseases by administering a therapeutically effective amount of at least one of the compounds of the present invention or a pharmaceutically acceptable salt or prodrug form thereof to a patient in need of such treatment.

Additionally the present invention is directed to methods of treating cancer or other proliferative diseases, which comprises administering a therapeutically effective combination of at least one of the compounds of the present invention and at least one other known anti-cancer or anti-proliferative agent.

Compounds of the present invention have formula (I), alternatively represented by the tautomer (II):

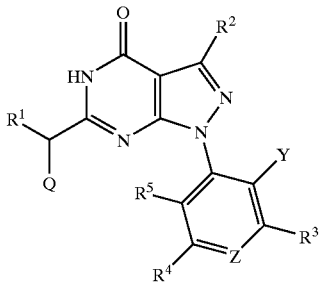

(I)

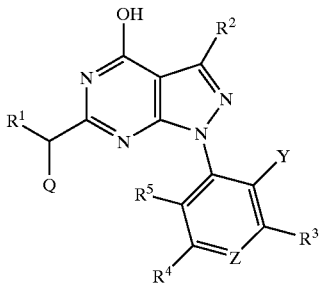

(II)

wherein $R^1$, $R^2$, $R^3$, $R^4$, $R^5$, Q, Y, and Z as defined below or pharmaceutically acceptable salts thereof, are cyclin dependent kinase inhibitors.

As described herein, the inhibitors of this invention are capable of inhibiting the cell-cycle machinery and consequently would be useful in modulating cell-cycle progression, which would ultimately control cell growth and differentiation. Such compounds would be useful for treating subjects having disorders associated with excessive cell proliferation, such as cancer, psoriasis, immunological disorders involving unwanted leukocyte proliferation, in the treatment of restenosis and other smooth muscle cell disorders, and the like.

DETAILED DESCRIPTION OF THE INVENTION

The present invention is directed to a class of compounds of formula (I) or it's tautomer, formula (II):

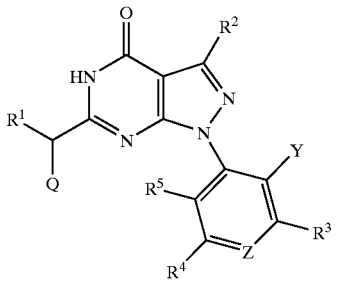

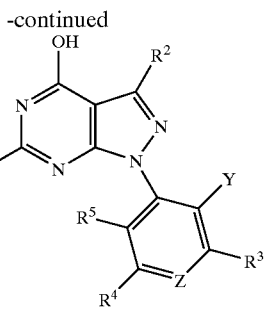

or a stereoisomer or pharmaceutically acceptable salt form thereof, wherein:

Q is selected from the group consisting of: H, OH, and $C_{1-7}$ alkyl;

Y is selected from the group consisting of: F, Cl, Br, and I;

Z is selected from the group consisting of: N, C—H, C—F, C—Cl, C—Br, C—I, C—$CF_3$, C—$NO_2$, C—$C_{1-4}$ alkyl optionally containing from 1–8 substitution groups, C—$C_{2-4}$ alkenyl optionally containing from 1–8 substitution groups, C—$C_{2-4}$ alkynyl optionally containing from 1–8 substitution groups, C—$C_{1-4}$ alkoxy optionally containing from 1–8 substitution groups, C—$CO_2H$, C—CHO, C—$CONR^6R^9$, C—$CO_2C_{1-3}$ alkyl, C—$C(O)C_{1-2}$ alkyl, C—$CH_2NHR^6$, C—$CONR^6NR^6R^9$, C—$NR^6R^9$, C—$SO_2NR^6R^9$, C—CR=$NNR^6R^9$, C—$CR^6$=$NOR^6$, and C—$R^6$;

$R^1$ is selected from the group consisting of aryl and 5–10 membered aromatic heterocycle containing from 1–4 heteroatoms selected from O, N, and S, and wherein the aryl or the 5–10 membered aromatic heterocycle is optionally substituted with 1–5 $R^7$ groups;

$R^2$ is selected from the group consisting of: $C_{1-4}$ alkyl, $C_{2-4}$ alkenyl, $C_{2-4}$ alkynyl, S—$C_{1-3}$ alkyl, O—$C_{1-3}$ alkyl, $NH_2$, NH—$C_{1-3}$ alkyl, N($C_{1-2}$ alkyl)$_2$, $OCF_3$, cyclopropyl optionally containing from 1–4 substitution groups, cyclobutyl, cyclopropylmethyl, cyclobutylmethyl, 1-methylcyclopropyl, 1-methylcyclobutyl, $CH_2CN$, $CH_2OH$, $CH_2OCH_3$, $CH_2NH_2$, $CH_2NHC_{1-3}$ alkyl, $CH_2NMe_2$, $CF_3$, CHO, $OCH_2CH_2OH$, OCH(Me)$CH_2OH$, $OCH_2CH$(Me)OH, $OCH_2CH_2NMe_2$, and $CHF_2$;

$R^3$ is selected from the group consisting of: H, F, Cl, Br, I, $CF_3$, CHO, $CHR^6OH$, $COCF_3$, CH=NOH, CH=$NOCH_3$, CH=$NNH_2$, CH=NNHMe, CH=$NNMe_2$, CH=$CHR^6$, $C_{1-3}$ alkyl, $C_{1-3}$ alkoxy, $CO_2H$, $CONH_2$, CONH($C_{1-3}$ alkyl), $CONR^6R^9$, $CO_2C_{1-3}$ alkyl, $C(O)C_{1-2}$ alkyl, $NH_2$, $NHR^6$, and $NR^6R^9$;

$R^4$ is selected from the group consisting of: H, F, Cl, Br, I, $CF_3$, $C_{1-3}$ alkyl, $C_{2-3}$ alkenyl, $NH_2$, $NHR^6$, and $NR^6R^9$;

$R^5$ is selected from the group consisting of: H, $C_{1-3}$ alkyl, F, Cl, Br, I, $CF_3$, and $C_{2-3}$ alkenyl;

$R^6$ and $R^9$ are independently, at each occurrence, the same or different, and are selected from the group consisting of: H, $C_{1-8}$ alkyl optionally containing from 1–8 substitution groups, and $C_{3-7}$ cyclo-alkyl, alternatively, $R^6$ and $R^9$, together with the atoms to which they are attached, form a heterocycle having 5–7 atoms in the ring and containing 0–1 additional N, O, or S atom; or, $R^6$ and $R^9$, together with the atoms to which they are attached, form a bicyclic heterocycle having 9–11 atoms in the ring and containing one additional N, S, or O atom; or, $R^6$ and $R^9$, together with the atoms to which they are attached, form a 5–7 membered ring and containing 0–3 additional N, S, or O atoms;

$R^7$ is independently, at each occurrence, selected from the group consisting of: OH, $C_{1-6}$ alkoxy, $OC_{2-6}$ alkyl-$CO_2H$, O—$C_{2-6}$-alkyl-$NR^6R^9$, F, Cl, Br, I, $CF_3$, $OCF_3$, —CN, —$NO_2$, $CO_2H$, $CO_2(C_{1-6}$ alkyl), $CONR^6R^9$, $NR^6CONHOR^6$, $NR^6CONHSO_2R^6$, $NHNR^6C(O)OR^6$, $NR^6C(O)NR^6R^9$, $NH_2$, $NH(C_{1-3}$ alkyl), $N(C_{1-3}$ alkyl)$_2$, —$SO_2NR^6R^9$, $NHSO_2NHCO_2C_{1-4}$ alkyl, $NR^6SO_2NR^6R^9$, $NR^6SO_2CHR^6CH_2NR^6R^9$, $NR^6COCHR^6NR^6R^9$, $NR^6COCHR^6NR^6CHR^6R^9$, $NR^6COCH_2CHR^6NR^6R^9$, $NR^6COCHR^6CH_2NR^6R^9$, $NR^6CO(CH_2)_mNR^6R^9$, $NR^6CONR^6(CH_2)_nNR^6$, $NR^6CO_2(CHR^6)_nNR^6R^9$, $CONR^6NR^6R^9$, $NR^6CONR^6NR^6R^9$, $C_{3-10}$ carbocycle, $NHCONR^6$, $NHCONHCH_2R^6$, $NHCOR^6$, $NHCOCH_2R^6$, $C_{1-10}$ alkyl optionally substituted with 1–5 substitution groups, $C_{2-10}$ alkenyl optionally substituted with 1–5 substitution groups, $C_{2-10}$ alkynyl optionally substituted with 1–5 substitution groups, and $C_{3-10}$ heterocycle containing 1–4 heteroatoms selected from O, N, and S;

$R^8$ is independently, at each occurrence, selected from the group consisting of: =O, OH, $C_{3-6}$ cycloalkyl, $C_{1-6}$ alkoxy, $NH_2$, $NH(C_{1-6}$ alkyl), $N(C_{1-6}$ alkyl)$_2$, F, Cl, Br, I, $CO_2H$, $COR^6$, $CO_2$(benzyl), $CO_2(C_{1-6}$ alkyl), and $CONR^6R^9$;

n at each occurrence is independently selected from 2, 3, 4, 5, and 6; and, m at each occurrence is independently selected from 3, 4, 5, and 6.

The term "alkyl" is intended to include both $C_{1-10}$ branched and straight-chain saturated aliphatic hydrocarbon groups having the specified number of carbon atoms. Examples of alkyl include but are not limited to, methyl, ethyl, n-propyl, i-propyl, n-butyl, s-butyl, t-butyl, n-pentyl, s-pentyl, n- and s-hexyl, n-and s-heptyl, and, n- and s-octyl.

For purposes of the present invention the term "alkenyl" is defined as a $C_{2-10}$ branched or straight-chain unsaturated aliphatic hydrocarbon groups having one or more double bonds between two or more carbon atoms. Examples of alkene groups include ethenyl, propenyl, butenyl, pentenyl, hexenyl, heptenyl, octenyl and nonenyl and the corresponding $C_{2-10}$ dienes, trienes and quadenes. The term "alkynyl" is defined as a $C_{2-10}$ branched or straight-chain unsaturated aliphatic hydrocarbon groups having one or more triple bonds between two or more carbon atoms. Examples of alkynes include ethynyl, propynyl, butynyl, pentynyl, hexynyl, heptynyl, octynyl and nonynyl.

The term "substitution groups" means that one or more hydrogens on the molecule or atom modified by the words "optionally containing" are replaced with 1, 2, 3, 4, 5, 6, 7, 8 or 9 substitution groups provided that the indicated atom's normal valency is not exceeded, and that the substitution results in a stable compound. Such "substitution groups" may be selected from the group consisting of H, —OH, $C_{1-10}$ alkyl, $C_{2-10}$ alkenyl, $C_{2-10}$ alkynyl, —OR, —$NH_2$, —NHR, —NR'R, —COOH, —COOR, —CONHR, —CONR'R, —CHO, —CRO, —$SC_{1-8}$ alkyl, —halo, —CN, —$NO_2$, —$SO_2$, phosphoryl, imino, sulfhydryl, alklthio, thioester, carbocyclic, aryl, heteroaryl, bicyclic and tricyclic groups. When a substitution group is a keto (i.e., =O) group, then 2 hydrogens on the atom are replaced. Keto substituents are not present on aromatic moieties. The terms R and R' refer to substitution groups, which may be the same or different and may be selected from H, —OH, $C_{1-10}$ alkyl, $C_{2-10}$ alkenyl, $C_{2-10}$ alkynyl, —$NH_2$, —COOH, —CHO, —$SC_{1-8}$ alkyl, -halo, —CN, —$NO_2$, —$SO_2$, carbocyclic, aryl, heteroaryl, bicyclic and tricyclic structures.

The scope of the present invention is intended to include all permutations and combinations of the substitution groups on the backbone structure specified by formulas I and II above with the proviso that each permutation or combination can be selected by specifying the appropriate R or substitution groups.

Thus, for example, the term "$C_{1-10}$ alkyl optionally containing from 1–8 substitution groups" refers to alkyl moieties containing saturated bonds or having one or more hydrogens replaced by, for example, halogen, hydroxyl, carbonyl, alkoxy, ester, ether, cyano, phosphoryl, amino, imino, amido, sulfhydryl, alklthio, thioester, sulfonyl, nitro, heterocyclo, aryl, or hetero-aryl.

The terms "halo" or "halogen" as used herein refer to fluoro, chloro, bromo and iodo.

The term "aryl" is intended to mean an aromatic moiety containing the specified number of carbon atoms, such as, but not limited to phenyl, tropone, indanyl or naphthyl.

The terms "cycloalkyl" and "bicycloalkyl" are intended to mean any stable ring system, which may be saturated or partially unsaturated. Examples of such include, but are not limited to, cyclopropyl, cyclopentyl, cyclohexyl, norbornyl, bicyclo[2.2.2]nonane, adamantyl, or tetrahydronaphthyl (tetralin).

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated, unsaturated or aromatic, and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. In this regard, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, 5 acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "independently selected from", "independently, at each occurance" or similar language, means that the labeled R substitution group may appear more than once and may be the same or different when appearing multiple times in the same structure. Thus if the labeled $R^6$ substitution group appears four times in a given permutation of Formula I, then each of those labeled $R^6$ substitution groups may be, for example, a different alkyl group falling within the definition of $R^6$.

In one embodiment of the present invention, the compound of formula (I) or formula (II) is selected from:
a) 1-(2,4,6-trichlorophenyl)-3-ethyl-6-(4-hydroxy-3-methoxybenzyl)pyrazolo[3,4-d]pyrimidin-4-one;
b) 1-(2,4,6-trichlorophenyl)-3-ethyl-6-(4-hydroxybenzyl)pyrazolo[3,4-d]pyrimidin-4-one;
c) 1-(2,4,6-trichlorophenyl)-3-ethyl-6-(3-hydroxy-4-methoxybenzyl)pyrazolo[3,4-d]pyrimidin-4-one;
d) 1-(2,4,6-trichlorophenyl)-3-ethyl-6-(3-aminobenzyl)pyrazolo[3,4-d]pyrimidin-4-one;
e) 1-(2,4,6-trichlorophenyl)-3-ethyl-6-(3-hydroxybenzyl)pyrazolo[3,4-d]pyrimidin-4-one;
f) 1-(2,4,6-trichlorophenyl)-3-ethyl-6-(4-aminobenzyl)pyrazolo[3,4-d]pyrimidin-4-one;
g) 1-(2,4,6-trichlorophenyl)-3-ethyl-6-(4-acetamidobenzyl)pyrazolo[3,4-d]pyrimidin-4-one;
h) 1-(2,4,6-trichlorophenyl)-3-ethyl-6-(4-(N-(t-butoxycarbonyl)glycinamido)benzyl)pyrazolo[3,4-d]pyrimidin-4-one;
i) 1-(2,4,6-trichlorophenyl)-3-ethyl-6-(4-(2-(N,N-dimethylamino)ethylaminocarbonylamino)benzyl)pyrazolo[3,4-d]pyrimidin-4-one;
j) 1-(2,4,6-trichlorophenyl)-3-ethyl-6-(3-amino-2-methylbenzyl)pyrazolo[3,4-d]pyrimidin-4-one;
k) 1-(2,4,6-trichlorophenyl)-3-ethyl-6-(4-(pyrid-2-ylmethylaminocarbonylamino)benzyl)pyrazolo[3,4-d]pyrimidin-4-one;
l) 1-(2,4,6-trichlorophenyl)-3-ethyl-6-(4-glycinamidobenzyl)pyrazolo[3,4-d]pyrimidin-4-one;
m) 1-(2,4,6-trichlorophenyl)-3-ethyl-6-(4-(pyrid-4-ylmethylaminocarbonylamino)benzyl)pyrazolo[3,4-d]pyrimidin-4-one;
n) 1-(2,4,6-trichlorophenyl)-3-ethyl-6-(para-biphen-4-ylmethyl)pyrazolo[3,4-d]pyrimidin-4-one;
o) 1-(2,6-dichlorophenyl)-3-ethyl-6-(4-aminobenzyl)pyrazolo[3,4-d]pyrimidin-4-one;
p) 1-(2,4,6-trichlorophenyl)-3-ethyl-6-(4-(4-methylpiperazin-1-ylcarbonylamino)benzyl)pyrazolo[3,4-d]pyrimidin-4-one;
q) 1-(2,4,6-trichlorophenyl)-3-ethyl-6-(4-(dimethylamino)benzyl)pyrazolo[3,4-d]pyrimidin-4-one;
r) 1-(2,4,6-trichlorophenyl)-3-ethyl-6-(2-(hydroxymethyl)benzyl)pyrazolo[3,4-d]pyrimidin-4-one;
s) 1-(2,6-dichlorophenyl)-3-ethyl-6-(4-hydroxybenzyl)pyrazolo[3,4-d]pyrimidin-4-one;
t) 1-(2,4,6-trichlorophenyl)-3-ethyl-6-(4-(methoxyaminocarbonylmethyl)benzyl)pyrazolo[3,4-d]pyrimidin-4-one;
u) 1-(2,6-dichlorophenyl)-3-ethyl-6-(3-methoxybenzyl)pyrazolo[3,4-d]pyrimidin-4-one;
v) 1-(2,6-dichlorophenyl)-3-ethyl-6-(4-hydroxybenzyl)pyrazolo[3,4-d]pyrimidin-4-one;
w) 1-(2-chloro-6-methylphenyl)-3-ethyl-6-(4-hydroxybenzyl)pyrazolo[3,4-d]pyrimidin-4-one;
x) 1-(2,4,6-trichlorophenyl)-3-ethyl-6-(3,5-dihydroxybenzyl)pyrazolo[3,4-d]pyrimidin-4-one;
y) 1-(2,4,6-trichlorophenyl)-3-ethyl-6-(4-hydroxy-3-methylbenzyl)pyrazolo[3,4-d]pyrimidin-4-one;
z) 1-(2,4,6-trichlorophenyl)-3-ethyl-6-(4-amino-3-nitrobenzyl)pyrazolo[3,4-d]pyrimidin-4-one;
aa) 1-(2,4,6-trichlorophenyl)-3-ethyl-6-(4-(methylaminocarbonylamino)benzyl)pyrazolo[3,4-d]pyrimidin-4-one;
ab) 1-(2,4,6-trichlorophenyl)-3-ethyl-6-(3-(methanesulfonamido)benzyl)pyrazolo[3,4-d]pyrimidin-4-one;
ac) 1-(2,4,6-trichlorophenyl)-3-ethyl-6-(4-(methanesulfonamido)benzyl)pyrazolo[3,4-d]pyrimidin-4-one;
ad) 1-(2,6-dichloro-4-(pyrid-3-ylaminocarbonyl)phenyl)-3-ethyl-6-(3-methoxybenzyl)pyrazolo[3,4-d]pyrimidin-4-one;
ae) 1-(2,6-dichloro-4-(pyrid-4-ylaminocarbonyl)phenyl)-3-ethyl-6-(3-methoxybenzyl)pyrazolo[3,4-d]pyrimidin-4-one;
af) 1-(2,6-dichloro-4-(cyclopropylaminocarbonyl)phenyl)-3-ethyl-6-(3-methoxybenzyl)pyrazolo[3,4-d]pyrimidin-4-one;
ag) 1-(2,6-dichloro-4-(N-(pyrid-3-ylmethyl)aminocarbonyl)phenyl)-3-ethyl-6-(3-methoxybenzyl)pyrazolo[33,4-one;

ah) 1-(2,6-dichloro-4-(N-(pyrid-2-ylmethyl) aminocarbonyl)phenyl)-3-ethyl-6-(3-methoxybenzyl) pyrazolo[3,4-d]pyrimidin-4-one;

ai) 1-(2,6-dichloro-4-(ethylaminocarbonyl)phenyl)-3-ethyl-6-(3-methoxybenzyl)pyrazolo[3,4-d]pyrimidin-4-one;

aj) 1-(2,6-dichloro-4-(benzylaminocarbonyl)phenyl)-3-ethyl-6-(3-hydroxybenzyl)pyrazolo[3,4-d]pyrimidin-4-one;

ak) 1-(2,6-dichloro-4-(2-(dimethylamino) ethylaminocarbonyl)phenyl)-3-ethyl-6-(3-methoxybenzyl)pyrazolo[3,4-d]pyrimidin-4-one;

al) 1-(2,6-dichloro-4-(methylaminocarbonyl)phenyl)-3-ethyl-6-(4-methoxybenzyl)pyrazolo[3,4-d]pyrimidin-4-one;

am) 1-(2,4,6-trichlorophenyl)-3-ethyl-6-(3-(N,N-dimethylglycinamido)-2-methylbenzyl)pyrazolo[3,4-d]pyrimidin-4-one;

an) 1-(2,4,6-trichlorophenyl)-3-ethyl-6-(4-(N,N-dimethylglycinamido)benzyl)pyrazolo[3,4-d] pyrimidin-4-one;

ao) 1-(2,4,6-trichlorophenyl)-3-ethyl-6-(4-(N-methylglycinamido)benzyl)pyrazolo[3,4-d]pyrimidin-4-one;

ap) 1-(2,6-dichloro-4-bromophenyl)-3-ethyl-6-(4-hydroxybenzyl)pyrazolo[3,4-d]pyrimidin-4-one;

aq) 1-(2,4,6-trichlorophenyl)-3-isopropyl-6-(4-(methoxycarbonylamino)benzyl)pyrazolo[3,4-d] pyrimidin-4-one;

ar) 1-(2,4,6-trichlorophenyl)-3-isopropyl-6-(3-hydroxybenzyl)pyrazolo[3,4-d]pyrimidin-4-one;

as) 1-(2,4,6-trichlorophenyl)-3-isopropyl-6-(3-hydroxy-4-methoxybenzyl)pyrazolo[3,4-d]pyrimidin-4-one;

at) 1-(2,4,6-trichlorophenyl)-3-isopropyl-6-(3-aminobenzyl)pyrazolo[3,4-d]pyrimidin-4-one;

au) 1-(2,4,6-trichlorophenyl)-3-isopropyl-6-(3-(methanesulfonamido)benzyl)pyrazolo[3,4-d] pyrimidin-4-one;

av) 1-(2,4,6-trichlorophenyl)-3-isopropyl-6-(3-(difluoroacetamido)benzyl)pyrazolo[3,4-d]pyrimidin-4-one;

aw) 1-(2,4,6-trichlorophenyl)-3-isopropyl-6-(3-(acetamido)benzyl)pyrazolo[3,4-d]pyrimidin-4-one;

ax) 1-(2,4,6-trichlorophenyl)-3-isopropyl-6-(3-(methylaminocarbonylamino)benzyl)pyrazolo[3,4-d] pyrimidin-4-one;

ay) 1-(2,4,6-trichlorophenyl)-3-isopropyl-6-(3-methoxybenzyl)pyrazolo[3,4-d]pyrimidin-4-one;

az) 1-(2,4,6-trichlorophenyl)-3-isopropyl-6-(4-(azetidin-3-ylcarbonylamino)benzyl)pyrazolo[3,4-d]pyrimidin-4-one;

ba) 1-(2,4,6-trichlorophenyl)-3-isopropyl-6-(4-(2-aminoethylaminomethylcarbonylamino)benzyl) pyrazolo[3,4-d]pyrimidin-4-one;

bb) 1-(2,4,6-trichlorophenyl)-3-isopropyl-6-(4-(isopropylaminomethylcarbonylamino)benzyl) pyrazolo[3,4-d]pyrimidin-4-one;

bc) 1-(2,4,6-trichlorophenyl)-3-isopropyl-6-(4-(4-fluorobenzylaminomethylcarbonylamino)benzyl) pyrazolo[3,4-d]pyrimidin-4-one;

bd) 1-(2,4,6-trichlorophenyl)-3-isopropyl-6-(4-(pyrrolidin-1-ylmethylcarbonylamino)benzyl)pyrazolo[3,4-d]pyrimidin-4-one;

be) 1-(2,4,6-trichlorophenyl)-3-isopropyl-6-(4-(pyrid-2-ylmethylaminomethylcarbonylamino)benzyl)pyrazolo[3,4-d]pyrimidin-4-one;

bf) 1-(2,4,6-trichlorophenyl)-3-isopropyl-6-(4-(2-(t-butoxycarbonylamino) ethylaminomethylcarbonylamino)benzyl)pyrazolo[3,4-d]pyrimidin-4-one;

bg) 1-(2,4,6-trichlorophenyl)-3-isopropyl-6-(4-(pyrid-3-ylmethylaminomethylcarbonylamino)benzyl)pyrazolo[3,4-d]pyrimidin-4-one;

bh) 1-(2,4,6-trichlorophenyl)-3-isopropyl-6-(4-(pyrid-4-ylmethylaminomethylcarbonylamino)benzyl)pyrazolo[3,4-d]pyrimidin-4-one;

bi) 1-(2,4,6-trichlorophenyl)-3-isopropyl-6-(4-(2-(morpholin-4-yl)ethylaminomethylcarbonylamino) benzyl)pyrazolo[3,4-d]pyrimidin-4-one;

bj) 1-(2,6-dichlorophenyl)-3-isopropyl-6-(4-(methylaminocarbonylmethyl)benzyl)pyrazolo[3,4-d] pyrimidin-4-one;

bk) 1-(2,6-dichlorophenyl)-3-isopropyl-6-(4-(ethylaminocarbonylmethyl)benzyl)pyrazolo[3,4-d] pyrimidin-4-one;

bl) 1-(2,6-dichlorophenyl)-3-isopropyl-6-(4-(piperazin-1-ylcarbonylmethyl)benzyl)pyrazolo[3,4-d]pyrimidin-4-one;

bm) 1-(2,4,6-trichlorophenyl)-3-isopropyl-6-(4-methylpyrid-3-ylmethyl)pyrazolo[3,4-d]pyrimidin-4-one;

bn) 1-(2,6-dichlorophenyl)-3-isopropyl-6-(4-(2-(dimethylamino)ethylaminocarbonylmethyl)benzyl) pyrazolo[3,4-d]pyrimidin-4-one;

bo) 1-(2,4,6-trichlorophenyl)-3-isopropyl-6-(4-(2,2-dimethylhydrazin-1-ylcarbonylamino)benzyl)pyrazolo[3,4-d]pyrimidin-4-one;

bp) 1-(2,4,6-trichlorophenyl)-3-isopropyl-6-(4-(1-hydroxybut-4-ylaminocarbonylamino)benzyl)pyrazolo[3,4-d]pyrimidin-4-one;

bq) (+/−)1-(2,4,6-trichlorophenyl)-3-isopropyl-6-(4-(2-hydroxyprop-1-ylaminomethylcarbonylamino)benzyl) pyrazolo[3,4-d]pyrimidin-4-one;

br) (+/−)1-(2,4,6-trichlorophenyl)-3-isopropyl-6-(4-(1-hydroxyprop-2-ylaminomethylcarbonylamino)benzyl) pyrazolo[3,4-d]pyrimidin-4-one;

bs) 1-(2,4,6-trichlorophenyl)-3-isopropyl-6-(pyrid-3-ylmethyl)pyrazolo[3,4-d]pyrimidin-4-one;

bt) 1-(2,4,6-trichlorophenyl)-3-isopropyl-6-(4-aminobenzyl)pyrazolo[3,4-d]pyrimidin-4-one;

bu) 1-(2,4,6-trichlorophenyl)-3-isopropyl-6-(4-(dimethylamino)benzyl)pyrazolo[3,4-d]pyrimidin-4-one;

bv) 1-(2,4,6-trichlorophenyl)-3-isopropyl-6-(pyrid-4-ylmethyl)pyrazolo[3,4-d]pyrimidin-4-one;

bw) 1-(2,4,6-trichlorophenyl)-3-isopropyl-6-(4-(N,N-dimethylglycinamido)-3-hydroxybenzyl)pyrazolo[3,4-d]pyrimidin-4-one;

bx) 1-(2,4,6-trichlorophenyl)-3-isopropyl-6-(4-(N,N-dimethylglycinamido)-3-methoxybenzyl)pyrazolo[3,4-d]pyrimidin-4-one;

by) 1-(2,4,6-trichlorophenyl)-3-isopropyl-6-(4-(methylaminocarbonylamino)-3-methoxybenzyl) pyrazolo [3,4-d]pyrimidin-4-one;

bz) 1-(2,4,6-trichlorophenyl)-3-isopropyl-6-(4-(N-(3-(dimethylamino)propyl)aminocarbonylamino)benzyl) pyrazolo[3,4-d]pyrimidin-4-one;

ca) 1-(2,4,6-trichlorophenyl)-3-isopropyl-6-(benzoxazol-2-on-6-ylmethyl)pyrazolo[3,4-d]pyrimidin-4-one;

cb) 1-(2,6-dichlorophenyl)-3-isopropyl-6-(4-(4-methylpiperazin-1-ylcarbonylmethyl)benzyl)pyrazolo[3,4-d]pyrimidin-4-one;

cc) 1-(2,6-dichlorophenyl)-3-isopropyl-6-(4-(N-methyl,N-(2-(dimethylamino)ethyl)aminocarbonylmethyl)benzyl)-pyrazolo[3,4-d]pyrimidin-4-one;

cd) 1-(2,4,6-trichlorophenyl)-3-isopropyl-6-(4-(methylaminocarbonylamino)-3-hydroxybenzyl)pyrazolo[3,4-d]pyrimidin-4-one;

ce) 1-(2,4,6-trichlorophenyl)-3-isopropyl-6-(4-(4-methylpiperazin-1-ylmethylcarbonylamino)benzyl)pyrazolo[3,4-d]pyrimidin-4-one;

cf) 1-(2,4,6-trichlorophenyl)-3-isopropyl-6-(4-(piperazin-1-ylmethylcarbonylamino)benzyl)pyrazolo[3,4-d]pyrimidin-4-one;

cg) 1-(2,4,6-trichlorophenyl)-3-isopropyl-6-(4-(morpholin-4-ylmethylcarbonylamino)benzyl)pyrazolo[3,4-d]pyrimidin-4-one;

ch) 1-(2,4,6-trichlorophenyl)-3-isopropyl-6-(4-(imidazol-1-ylmethylcarbonylamino)benzyl)pyrazolo[3,4-d]pyrimidin-4-one;

ci) 1-(2,4,6-trichlorophenyl)-3-isopropyl-6-(4-(N-methyl-N-(1-methylpiperidin-4-yl)aminomethylcarbonylamino)benzyl)pyrazolo[3,4-d]pyrimidin-4-one;

cj) 1-(2,4,6-trichlorophenyl)-3-isopropyl-6-(4-(cyclopropylaminomethylcarbonylamino)benzyl)pyrazolo[3,4-d]pyrimidin-4-one;

ck) 1-(2,4,6-trichlorophenyl)-3-isopropyl-6-(4-(N,N-dimethylglycinamido)benzyl)pyrazolo[3,4-d]pyrimidin-4-one;

cl) 1-(2,4,6-trichlorophenyl)-3-isopropyl-6-(4-(methylaminomethylcarbonylamino)benzyl)pyrazolo[3,4-]pyrimidin-4-one;

cm) 1-(2,4,6-trichlorophenyl)-3-isopropyl-6-(3-aminoindazol-5-ylmethyl)pyrazolo[3,4-d]pyrimidin-4-one;

cn) 1-(2,4,6-trichlorophenyl)-3-isopropyl-6-(4-(N-methyl,N-(2-(dimethylamino)ethyl)aminomethylcarbonylamino)benzyl)-pyrazolo[3,4-d]pyrimidin-4-one;

co) 1-(2,4,6-trichlorophenyl)-3-isopropyl-6-(4-(4-methylpiperazin-1-ylcarbonylmethyl)benzyl)pyrazolo[3,4-]pyrimidin-4-one;

cp) 1-(2,4,6-trichlorophenyl)-3-isopropyl-6-(4-(azetidin-1-ylmethylcarbonylamino)benzyl)pyrazolo[3,4-d]pyrimidin-4-one;

cq) 1-(2,4,6-trichlorophenyl)-3-isopropyl-6-(3-hydroxy-4-(imidazol-1-ylmethylcarbonylamino)benzyl)pyrazolo[3,4-d]pyrimidin-4-one;

cr) 1-(2,4,6-trichlorophenyl)-3-isopropyl-6-(4-(4-methylpiperazin-1-ylcarbonylamino)benzyl)pyrazolo[3,4-]pyrimidin-4-one;

cs) 1-(2,4,6-trichlorophenyl)-3-isopropyl-6-(4-(3-(dimethylamino)prop-1-ylaminocarbonylamino)benzyl)pyrazolo[3,4-d]pyrimidin-4-one;

ct) 1-(2,4,6-trichlorophenyl)-3-isopropyl-6-(4-(4-methylhomopiperazin-1-ylcarbonylamino)benzyl)pyrazolo[3,4-d]pyrimidin-4-one;

cu) 1-(2,4,6-trichlorophenyl)-3-isopropyl-6-(4-(4-methylpiperazin-2-ylcarbonylamino)benzyl)pyrazolo[3,4-]pyrimidin-4-one;

cv) 1-(2,4,6-trichlorophenyl)-3-isopropyl-6-(4-(t-butoxycarbonylaminosulfonamido)benzyl)pyrazolo[3,4-d]pyrimidin-4-one;

cw) 1-(2-chloro-6-methylphenyl)-3-isopropyl-6-(4-aminobenzyl)pyrazolo[3,4-d]pyrimidin-4-one;

cx) 1-(2,4,6-trichlorophenyl)-3-isopropyl-6-(4-(2-(morpholin-4-yl)ethylaminothiocarbonylamino)benzyl)pyrazolo[3,4-d]pyrimidin-4-one;

cy) 1-(2-chloro-6-methylphenyl)-3-isopropyl-6-(4-(N,N-dimethylglycinamido)benzyl)pyrazolo[3,4-d]pyrimidin-4-one;

cz) 1-(2,4,6-trichlorophenyl)-3-isopropyl-6-(4-bromobenzyl)pyrazolo[3,4-d]pyrimidin-4-one;

da) 1-(2,4,6-trichlorophenyl)-3-isopropyl-6-(4-(piperazin-2-ylcarbonylamino)benzyl)pyrazolo[3,4-d]pyrimidin-4-one;

db) 1-(2,4,6-trichlorophenyl)-3-isopropyl-6-(4-(1,4-dimethylpiperazin-2-ylcarbonylamino)benzyl)pyrazolo[3,4-d]pyrimidin-4-one;

dc) 1-(2,4,6-trichlorophenyl)-3-isopropyl-6-(4-(2-(dimethylamino)ethylsulfonamido)benzyl)pyrazolo[3,4-d]pyrimidin-4-one;

dd) 1-(2,4,6-trichlorophenyl)-3-isopropyl-6-(4-amino-3-methoxybenzyl)pyrazolo[3,4-d]pyrimidin-4-one;

de) 1-(2,4,6-trichlorophenyl)-3-isopropyl-6-(4-hydantoin-3-ylbenzyl)pyrazolo[3,4-d]pyrimidin-4-one;

df) 1-(2,4,6-trichlorophenyl)-3-isopropyl-6-(2H-1,4-benzoxazin-3-on-7-ylmethyl)pyrazolo[3,4-d]pyrimidin-4-one;

dg) 1-(2,4,6-trichlorophenyl)-3-isopropyl-6-(4-(N-(2-(dimethylamino)ethyl)aminocarbonylamino)benzyl)pyrazolo[3,4-d]pyrimidin-4-one;

dh) 1-(2,4,6-trichlorophenyl)-3-isopropyl-6-(4-(2-hydroxyethylaminocarbonylamino)benzyl)pyrazolo[3,4-d]pyrimidin-4-one;

di) 1-(2,4,6-trichlorophenyl)-3-isopropyl-6-(4-methylbenzyl)pyrazolo[3,4-d]pyrimidin-4-one;

dj) 1-(2,4,6-trichlorophenyl)-3-isopropyl-6-(2-methylbenzyl)pyrazolo[3,4-d]pyrimidin-4-one;

dk) 1-(2,4,6-trichlorophenyl)-3-isopropyl-6-(4-glycinamidobenzyl)pyrazolo[3,4-d]pyrimidin-4-one;

dl) 1-(2,4,6-trichlorophenyl)-3-isopropyl-6-(4-(N-methylglycinamido)benzyl)pyrazolo[3,4-d]pyrimidin-4-one;

dm) 1-(2,4,6-trichlorophenyl)-3-isopropyl-6-(4-(2-(dimethylamino)ethylaminomethylcarbonylamino)benzyl)pyrazolo[3,4-d]pyrimidin-4-one;

dn) 1-(2,4,6-trichlorophenyl)-3-isopropyl-6-(4-(4-(aminomethyl)piperidin-1-ylmethylcarbonylamino)benzyl)pyrazolo[3,4-d]pyrimidin-4-one;

do) 1-(2,4,6-trichlorophenyl)-3-isopropyl-6-(4-(homopiperazin-1-ylmethylcarbonylamino)benzyl)pyrazolo[3,4-d]pyrimidin-4-one;

dp) 1-(2,4,6-trichlorophenyl)-3-isopropyl-6-(4-(ethylaminomethylcarbonylamino)benzyl)pyrazolo[3,4-d]pyrimidin-4-one;

dq) 1-(2,4,6-trichlorophenyl)-3-isopropyl-6-(4-(dimethylaminomethyl)-3-hydroxybenzyl)pyrazolo[3,4-d]pyrimidin-4-one;

dr) (S)-1-(2,4,6-trichlorophenyl)-3-isopropyl-6-(4-(N-methylprolinamido)benzyl)pyrazolo[3,4-d]pyrimidin-4-one;

ds) (+/−)-1-(2,4,6-trichlorophenyl)-3-isopropyl-6-(4-(N-,N-dimethylalaninamido)benzyl)pyrazolo[3,4-d]pyrimidin-4-one;

dt) 1-(2,4,6-trichlorophenyl)-3-isopropyl-6-(4-(1,4,7-triazacyclonon-1-ylmethylcarbonylamino)benzyl)pyrazolo[3,4-d]pyrimidin-4-one;

du) 1-(2,4,6-trichlorophenyl)-3-isopropyl-6-(3-amino-2-methylbenzyl)pyrazolo[3,4-d]pyrimidin-4-one;

dv) 1-(2,4,6-trichlorophenyl)-3-isopropyl-6-(4-(2-(morpholin-4-yl)ethylaminocarbonylamino)benzyl)pyrazolo[3,4-d]pyrimidin-4-one;

dw) 1-(2,4,6-trichlorophenyl)-3-isopropyl-6-(3-(N-,N-dimethylglycinamido)-2-methylbenzyl)pyrazolo[3,4-d]pyrimidin-4-one;

dx) 1-(2,4,6-trichlorophenyl)-3-isopropyl-6-(4-(4-methylpiperazin-1-ylaminocarbonylamino)benzyl)pyrazolo[3,4-d]pyrimidin-4-one;

dy) 1-(2,4,6-trichlorophenyl)-3-isopropyl-6-(4-(morpholin-4-ylaminocarbonylamino)benzyl)pyrazolo[3,4-d]pyrimidin-4-one;

dz) 1-(2,4,6-trichlorophenyl)-3-isopropyl-6-(4-(methoxyaminocarbonylamino)benzyl)pyrazolo[3,4-d]pyrimidin-4-one;

ea) 1-(2,4,6-trichlorophenyl)-3-isopropyl-6-(4-(methanesulfonamidocarbonylamino)benzyl)pyrazolo[3,4-]pyrimidin-4-one;

eb) 1-(2,4,6-trichlorophenyl)-3-isopropyl-6-(4-(N-methyl,N-(2-(dimethylamino)ethyl)aminocarbonylamino)benzyl)pyrazolo[3,4-d]pyrimidin-4-one;

ec) 1-(2,4,6-trichlorophenyl)-3-isopropyl-6-(4-(N-methyl,N-(1-methylpiperidin-4-yl)aminocarbonylamino)benzyl)pyrazolo[3,4-d]pyrimidin-4-one;

ed) (+/−)-1-(2,4,6-trichlorophenyl)-3-isopropyl-6-(4-(tetrahydrofur-2-ylmethylaminocarbonylamino)benzyl)-pyrazolo[3,4-d]pyrimidin-4-one;

ee) (+/−)-1-(2,4,6-trichlorophenyl)-3-isopropyl-6-(4-(1-hydroxypent-2-ylaminocarbonylamino)benzyl)pyrazolo[3,4-d]pyrimidin-4-one;

ef) (+/−)-1-(2,4,6-trichlorophenyl)-3-isopropyl-6-(4-(1-hydroxyprop-2-ylaminocarbonylamino)benzyl)pyrazolo[3,4-d]pyrimidin-4-one;

eg) (+/−)-1-(2,4,6-trichlorophenyl)-3-isopropyl-6-(4-(2-hydroxyprop-1-ylaminocarbonylamino)benzyl)pyrazolo[3,4-d]pyrimidin-4-one;

eh) (+/−)-1-(2,4,6-trichlorophenyl)-3-isopropyl-6-(4-(2-(dimethylamino)prop-1-ylaminocarbonylamino)benzyl)pyrazolo[3,4-d]pyrimidin-4-one;

ei) 1-(2,4,6-trichlorophenyl)-3-cyclopropyl-6-(3-hydroxy-4-methoxybenzyl)pyrazolo[3,4-d]pyrimidin-4-one;

ej) 1-(2,4,6-trichlorophenyl)-3-cyclopropyl-6-(indazol-6-ylmethyl)pyrazolo[3,4-d]pyrimidin-4-one;

ek) 1-(2,4,6-trichlorophenyl)-3-cyclopropyl-6-(indazol-5-ylmethyl)pyrazolo[3,4-d]pyrimidin-4-one;

el) 1-(2,4,6-trichlorophenyl)-3-cyclopropyl-6-(indazol-4-ylmethyl)pyrazolo[3,4-d]pyrimidin-4-one;

em) 1-(2,4,6-trichlorophenyl)-3-cyclopropyl-6-(benzoxazol-2-on-5-ylmethyl)pyrazolo[3,4-d]pyridin-4-one;

en) 1-(2,4,6-trichlorophenyl)-3-cyclopropyl-6-(3-hydroxy-4-nitrobenzyl)pyrazolo[3,4-d]pyrimidin-4-one;

eo) 1-(2,4,6-trichlorophenyl)-3-cyclopropyl-6-(4-aminobenzyl)pyrazolo[3,4-d]pyrimidin-4-one;

ep) 1-(2,4,6-trichlorophenyl)-3-cyclopropyl-6-(4-(N,N-dimethylglycinamido)benzyl)pyrazolo[3,4-d]pyrimidin-4-one;

eq) 1-(2,4,6-trichlorophenyl)-3-isopropyl-6-(4-(cis-3,4-dimethylpiperazin-1-ylmethylcarbonylamino)benzyl)pyrazolo[3,4-d]pyrimidin-4-one;

er) 1-(2,4,6-trichlorophenyl)-3-isopropyl-6-(4-(trans-2,5-dimethylpiperazin-1-ylmethylcarbonylamino)benzyl)pyrazolo[3,4-d]pyrimidin-4-one;

es) 1-(2,4,6-trichlorophenyl)-3-isopropyl-6-(4-(3-methylpiperazin-1-ylmethylcarbonylamino)benzyl)pyrazolo[3,4-d]pyrimidin-4-one;

et) 1-(2,4,6-trichlorophenyl)-3-isopropyl-6-(5-(dimethylaminomethyl)-1-methylpyrrol-2-yl)pyrazolo[3,4-d]pyrimidin-4-one;

eu) 1-(2,4,6-trichlorophenyl)-3-isopropyl-6-(4-(4-methylpiperazin-1-ylaminocarbony)benzyl)pyrazolo[3,4-d]pyrimidin-4-one;

ev) 1-(2,4,6-trichlorophenyl)-3-isopropyl-6-(3-(N-methyl, N-(2-(dimethylamino)ethyl)aminocarbonylamino)benzyl)pyrazolo[3,4-d]pyrimidin-4-one;

ew) 1-(2-chloro-6-methylphenyl)-3-isopropyl-6-(4-(N-methyl,N-(1-methylpiperidin-4-yl)aminocarbonylamino)benzyl)pyrazolo[3,4-d]pyrimidin-4-one;

ex) 1-(2-chloro-6-methylphenyl)-3-isopropyl-6-(4-(N-methyl-N-(1-methylpiperidin-4-yl)aminomethylcarbonylamino)benzyl)pyrazolo[3,4-d]pyrimidin-4-one;

ey) 1-(2,4,6-trichlorophenyl)-3-ethyl-6-(4-(N-methyl,N-((3S,4S)-4-dimethylaminotetrahydrofur-3-yl)aminocarbonyl amino)benzyl)pyrazolo[3,4-d]pyrimidin-4-one;

ez) 1-(2,4,6-trichlorophenyl)-3-isopropyl-6-(3-(N-methyl, N-(2-(dimethylamino)ethyl)aminocarbonyl)benzyl)pyrazolo[3,4-d]pyrimidin-4-one;

fa) 1-(2,4,6-trichlorophenyl)-3-isopropyl-6-(4-(2-pyrrolidin-1-ylethylaminocarbonyamino)benzyl)pyrazolo[3,4-]pyrimidin-4-one;

fb) 1-(2,6-dichlorophenyl)-3-isopropyl-6-(4-(N-methyl,N-(2-(dimethylamino)ethyl)aminocarbonymethyl)benzyl)pyrazolo[3,4-d]pyrimidin-4-one;

fc) 1-(2,6-dichlorophenyl)-3-isopropyl-6-(4-(N-(2-(dimethylamino)ethyl)aminocarbonymethyl)benzyl)pyrazolo[3,4-d]pyrimidin-4-one; 3,4-d]pyrimidin-4-one;

fd) 1-(2,4,6-trichlorophenyl)-3-isopropyl-6-(4-(N-(2-(dimethylamino)ethyl)aminocarbonyl)benzyl)pyrazolo[3,4-d]pyrimidin-4-one;

fe) 1-(2,4,6-trichlorophenyl)-3-isopropyl-6-(4-(methylamino)benzyl)pyrazolo[3,4-d]pyrimidin-4-one;

ff) 1-(2,4,6-trichlorophenyl)-3-isopropyl-6-(4-(N-methyl-N-(1-methylpiperidin-4-yl)aminocarbonylamino)benzyl)pyrazolo[3,4-d]pyrimidin-4-one;

fg) 1-(2,4,6-trichlorophenyl)-3-isopropyl-6-(4-(N-methyl, N-(2-(dimethylamino)ethyl)aminocarbonylamino)benzyl)pyrazolo[3,4-d]pyrimidin-4-one;

fh) 1-(2,6-dichloro-4-sulfonamidophenyl)-3-isopropyl-6-(3-methoxybenzyl)pyrazolo[3,4-d]pyrimidin-4-one; and f) 1-(4-aminomethyl-2,6-dichlorophenyl)-3-isopropyl-6-(3-methoxybenzyl)pyrazolo[3,4-d]pyrimidin-4-one.

The skilled artisan will understand that all forms of the organic compounds set forth in the present invention are intended to fall within the scope of the present invention, including, but not limited to, pharmaceutically acceptable salts, prodrugs, isomers, enantiomers and crystal forms.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, EtOAc, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference, in it's entirity as though set forth in full.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs", as the term is used herein, is intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Examples of prodrugs include, but are not limited to, acetate, formate, and benzoate derivatives of alcohol and amine functional groups in the compounds of the present invention.

The term "therapeutically effective amount" of a compound of the present invention means an amount effective to inhibit the action of the class of enzymes known as cyclin dependent kinases or treat the symptoms of cancer or other proliferative diseases in a host.

As used herein, the term "anti-cancer" or "anti-proliferative" agent includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea.

The compounds of the present invention may contain one or more asymmetrically substituted carbon atoms or chiral centers, and may be isolated in optically active or racemic forms. The skilled artisan will appreciate that it is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated. All processes used to prepare compounds of the present invention and intermediates made therein are considered to be part of the present invention.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include $^{13}C$ and $^{14}C$.

DOSAGE AND FORMULATION

In another embodiment, the present invention provides a novel pharmaceutical composition comprising a pharmaceutically acceptable carrier and a therapeutically effective amount of a compound of formula (I) or (II) or a pharmaceutically acceptable salt form thereof.

The cyclic dependent kinase inhibitor compounds of this invention can be administered as treatment for cancer or proliferative diseases by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets, suppositories and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers and administration forms, as well as their methods of manufacture are described in Remington's Pharmaceutical Sciences, 18th ed., Mack Publishing Company, Easton, Pa., 1990, a standard reference text in this field, the disclosure of which is hereby incorporated by reference.

SYNTHESIS

The compounds of the present invention can be synthesized using the methods described below, and/or with synthetic methods known in the art of synthetic organic chemistry, or variations thereon as appreciated by those skilled in the art. Each of the references cited below are hereby incorporated herein by reference.

Key intermediates preparing the compounds of the present invention are pyrazole aminonitriles, aminocarboxamides, and aminoesters of the formulas II, III, and IV, respectively. The preparation of these intermediates is has precedence in the chemical literature, and several methods are summarized in Schemes A (A. O. Abdelhamid, A. S. Shawali, et al. J. Heterocycl. Chem., 1984, 21, 1049.); B (C. C. Cheng and R. K. Robins, J. Org. Chem. 1956, 21, 1240.); C (P. Schmidt and J. Druey, Helv. Chem. Acta, 1956, 39, 986.); and D (Tominaga et al., J. Heterocycl. Chem., 1990, 27, 775). A wide variety of starting hydrazines and aldehydes are commercially available or can be prepared by standard organic transformations. The substituents in the following schemes, which are designated $R^1$, $R^2$, and Q, have the same definition as that defined above in the Detailed Description.

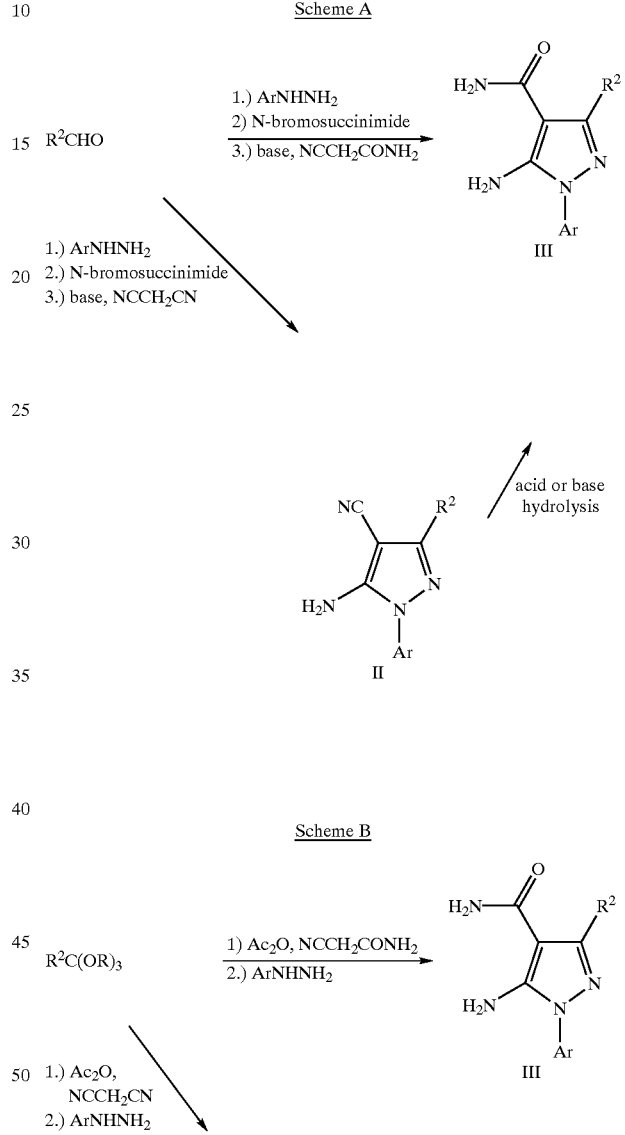

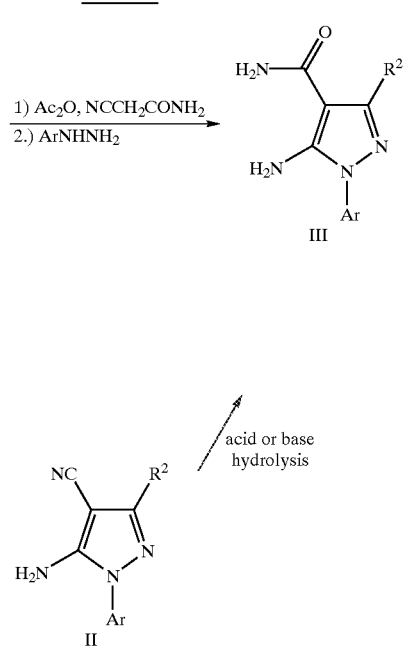

Scheme C

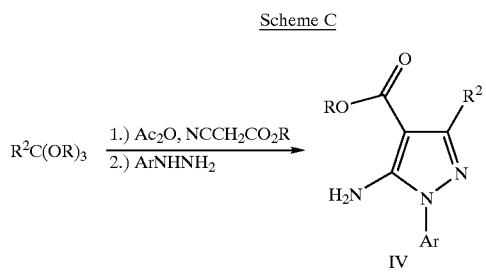

Scheme D

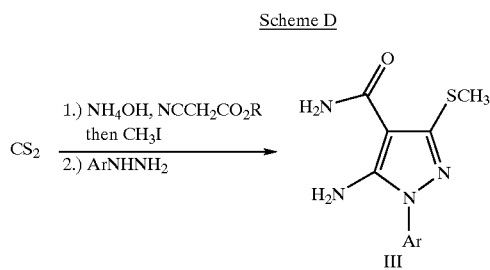

Aminonitriles of the formula II can be converted to pyrazolo[3,4-d]pyrimidines of the present invention as shown in Scheme E. In summary, the aminocarboxamide is acylated, optionally in the presence of a suitable solvent such as dichloromethane by treatment with a suitable base such as triethylamine followed by an acid halide of the formula $R^1CHQCOX$, preferably an acid chloride to give carboxamidonitriles of the formula V. Alternately carboxamidonitriles of the formula V can be prepared by coupling of aminonitriles II with carboxylic acids of the general formula $R^1CHQCO_2H$ in the presence of a suitable base and coupling reagent in a suitable solvent. The coupling of amines and carboxylic acids has been reviewed (Klausnew and Bodansky Synthesis, 1972, 453–463), and the variety of reagents available for effecting it can be appreciated by those skilled in the art.

Transformation of carboxamidonitriles of the formula V to the compounds of the present invention can be accomplished by treatment with an excess of hydrogen peroxide in the presence of a suitable base, preferably a metal hydroxide or alkoxide base in a solvent, preferably water, an alcohol, or a water-alcohol mixture at a temperature in the range of about 0° C. up to 100° C.

Scheme E

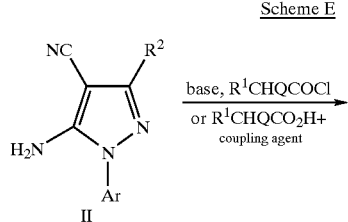

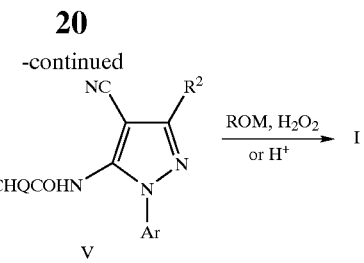

Alternatively, carboxamidonitriles of the formula V can be transformed to the compounds of the present invention by heating, preferably for about an hour in concentrated, strong acid, preferably 85% $H_3PO_4$.

Scheme F shows an alternative means for preparing the compounds of the present invention. Amino carboximides of the formula III in a suitable solvent, preferably a lower alkanol, are treated with an excess of an ester of the formula $R^1CHQCO_2R$, where R is lower alkyl and an excess of a base, preferably a metal lower alkoxide, preferably at the boiling point of the solvent to give compounds of the present invention. Many arylacetic esters are commercialy available or can be prepared in one step from commercially available arylacetic acids by esterification with an excess of an alcohol, ROH, preferably at reflux with ethyl or methyl alcohol, used as solvent in the presence of an acid catalyst such as $H_2SO_4$ or p-TsOH. Alternatively, a coupling reagent such as DCC can be used, preferably in a solvent such as $CH_2Cl_2$ with a catalylst such as DMAP. Phenylacetic acids may be prepared by acid or base hydrolysis of arylacetonitriles which in turn may be prepared by treatment of aryl halides with $CN^-$, preferably in solvents such as DMF, MeOH, EtOH, water, DMSO, or mixtures thereof. Further examples of arylacetic esters may be prepared from aryl carboxylic acids under Arndt-Eistert (Meier and Zeller Angew. Chem. Int. Ed. Engl. 1975, 14, 32–43) or related homologation conditions.

Scheme F

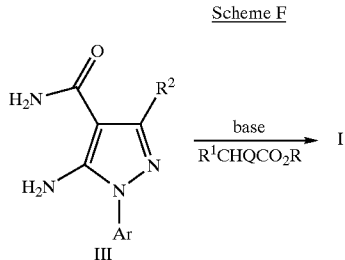

Wherein I represents compounds of formula I.

Aminoesters of the formula IV can be converted to compounds of the present invention by reaction with an excess of a nitrile of the formula $R^1CHQCN$ and sodium. This reaction is preferably performed neat with heating.

Scheme G

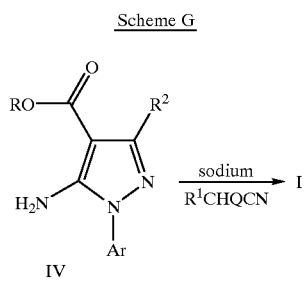

Wherein I represents compounds of formula I

Pyrazolo[3,4-d]pyrimidin-4-ones may be further elaborated as described below to give additional compounds of the present invention. Electrophilic aromatic substitution reactions can be performed on the $R^1$ aryl or heteroaryl group to introduce substituents. Such reactions include, but are not limited to nitration, acylation (Friedel-Crafts), halogenation, alkylation (Friedel-Crafts), chloromethylation, sulfonation, and aminomethylation (Mannich reaction). Conditions for performing these reactions are familiar to those skilled in the art of organic synthesis, generally involving reaction of the electrophile with the aryl or heteroaryl substrate in the presence of a catalyst. In the case of nitrations or Mannich reactions, the catalyst is preferably a protic acid which may serve as solvent, where the electrophile is generated in situ from saltpeter, or an amine and a carbonyl component, respectively. For other electrophilic aromatic substitution reactions, preferred catalysts are Lewis acids, including but not limited to $FeX_3$, $AlX_3$, and $ZnX_2$, where X is halogen.

The compounds prepared above which have an amino group can be derivatized by reaction with electrophiles including, but not limited to acyl halides, anhydrides, isocyanates, chloroformates, sulfonyl halides, alkyl halides, lactones, or esters. Conditions for performing these addition reactions are familiar to those skilled in the art of organic synthesis, generally involving addition of the electrophile to the nucleophile, preferably in solution at a temperature between 0° C. and RT. Addition of a base may be necessary. It should be noted that the products of these reactions can react further with some electrophiles at the pyrimidinone nitrogen (N5). The resulting functional groups (amides, carbamates, etc.) are less stable to basic hydrolysis than the desired anilino- or aliphatic groups and can be cleaved back to the pyrimidinone having H on N5. Reaction of compounds bearing an amine group with agents such as haloacyl halides, α,β-unsaturated acid halides, or halosulfonyl halides gives intermediates which can react with nucleophiles such as primary or secondary amines, diamines, alkoxides, aminoalcohols or thiols.

The compounds prepared above, which have a carboxyl group, can be derivatized by activation and reaction with nucleophiles including, but not limited to amines and alcohols to give, respectively, amides and esters. The coupling of amines and carboxylic acids with carbodiimides has been reviewed (Klausnew and Bodansky Synthesis, 1972, 453–463), and the variety of additional reagents available for effecting it as well as the potential need for protecting groups (Green and Wuts "Protective Groups in Organic Synthesis" Second Edition, John Wiley & Sons, 1991) to mask reactive functionality can be appreciated by those skilled in the art. The preparation of esters from acids has been described above. Reduction of these amides and esters to amines and alcohols can be performed using a suitable hydride reducing agent.

The compounds prepared above which have an amino group can be derivatized by conversion to an electrophilic species by activation with phosgene or a phosgene equivalent (Tetrahedron: Asymmetry 1995, 6, 745; J. Org. Chem. 1994, 59, 1937.), preferably in the presence of a base, and reaction with nucleophiles including, but not limited to amines, alcohols, and sulfonamides to give, respectively, ureas, carbamates, and sulfonylureas. Conditions for performing these reactions and the hazards associated with handling phosgene and phosgene equivalents are familiar to those skilled in the art of organic synthesis, and all appropriate precautions should be taken.

Further transformations which may be required to prepare compounds of the present invention include reductions of ketones, aldehydes, esters, acids, amides or reductive aminations by alumino- and borohydride reagents (J. Seyden-Penne "Reductions by the Alumino and Borohydrides in Organic Synthesis" VCH Publishers, Inc., 1991) and oxidations of groups including but not limited to alcohols, aldehydes, olefins, thioethers, sulfoxides, and heteroaryl groups (Milos Hudlicky "Oxidations in Organic Chemistry" American Chemical Society, 1990). Reduction of functional groups such as alkenes, alkynes, nitrogen, nitro- or cyano-groups could be accomplished by catalytic hydrogenation or by dissolving metal reduction. Further elaboration of intermediates containing electrophilic sites to compounds of the present invention could be accomplished by displacement with nucleophiles including, but not limited to, $CN^-$, amines, alkoxides, mercaptans, or carbanions. Still other compounds of the present invention could be prepared by coupling of aryl halides, triflates, or stannames with the appropriate boronic acids (Stilk, J. K. Angew. Chem. Int. Ed. Engl. 1986, 25, 508; Suzuki, A. Pure Appl. Chem. 1985, 57, 1749). The compounds prepared above, which have a carbonyl group, can be derivatized further by reaction with nucleophiles to give secondary alcohols. Such nucleophiles include, but are not limited to, Grignard reagents, alkyl-, alkenyl-, and alkynyl-lithium reagents, and allyl-stannanes, silanes, and the like. Compounds prepared as described above could be further elaborated by rearrangements such as the Beckmann (Gawley in Org. React. 1988, 35, 1–420) or other rearrangements.

Further elaboration of the compounds prepared above can be accomplished by generation of an organomagnesium organolithium species by directed metallation (Beak and Meyers Acc. Chem. Res. 1986, 19, 356–363; Beak and Snieckus Acc. Chem. Res. 1982, 15, 306–312; Katritzky, Lam, and Sengupta Prog. Heterocycl. Chem. 1989, 1, 1–29) or from an aryl halide by lithium-halogen exchange (Parham and Bradsher, Acc. Chem. Res. 1982, 15, 300–305).

Other features of the invention will become apparent in the course of the following descriptions of exemplary embodiments that are given for illustration of the invention and are not intended to be limiting thereof.

EXAMPLES

Abbreviations used in the Examples are defined as follows: "° C." for degrees Celsius, "MS or mass spec." for mass spectrum, "g" for gram or grams, "h" for hour or hours, "mg" for milligram or milligrams, "mL" for milliliter or milliliters, "mmol" for millimoles, "M" for molar, "min" for minute or minutes, "DMF" for dimethylformamide, "THF" for tetrahydrofuran, "Boc" for t-butoxycarbonyl, "Bop" for (benzotriazol-1-yloxy)tris(dimethylamino)-phosphonium hexafluorophosphate, "EDC" for 1-(3-dimethylaminopropyl)-3-ethylcarbodiimide hydrochloride, "BopCl" for bis(2-oxo-3-oxazolidinyl)phosphinic chloride, "ether" for diethyl ether, "aq" for aqueous, "RT" for ambient temperature, "HOAc" for acetic acid, "EtOAc" for ethyl acetate "p-TsOH" for para-toluenesulfonic acid, "DIEA" for N,N-diisopropylethylamine, "t-BuOH" for t-butanol, "EtOH" for ethanol, "MeOH" for methanol, "NBS" for N-bromosuccinimide, and "TFA" for trifluoroacetic acid. "Mass spec." results refer to M/z for the product species composed entirely of the most prevalent isotopes of each of its constituent atoms, i.e. 12 for carbon, 1 for hydrogen, 35 for Cl, 14 for N, and 16 for O. Ionization techniques used give $M^+$, $(M+H)^+$, or $(M-H)^-$ species. Proton ($^1H$) nuclear magnetic resonance(NMR) experiments were performed on dilute solutions in the solvent indicated at the frequency (generally 300 MHz) indicated. Chemical shifts are reported in ppm downfield from tetramethylsilane. The following abbreviations are used: "s" for singlet, "d" for doublet, "t" for triplet, "q" for quartet, "m" for multiplet, and "br." for broad. Reported integrations are approximate. It is understood by those experienced in the interpretation of NMR spectra that some proton signals are absent, increased or diminished in measured intensity in a given spectrum due to factors such as poor instrument phase, rapid exchange with trace water or protons in the solvent, or because they resonate at a frequency outside that recorded (generally −0.2 to +15 ppm). It is also understood that chemical shifts for a given compound may vary due to factors such as concentation or pH of the sample. It is further understood that due to the precision in measurement of coupling constants, signals for coupled protons may have coupling constants that differ slightly.

Example 1

1-(2,4,6-Trichlorophenyl)-3-(methylthio)-6-(3-methoxybenzyl)pyrazolo[3,4-d]pyrimidin-4-one To a stirred solution of 176 mg (0.5 mmol) of 5-amino-3-(methylthio)-1-(2,4,6-trichlorophenyl)pyrazole-4-carboxamide in 6 mL of absolute ethanol was added 550 mg (3.0 mmol) of 3-methoxyphenylacetyl chloride followed by 2.3 mL (6.0 mmol) of 2.66 M sodium ethoxide in ethanol. The solution was stirred 18 h at reflux, and the heating mantle was then removed. The reaction was treated with 5 mL of 10% aq. HOAc, cooled to ambient temperature, and filtered. The filtrate was washed with 6 mL of 1:1 water-methanol then 6 mL of 1:1 ether-hexanes. The off-white solid was briefly air-dried to give 220 mg (92%) of 1-(2,4, 6-trichlorophenyl)-3-(methylthio)-6-(3-methoxybenzyl)pyrazolo[3,4-d]pyrimidin-4-one, mp 245–248° C. Mass spec. Calc'd for $C_{20}H_{16}N_4O_2SCl_3$: 481.0060. Found: 481.0076 $(M+H)^+$.

Example 2

1-(2,4,6-Trichlorophenyl)-3-(methylthio)-6-(3-hydroxybenzyl)pyrazolo[3,4-d]pyrimidin-4-one To a stirred solution of 55 mg (0.11 mmol) of 1-(2,4,6-trichlorophenyl)-3-(methylthio)-6-(3-methoxybenzyl)pyrazolo[3,4-d]pyrimidin-4-one in 2 mL of $CH_2Cl_2$ was added 1 mL (1 mmol) of 1 M boron tribromide in $CH_2Cl_2$. The solution was stirred 35 min. at ambient temperature, and it was then cooled to 0° C. The reaction was quenched with 4 mL of 1 M aq. HCl. The mixture was poured into water and extracted with EtOAc. The organic extract was washed with brine, dried ($MgSO_4$), and concentrated under reduced pressure to afford 52 mg (98%) of 1-(2,4,6-trichlorophenyl)-3-(methylthio)-6-(3-hydroxybenzyl)pyrazolo[3,4-d]pyrimidin-4-one as an off-white solid, m.p. 264–266° C. Mass spec. Calc'd for $C_{19}H_{13}N_4O_2SCl_3$: 465.9825$(M)^+$. Found: 465.9798.

Starting from 5-amino-3-(methylthio)-1-(2,4,6-trichlorophenyl)pyrazole-4-carboxamide, the following compounds were prepared by methods similiar to those used to synthesize the compounds above:

TABLE I

| Ex. # | $R^1$ | m.p. (° C.) | MS |
|---|---|---|---|
| 3 | phenyl | 234–238 | |
| 4 | imidazol-4-yl | | 441 |
| 5 | 4-pyridyl | 283–287 | 452 |
| 6 | 3,4-dimethoxyphenyl | 226–230 | 511 |
| 7 | 3-nitrophenyl | 243–255 | 496 |
| 8 | 4-methoxyphenyl | 263–267 | |
| 9 | 4-hydroxyphenyl | 294–296 | 467 |
| 10 | 2,5-dimethoxyphenyl | 137–150 | 481 |
| 11 | 2,5-dihydroxyphenyl | | 483 |
| 12 | 4-aminophenyl | | 466 |
| 13 | 3,4-methylenedioxyphenyl | 257–260 | |
| 14 | 2-thienyl | 218–222 | 457 |

Example 15

1-(2,4,6-Trichlorophenyl)-3-ethyl-6-(3-methoxybenzyl)pyrazolo[3,4-d]pyrimidin-4-one Part A: To a stirred solution of 320 mg (1.9 mmol) of 2-cyano-3-ethoxypentenamide in 7 mL of MeOH was added 465 mg (2.2 mmol) of 2,4,6-trichlorophenylhydrazine. The solution was stirred 3 h at reflux, treated with 2 mL of water, and allowed to stir an additional 1 h, cooling to RT. The white solid which precipitated was filtered, washed with 2:1 MeOH-water, and air-dried to afford 520 mg (82%) of 5-amino-3-ethyl-1-(2,4,6-trichlorophenyl) pyrazole-4-carboxamide, mp 186–188° C., Mass Spec(CI+): 331.9989 $(M)^+$.

Part B: To a stirred solution of 167 mg (0.5 mmol) of 5-amino-3-ethyl-1-(2,4,6-trichlorophenyl)pyrazole-4-carboxamide in 6 mL of absolute ethanol was added 550 mg (3.0 mmol) of 3-methoxyphenylacetyl chloride followed by 2.3 mL (6.0 mmol) of 2.66 M sodium ethoxide in ethanol. The solution was stirred 18 h at reflux, and the heating mantle was then removed. The reaction was treated with 5 mL of 10% aq. HOAC, cooled to ambient temperature, and filtered. The filtrate was washed with 6 mL of 1:1 water-methanol then 6 mL of 1:1 ether-hexanes. The off-white solid was briefly air-dried to give 170 mg (76%) of 1-(2,4, 6-trichlorophenyl)-3-ethyl-6-(3-methoxybenzyl)pyrazolo[3, 4-d]pyrimidin-4-one, mp 235–238° C. Mass Spec. 463$(M+H)^+$.

Example 16

1-(2,4,6-Trichlorophenyl)-3-ethyl-6-(3-hydroxybenzyl)pyrazolo[3,4-d]pyrimidin-4-one To a stirred solution of 80 mg (0.17 mmol) of 1-(2,4,6-trichlorophenyl)-3-ethyl-6-(3-methoxybenzyl)pyrazolo[3,4- d]pyrimidin-4-one in 1 mL of $CH_2Cl_2$ was added 1 mL (1 mmol) of 1 M boron tribromide in $CH_2Cl_2$. The solution was stirred 1 h at ambient temperature and then cooled to 0° C. The reaction was quenched with 4 mL of 1 M aq. HCl. The mixture was poured into water and extracted with 1:1 tetrahydrofuran-EtOAc. The organic extract was washed with brine, dried ($MgSO_4$), and concentrated under reduced pressure to afford 77 mg (100%) of 1-(2,4,6-trichlorophenyl)-3-ethyl-6-(3-hydroxybenzyl)pyrazolo[3,4-d]pyrimidin-4-one as an off-white solid. Mass Spec.: 449 $(M+H)^+$.

Example 17

1-(2,4,6-Trichlorophenyl)-3-ethyl-6-(4-(4-methoxyhenyl)benzyl))pyrazolo[3,4-d]pyrimidin-4-one To a stirred mixture of 100 mg (0.2 mmol) of 1-(2,4,6-trichlorophenyl)-3-ethyl-6-(4-bromobenzyl)pyrazolo[3,4-d] pyrimidin-4-one and 38 mg (0.25 mmol) of 4-methoxyphenylboronic acid in 10 mL of toluene, 0.5 mL of EtOH, and 2 mL of 2 M $Na_2CO_3$ was added to 5 mg of $Pd(Ph_3P)_4$. The mixture was heated to reflux overnight, poured into water, and extracted with $CHCl_3$. The organic extract was dried ($MgSO_4$), filtered through celite, chromatographed (elution with 5% $MeOH/CH_2Cl_2$), and recrystallized to afford 64 mg (59%) of 1-(2,4,6-trichlorophenyl)-3-ethyl-6-(4-(4-methoxyphenyl)benzyl) pyrazolo[3,4-d] pyrimidin-4-one as a pale brown powder, mp 275–277° C., Mass spec.: 537 $(M-H)^-$.

Starting from 5-amino-3-ethyl-1-(2,4,6-trichlorophenyl) pyrazole-4-carboxamide the following compounds were prepared by methods similiar to those used to synthesize the compounds above:

TABLE II

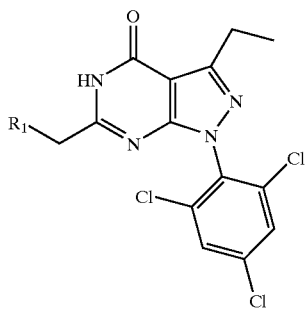

| Ex. # | $R^1$ | m.p. (° C.) | MS |
|---|---|---|---|
| 18 | 3-indolyl | 296–299 | 474 |
| 19 | 3-hydroxy-4-methylphenyl | amorphous | |
| 20 | 3-methoxy-4-methylphenyl | 263–265 | |
| 21 | 4-hydroxy-3-methylphenyl | 260–263 | |
| 22 | 4-methoxy-3-methylphenyl | 245–247 | 479 |
| 23 | phenyl | 240–241 | 431 |
| 24 | 3,4,5-trimethoxyphenyl | 224–226 | 523 |
| 25 | 4-bromophenyl | 296–299 | 511 |
| 26 | 4-hydroxy-3-nitrophenyl | 263–266 | |
| 27 | 2-methoxyphenyl | 188–191 | 463 |
| 28 | 4-pyridyl | 277–280 | 432 |
| 29 | 3-amino-2-methylphenyl | 242–243 | |
| 30 | 3,4-dimethoxyphenyl | 220–222 | 493 |
| 31 | 3,4-dihydroxyphenyl | | 465 |
| 32 | 2-pyridyl 'HOAc | 164–169 | 433 |
| 33 | 4-hydroxy-3-methoxyphenyl | 260–280 | 479 |
| 34 | 4-methoxyphenyl | 261–262 | 463 |
| 35 | 4-hydroxyphenyl | 289–291 | 449 |

TABLE II-continued

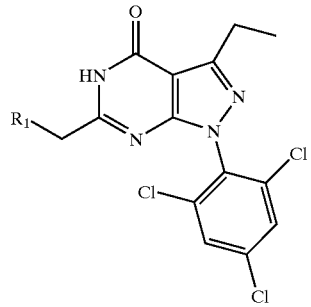

| Ex. # | $R^1$ | m.p. (° C.) | MS |
|---|---|---|---|
| 36 | 3-hydroxy-4-methoxyphenyl | 237–240 | 479 |
| 37 | 3-aminophenyl | 236–240 | 447.0418 |
| 38 | 4-aminophenyl | 256–259 | 448 |
| 39 | 3-methylphenyl | 238–240 | |
| 40 | 5-methoxy-3-indolyl | 295–298 | |
| 41 | 3-amino-4-hydroxyphenyl | amorphous | 464 |
| 42 | 3,4-dimethoxy-6-hydroxy-methylphenyl | 203–205 | |
| 43 | 3-(dimethylaminoinethyl)phenyl HCl salt | amorphous | 492 |
| 44 | 4-amino-3-nitrophenyl | amorphous | 491 |
| 45 | 4-(dimethylamino)phenyl | | 476 |
| 46 | 3-(ethoxycarbonylmethyl)phenyl | 168–169 | 517 |
| 47 | 3-(carboxymethyl)phenyl | 192–194 | |

Example 48

1-(2,4,6-Trichlorophenyl)-3-isopropyl-6-(3-methoxybenzyl)pyrazolo[3,4-d]pyrimidin-4-one Part A: To a stirred solution of 106 g (500 mmol) of 2,4,6-trichlorophenyl hydrazine in 600 mL of absolute ethanol was added 48.1 mL (530 mmol) of isobutyraldehyde. The solution was stirred 2 h at RT and concentrated under reduced pressure to afford an oil. The crude oil was dissolved in 450 mL of dry DMF and cooled to 0° C. This solution was treated with 94.3 g (530 mmol) of NBS in four portions over 10 min. The solution was stirred 1 h at 0° C. and poured onto ice. The mixture was diluted with water and extracted with 800 mL of ether. The organic extract was washed twice with water and once with brine, dried ($MgSO_4$), and concentrated under reduced pressure to afford an oil. In a separate flask, 44.3 g (670 mmol) of malononitrile in 140 mL of EtOH was cooled to 0° C. and treated with 252 mL (670 mmol) of 2.66 M NaOEt in EtOH over 6 min. This solution was added in four portions over 5 min. to a rapidly stirred solution of the crude bromohydrazone in 350 mL of absolute EtOH. Using a heat pistol, this solution was maintained at reflux for 10 min. further. The reaction was cooled, quenched with 5% aq. HOAc, and extracted twice with ether. The combined organic extracts were washed (brine), dried ($MgSO_4$) and filtered over activated charcoal and celite, and concentrated under reduced pressure. The product was chromatographed on silica gel (gradient elution with 1:3 ether-hexanes and 2:1 ether-$CH_2Cl_2$) to afford 93.5 g (57%) of 5-amino-4-cyano-3-isopropyl-1-(2,4,6-trichlorophenyl)pyrazole as a white solid. $^1H$ NMR($CDCl_3$, 300 MHz) δ 7.51(s, 2H); 4.28(br. s, 2H); 3.05(septet, 1H, J=7.0 Hz); 1.36(d, 6H, J=7.0 Hz).

Part B: Thirty grams (91.0 mmol) of 5-amino-4-cyano-3-isopropyl-1-(2,4,6-trichlorophenyl)pyrazole was dissolved in 80 mL of con. $H_2SO_4$ and stirred 24 h at RT. The solution was added to cold aqueous NaOH, and the resulting precipitate was filtered, washed with water, and dried under vacuum to give 29.1 g (92%) of 5-amino-3-isopropyl-1-(2,4,6-trichlorophenyl)pyrazole-4-carboxamide as a white solid. $^1$H NMR (CDCl$_3$, 300 MHz) δ 7.49(s, 2H); 5.06–5.63 (m, 4H); 3.06(septet, 1H, J=6.8 Hz); 1.39(d, 6H, J=6.9 Hz).

Part C: To a stirred solution of 167 mg (0.5 mmol) of 5-amino-3-isopropyl-1-(2,4,6-trichlorophenyl)pyrazole-4-carboxamide in 6 mL of absolute ethanol was added 550 mg (3.0 mmol) of 3-methoxyphenylacetyl chloride followed by 2.3 mL (6.0 mmol) of 2.66 M sodium ethoxide in ethanol. The solution was stirred 18 h at reflux, and the heating mantle was then removed. The reaction was treated with 5 mL of 10% aq. HOAc, cooled to ambient temperature, and filtered. The filtrate was washed with 6 mL of 1:1 water-methanol then 6 mL of 1:1 ether-hexanes. The off-white solid was briefly air-dried to give 170 mg (76%) of 1-(2,4,6-trichlorophenyl)-3-isopropyl-6-(3-methoxybenzyl)pyrazolo[3,4-d]pyrimidin-4-one, mp 204–205° C., Mass Spec: 477(M+H)$^+$.

Example 49

1-(2,4,6-Trichlorophenyl)-3-isopropyl-6-(3-hydroxybenzyl)pyrazolo[3,4-d]pyrimidin-4-one To a stirred solution of 65 mg (0.14 mmol) of 1-(2,4,6-trichlorophenyl)-3-isopropyl-6-(3-methoxybenzyl)pyrazolo[3,4-d]pyrimidin-4-one in 1 mL of CH$_2$Cl$_2$ was added 1 mL(1 mmol) of 1 M boron tribromide in CH$_2$Cl$_2$. The solution was stirred 1 h at ambient temperature and then cooled to 0° C. The reaction was quenched with 4 mL of 1 M aq. HCl. The mixture was poured into water and extracted with 1:1 THF-EtOAc. The organic extract was washed with brine, dried (MgSO$_4$), and concentrated under reduced pressure to afford 63 mg (100%) of 1-(2,4,6-trichlorophenyl)-3-isopropyl-6-(3-hydroxybenzyl)pyrazolo[3,4-d]pyrimidin-4-one as an amorphous solid. $^1$H NMR (300 MHz, DMSO) δ 12.46(br. s, 1H); 9.33(br. s, 1H); 7.96(s, 2H); 7.03(t, 1H, J=7.7 Hz); 6.55–7.08(m, 3H); 3.75(s, 2H); 3.19–3.36(m, 1H); 1.29(d, 6H, J=7.0 Hz).

Starting from 5-amino-3-isopropyl-1-(2,4,6 trichlorophenyl)pyrazole-4-carboxamide the following compounds were prepared by methods similiar to those used to synthesize the examples above:

TABLE III

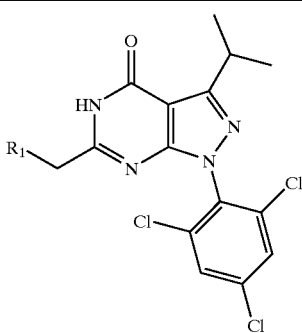

| Ex. # | R$^1$ | m.p. (° C.) | MS |
|---|---|---|---|
| 50 | 3-hydroxy-4-methoxyphenyl | | 491 |
| 51 | 3-aminophenyl | | 462 |
| 52 | 4-aminophenyl | 223–225 | 462 |
| 53 | 4-methoxyphenyl | | 475 |
| 54 | 4-amino-3-methoxyphenyl | 238–240 | |

TABLE III-continued

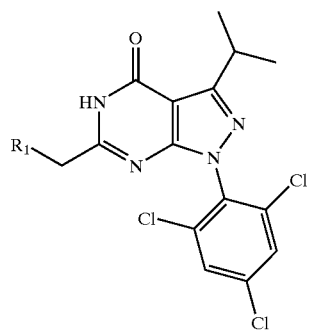

| Ex. # | R$^1$ | m.p. (° C.) | MS |
|---|---|---|---|
| 55 | 4-amino-3-hydroxyphenyl | 210–217 (dec.) | 476 |
| 56 | 4-(dimethylaminomethyl)phenyl HCl salt | 278–281 (dec.) | |
| 57 | 5-methoxy-2-methylindol-3-yl | | 528 |
| 58 | 5-hydroxy-2-methylindol-3-yl | | 514 |
| 59 | 4-bromophenyl | 229–230 | |
| 60 | 2-pyridyl | 214–215 | 448.0506 |
| 61 | 4-pyridyl | 273–275 | 448.0502 |
| 62 | 4-methylphenyl | 205–206 | 461.0696 |
| 63 | 2-methylphenyl | 194–195 | 461.0700 |
| 64 | 3-pyridyl | 214–215 | 448.0506 |
| 65 | 4-methyl-3-pyridyl | 225–227 | |
| 66 | 3-amino-2-methylphenyl | | 474 |
| 67 | 4-(methylamino)phenyl | 244–246 | 476 |
| 68 | 2H-1,4-benzoxazin-3-on-7-yl | | 516 |
| 69 | 4-chloro-3-pyridyl | 245–248 | 480 |

Example 70

1-(2,4,6-Trichlorophenyl)-3-cyclopropyl-6-(3-hydroxy-4-methoxybenzyl)pyrazolo[3,4-d]pyrimidin-4-one To a stirred solution of 146 mg (0.42 mmol) of 5-amino-3-cyclopropyl-1-(2,4,6-trichlorophenyl)pyrazole-4-carboxamide in 6 mL of absolute ethanol was added 533 mg (2.53 mmol) of ethyl 3-hydroxy-4-methoxyphenylacetate followed by 1.91 mL (5.1 mmol) of 2.66 M sodium ethoxide in ethanol. The solution was stirred 18 h at reflux, and the heating mantle was then removed. The reaction was treated with 5 mL of 10% aq. HOAc, cooled to ambient temperature, and filtered. The filtrate was washed with 6 mL of 1:1 water-methanol then 6 mL of 1:1 ether-hexanes. The off-white solid was briefly air-dried to give 46 mg (22%) of 1-(2,4,6-trichlorophenyl)-3-cyclopropyl-6-(3-hydroxy-4-methoxybenzyl)pyrazolo[3,4-d]pyrimidin-4-one. Mass Spec.: 489 (M–H)$^-$.

Starting from 5-amino-3-cyclopropyl-1-(2,4,6-trichlorophenyl)pyrazole-4-carboxamide the following compounds were prepared by methods similiar to those used to synthesize the examples above:

TABLE IV

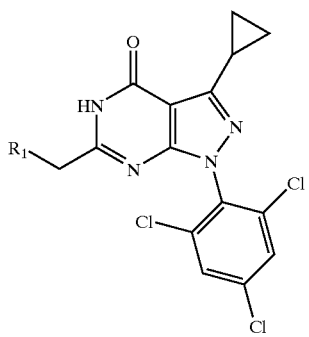

| Ex. # | R¹ | m.p. (° C.) | MS |
|---|---|---|---|
| 71 | Indazol-4-yl | | 483 |
| 72 | Indazol-5-yl | 274–283 | 483 |
| 73 | Indazol-6-yl | | 483 |
| 74 | 4-Aminophenyl | | 460 |
| 75 | Benzoxazol-2-on-5-yl | | 500 |
| 76 | 3-Hydroxy-4-nitrophenyl | 259–260 | 506 |
| 77 | 4-(N,N-dimethylglycinamido)phenyl | 250–253 | |

Example 78

1-(2,4,6-Trichlorophenyl)-3-trifluoromethyl-6-(3-methoxybenzyl)pyrazolo[3,4-d]pyrimidin-4-one To a stirred solution of 186 mg (0.50 mmol) of 5-amino-3-trifluoromethyl-1-(2,4,6-trichlorophenyl)pyrazole-4-carboxamide in 6 mL of absolute ethanol was added 555 mg (3.0 mmol) of 3-methoxyphenylacetyl chloride followed by 2.26 mL (6.0 mmol) of 2.66 M sodium ethoxide in ethanol. The solution was stirred 23 h at reflux, and the heating mantle was then removed. The reaction was treated with 10 mL of 10% aq. HOAc, cooled to ambient temperature, and filtered. The filtrate was washed with 6 mL of 1:1 water-methanol then 6 mL of 1:3 ether-hexanes. The off-white solid was briefly air-dried to give 230 mg (91%) of 1-(2,4,6-trichlorophenyl)-3-trifluoromethyl-6-(3-methoxybenzyl)pyrazolo[3,4-d]pyrimidin-4-one. Mass spec.: 503(M+H)⁺.

Example 79

1-(2,4,6-Trichlorophenyl)-3-trifluoromethyl-6-(3-hydroxybenzyl)pyrazolo[3.4-d]pyrimidin-4-one To a stirred solution of 60 mg (0.12 mmol) of 1-(2,4,6-trichlorophenyl)-3-trifluoromethyl-6-(3-methoxy-4-methoxybenzyl)pyrazolo[3,4-d]pyrimidin-4-one in 2 mL of $CH_2Cl_2$ was added 2 mL of a 1M solution of $BBr_3$ in $CH_2Cl_2$. The solution was stirred 2.5 h at RT and quenched with 1 N aq. HCl. The mixture was diluted with water and extracted with EtOAc. The organic extract was washed with brine, dried ($MgSO_4$), and concentrated under reduced pressure. The crude product was chromatographed on silica gel (elution with 1:1 hexanes-THF, then THF) to afford 1-(2,4,6-trichlorophenyl)-3-trifluoromethyl-6-(3-hydroxybenzyl)pyrazolo[3,4-d]pyrimidin-4-one, as an off-white solid. Mass spec.: 487(M–H)⁻.

Starting from 5-amino-3-(trifluoromethyl)-1-(2,4,6-trichlorophenyl)pyrazole-4-carboxamide the following compounds were prepared by methods similiar to those used to synthesize the compounds above:

TABLE V

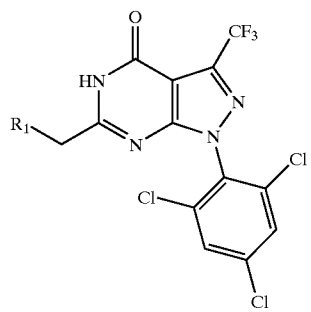

| Ex. # | R¹ | m.p. (° C.) | MS |
|---|---|---|---|
| 80 | 3-aminophenyl | | 488 |
| 81 | 4-aminophenyl | | 488 |
| 82 | 4-methoxyphenyl | 263–265 | 501 |
| 83 | 4-hydroxyphenyl | | 487 |
| 84 | 4-pyridyl | | 474 |
| 85 | 3-hydroxy-4-methoxyphenyl | | 517 |
| 86 | 4-hydroxy-3-methoxyphenyl | | 517 |

Example 87

1-(2,4,6-Trichlorophenyl)-3-isopropyl-6-(3-(N,N-dimethylglycinamido)-2-methylbenzyl)pyrazolo[3,4-d]pyrimidin-4-one Part A: To a stirred, cooled (0° C.) solution of 110 mg (0.23 mmol) of 1-(2,4,6-trichlorophenyl)-3-isopropyl-6-(3-amino-2-methylbenzyl)pyrazolo[3,4-d]pyrimidin-4-one in 4 mL of THF was added 0.084 mL (0.6 mmol) of triethylamine followed by 0.024 mL (0.3 mmol) of chloroacetyl chloride. The solution was stirred 2 h, warming to ambient temperature. The reaction was quenched by dropwise addition of 5 mL of 0.5 N aq. HCl, and the resulting solid was collected by filtration. The product was washed with water then 1:1 ether-hexanes and air-dried to afford 96 mg (76%) of 1-(2,4,6-trichlorophenyl)-3-isopropyl-6-(3-(chloroacetamido)-2-methyl benzyl)pyrazolo[3,4-d]pyrimidin-4-one, mp 237–238° C. ¹H NMR (300 MHz, DMSO) δ 12.42(s, 1H); 9.69(s, 1H); 7.93(s, 2H); 7.15(d, 1H, J=7.3 Hz); 7.07(t, 1H, J=7.7 Hz); 6.95(d, 1H, J=8.7 Hz); 4.25(s, 2H); 3.90(s, 2H); 3.20–3.33(m, 1H); 2.07(s, 3H); 1.30(d, 6H, J=6.9 Hz).

Part B: To a stirred solution of of 1-(2,4,6-trichlorophenyl)-3-isopropyl-6-(3-(chloroacetamido)-2-methylbenzyl)pyrazolo[3,4-d]pyrimidin-4-one in 2 mL of THF was added 1 mL of 40% aq. dimethylamine. The solution was stirred overnight at ambient temperature and treated with water until a precipitate formed. The precipitate was filtered, washed with water and 1:1 ether-hexanes, and air-dried to afford 46 mg (75%) of 1-(2,4,6-trichlorophenyl)-3-isopropyl-6-(3-(N,N-dimethylglycinamido)-2-methylbenzyl)pyrazolo[3,4-d]pyrimidin-4-one as an off-white solid, mp 219–222° C. Mass spec. (ESI–): 561((M–H)⁺). By allowing m-substituted anilines to react with suitable acylating agents and performing further synthetic manipulations as necessary, the following compounds wherein R¹=phenyl were prepared by methods similiar to those used to synthesize the compounds above:

TABLE VI

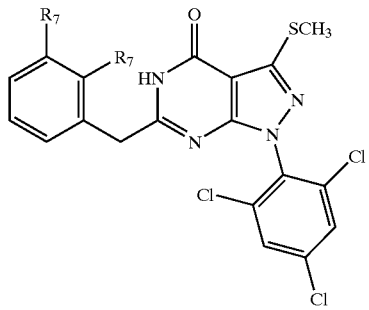

| Ex. # | R² | R⁷ (meta) | R⁷ (ortho) | mp (° C.) | MS |
|---|---|---|---|---|---|
| 88 | Et | CH₃SO₂NH | H | | 524 |
| 89 | i-Pr | CH₃SO₂NH | H | | 538 |
| 90 | i-Pr | CF₃HCONH | H | | 538 |
| 91 | i-Pr | CH₃CONH | H | | 502 |
| 92 | i-Pr | CH₃NHCONH | H | | 517 |
| 93 | i-Pr | HOCH₂CH₂NHCONH | H | | 547 |
| 94 | i-Pr | HO(CH₂)₄NHCONH | H | | 577 |
| 95 | i-Pr | (Fluorophen-4-yl)CH₂NHCONH | H | | 613 |
| 96 | i-Pr | (Fluorophen-3-yl)CH₂NHCONH | H | | 613 |
| 97 | i-Pr | Morpholin-4-ylCONH | H | | 575 |
| 98 | i-Pr | PhCH₂N(CH₃)CONH | H | | 609 |
| 99 | i-Pr | Tetrahydrofur-2-ylCH₂NHCONH | H | | 585 |
| 100 | i-Pr | 4-hydroxypiperid-1-ylCONH | H | | 589 |
| 101 | i-Pr | Pyrid-2-ylCH₂NHCONH | H | | 596 |
| 102 | i-Pr | Pyrid-3-ylCH₂NHCONH | H | | 596 |
| 103 | i-Pr | 4-Methylpiperazin-1-ylNHCONH | H | | 603 |
| 104 | i-Pr | Pyrid-3-ylNHCONH | H | | 582 |
| 105 | i-Pr | (CH₃)₂NCH₂CH₂N(CH₃)CONH | H | | 590 |
| 106 | Et | (CH₃)₂NCH₂CONH | Me | 218–221 | 547 |
| 107 | i-Pr | (Methoxyphen-2-yl)CH₂NHCONH | H | | 625 |
| 108 | i-Pr | (Methoxyphen-4-yl)CH₂NHCONH | H | | 625 |
| 109 | i-Pr | 2-hydroxypiperid-1-ylCONH | H | | 589 |
| 110 | Et | CH₃CONH | H | | 488 |

Example 111

4,6-Trichlorophenyl)-3-ethyl-6-(4-methanesulfonylaminobenzyl)pyrazolo[3,4-d]pyrimidin-4-one To a stirred solution of 45 mg (0.1 mmol) of 1-(2,4,6-trichlorophenyl)-3-ethyl-6-(4-aminobenzyl)pyrazolo[3,4-d]pyrimidin-4-one in 2 mL of ether-CH₂Cl₂ was added 0.5 mL of pyridine followed by 0.020 mL (0.26 mmol) of methanesulfonyl chloride. The solution was stirred 39 h at ambient temperature and poured into 1 N aq. HCl. The mixture was extracted with EtOAc, then hexanes. The combined organic extracts were washed with water then brine, dried (MgSO₄), and concentrated under reduced pressure to afford 52 mg of 1-(2,4,6-trichlorophenyl)-3-ethyl-6-(4-methanesulfonylaminobenzyl)pyrazolo[3,4-d]pyrimidin-4-one as an amorphous solid. Mass ESI+): 526(M+H)⁺.

Example 112

1-(2,4,6-Trichlorophenyl)-3-isopropyl-6-(4-(piperazin-1-ylmethylcarbonylamino)benzyl)pyrazolo[3,4-d]pyrimidin-4-one Part A: To a stirred, cooled (0° C.) solution of 9.26 g (20 mmol) of 1-(2,4,6-trichlorophenyl)-3-isopropyl-6-(4-aminobenzyl)pyrazolo[3,4-d]pyrimidin-4-one in 45 mL of THF and 10 mL of DMF was added 3.90 mL (28 mmol) of triethylamine followed by 1.99 mL (25 mmol) of chloroacetyl chloride over 5 min. The solution was stirred 30 min. at 0° C. and quenched by addition of 150 mL of 0.1 N aq. HCl. The resulting solid was collected by filtration, washed with water then 1:1 ether-hexanes, and air-dried to afford 10.2 g (95%) of 1-(2,4,6-trichlorophenyl)-3-isopropyl-6-(4-(chloroacetamido)benzyl)pyrazolo[3,4-d]pyrimidin-4-one as a white solid. ¹H NMR (300 MHz, DMSO) δ 12.49(s, 1H); 9.74(s, 1H); 7.97(s, 2H); 7.46(d, 2H, J=8.0 Hz); 7.20(d, 2H, J=8.8 Hz); 4.19(s, 2H); 3.80(s, 2H); 3.20–3.33(m, 1H); 1.28(d, 6H, J=6.9 Hz).

Part B: To a stirred solution of 300 mg (0.55 mmol) of 1-(2,4,6-trichlorophenyl)-3-isopropyl-6-(4-(chloroacetamido)benzyl)pyrazolo[3,4-d]pyrimidin-4-one in 6 mL of 1:1 DMF-THF was added 1 g of piperazine. The solution was stirred overnight at ambient temperature and poured into water. The mixture was extracted twice with EtOAc, and the combined organic extracts were washed (brine), dried (MgSO₄), and concentrated under reduced pressure to afford 230 mg (71%) of 1-(2,4,6-trichlorophenyl)-3-isopropyl-6-(4-(piperazin-1-ylmethylcarbonylamino)benzyl)pyrazolo[3,4-d]pyrimidin-4-one as an off-white solid. Mass spec.(ESI+): 588((M+H)⁺).

Example 113

(S)-1-(2,4,6-Trichlorophenyl)-3-isoprophyl-6-(4-(N-t-butoxycarbonylprolinamido)benzyl)pyrazolo[3,4-d]pyrimidin-4-one To a stirred solution of 105 mg (0.22 mmol) of 1-(2,4,6-trichlorophenyl)-3-isopropyl-6-(4-aminobenzyl)pyrazolo[3, 4-d]pyrimidin-4-one and 235 mg (1.09 mmol) of Boc-L-proline in 2 mL of DMF was added 0.35 mL (2.5 mmol) of triethylamine followed by 490 mg (1.11 mmol) of Bop. The solution was stirred overnight at ambient temperature then poured into EtOAc. This solution was washed sequentally with 0.5 M HCl then dilute aq. $Na_2CO_3$ then brine, dried ($MgSO_4$), and concentrated under reduced pressure. The crude product was recrystallized from EtOAc-hexanes to afford 116 mg (80%) of (S)-1-(2,4,6-trichlorophenyl)-3-isopropyl-6-(4-(N-t-butoxycarbonylprolinamido)benzyl) pyrazolo[3,4-d]pyrimidin-4-one as a white solid, mp 225–226° C., Mass spec.: 657 M–H$^-$).

Example 114

(S)-1-(2,4,6-trichlorophenyl)-3-isopropyl-6-(4-(prolinamido)benzyl)pyrazolo[3,4-d]pyrimidin-4-one Fifty mg (0.076 mmol) of (S)-1-(2,4,6-trichloro phenyl)-3-isopropyl-6-(4-(N-t-butoxycarbonylprolinamido)benzyl) pyrazolo[3,4-d]pyrimidin-4-one was dissolved in 2 mL of 4 M HCl, and the solution was stirred 1 h at RT. The solution was concentrated under reduced pressure to afford 45 mg (100%) of (S)-1-(2,4,6-trichlorophenyl)-3-isopropyl-6-(4-(prolinamido)benzyl)pyrazolo[3,4-d]pyrimidin-4-one as a white, amorphous solid. $^1$H NMR (300 MHz, DMSO) δ 12.42(s, 1H); 10.67(s, 1H); 7.97(s, 2H); 7.49(d, 2H, J=8.5 Hz); 7.23(d, 2H, J=8.4 Hz); 4.27–4.31(m, 1H); 3.82(s, 2H); 3.18–3.34(m, 5H); 2.28–2.40(m, 1H); 1.84–1.95(m, 3H); 1.28(d, 6H, J=6.9 Hz).

Example 115

1-(2,4,6-trichlorophenyl)-3-isopropyl-6-(4-(dimethylamino methyl)-3-hydroxybenzyl)pyrazolo[3,4-d]pyrimidin 4-one To a stirred solution of 464 mg (1.0 mmol) of 1-(2,4,6-trichlorophenyl)-3-isopropyl-6-(3-hydroxybenzyl)pyrazolo[3,4-d]pyrimidin-4-one in 10 mL of glacial HOAc was added 0.4 mL of 37% aq. formaldehyde followed by 0.5 mL of 40% aq. dimethylamine. The solution was stirred overnight at RT, and it was then heated to just below reflux for 20 min. The solution was poured into water and extracted with EtOAc. The organic extract was washed (brine), dried ($MgSO_4$), and chromatographed on silica gel (elution with EtOAc) to afford, after removal of solvent, 135 mg (26%) of 1-(2,4,6-trichlorophenyl)-3-isopropyl-6-(4-(dimethylaminomethyl)$^3$-hydroxybenzyl)pyrazolo[3,4d]pyrimidin-4-one as an off-white, amorphous solid. Mass pec.(ESI+): 520(M+H)$^+$.

Example 116

1-(2 4,6-trichlorophenyl)-3-ethyl-6-(3-pyridylmethyl)pyrazolo[3,4-d]pyrimidin-4-one To a stirred solution of 167 mg (0.5 mmol) of 1-(2,4,6-trichlorophenyl)-3-ethyl-4-carboxamido-5-aminopyrazole in 5 mL of ethanol was added 480 mg (3.0 mmol) of ethyl 3-pyridyl acetate followed by 1.13 mL (3.0 mmol) of 2.66 M NaOEt in ethanol. The solution was stirred overnight at reflux, and the product was precipitated by treatment with 10 mL of 10% aq. HOAc. The mixture was filtered, and the product was washed with 1:1 MeOH-water then 1:1 ether-hexanes and air dried to afford 210 mg (97%) of 1-(2,4,6-trichlorophenyl)-3-ethyl-6-(3-pyridylmethyl)pyrazolo[3,4-d]pyrimidin-4-one as an off-white solid, mp 257–260° C. $^1$H NMR (300 MHz, DMSO) δ 12.56(s, <1H (exchanges with solvent)); 8.46(d, 1H, J=1.5); 8.40(dd, 1H, J=4.8, 1.5 Hz); 7.96(s, 2H); 7.60–7.64(m, 1H); 7.25–7.30(m, 1H); 3.90(s, 2H); 2.83(q, 2H, J=7.3 Hz); 1.23(t, 3H, J=7.5 Hz).

Example 117

(+/−)-1-(2,4,6-Trichlorophenyl)-3-ethyl-6-(α-hydroxybenzyl)pyrazolo[3,4-d]pyrimidin-4-one To a stirred solution of 167 mg (0.50 mmol) of 1-(2,4,6-trichlorophenyl)-3-isopropyl-4-carboxamido-5-amino pyrazole in 6 mL of ethanol was added 544 mg (3.0 mmol) of (+/−) ethyl mandelate followed by 1.13 mL (3.0 mmol) of 2.66 M NaOEt in ethanol. The solution was stirred overnight at reflux, and the product was precipitated by treatment with 10 mL of 10% aq. HOAc. The mixture was filtered, and the product was washed with 1:1 MeOH-water then 1:1 ether-hexanes and air dried to afford 210 mg (94%) of 1-(2,4,6-trichlorophenyl)-3-isopropyl-6-(α-hydroxybenzyl)pyrazolo[3,4-d]pyrimidin-4-one as an off-white solid, mp 246–248° C. Mass spec. (ESI-): 449(M–H)$^-$.

Example 118

1-(2,4,6-Trichlorophenyl)-3-isopropyl-6-(4-(ethenesulfonamido)benzyl)pyrazolo[3,4-d]pyrimidin-4-one To a stirred, cooled (0° C.) solution of 231 mg (0.5 mmol) of 1-(2,4,6-trichlorophenyl)-3-isopropyl-6-(4-aminobenzyl)pyrazolo[3,4-d]pyrimidin-4-one and 0.14 mL (1.0 mmol) of Et$_3$N in 4 mL of THF was added 0.063 mL (0.6 mmol) of 2-chloroethanesulfonyl chloride. The solution was stirred 1 h, warming to ambient temperature. The solution was poured into 10% aq. citric acid and extracted with EtOAc. The organic extract was washed (brine), dried ($MgSO_4$), and concentrated under reduced pressure. The crude product was chromatographed (elution with 1:1 EtOAc-hexanes) to afford 221 mg (80%) of 1-(2,4,6-trichlorophenyl)-3-isopropyl-6-(4-(ethenesulfonamido)benzyl)pyrazolo[3,4-d] pyrimidin-4-one as an off-white solid. $^1$H NMR (300 MHz, DMSO) δ 12.47(br. s, 1H); 9.92(br. s, 1H); 7.97(s, 2H); 7.17(d, 2H, J=8.4 Hz); 7.02(d, 2H, J 8.4 Hz); 6.69(dd, 1H, J=16.5, 9.9 Hz); 6.04(d, 1H, J=16.5 Hz); 5.96(d, 1H, J=9.9 Hz); 3.78(s, 2H); 3.18–3.32(m, 1H); 1.28(d, 6H, J=7.0 Hz).

Example 119

1-(2,4,6-Trichlorophenyl)-3-isopropyl-6-(4-(2-(dimethylamino)ethanesulfonamido)benzyl)pyrazolo[3,4-d]pyrimidin-4-one To a stirred, solution of 23 mg(0.042 mmol) of 1-(2,4,6-trichlorophenyl)-3-isopropyl-6-(4-(ethenesulfonamido) benzyl)pyrazolo[3,4-d]pyrimidin-4-one in 1 mL of THF was added 1 mL of 2M diethylamine in THF. The solution was stirred 3 h and concentrated under reduced pressure. The product was dissolved in 1 mL of benzene and 0.05 mL of MeOH, frozen, and lyophilized to afford 25 mg (100%) of 1-(2,4,6-trichlorophenyl)-3-isopropyl-6-(4-(2-(dimethylamino)ethenesulfonamido) benzyl)pyrazolo[3,4-d]pyrimidin-4-one as an amorphous white solid. $^1$H NMR (300 MHz, DMSO) δ 7.96(s, 2H); 7.19(d, 2H, J=8.5 Hz); 7.08(d, 2H, J=8.8 Hz); 3.79(s, 2H); 3.18–3.32(m, 1H); 3.13(t, 2H, J=7.5 Hz); 2.53(t, 2H, J=7.5 Hz); 1.99(s, 6H); 1.28(d, 6H, J=7.0 Hz).

Example 120

1-(2,4,6-Trichlorophenyl)-3-isoropyl-6-(4-(hydroxymethyl)benzyl)pyrazolo[3,4-d]pyrimidin-4-one To a stirred solution of 347 mg (1.0 mmol) of 5-amino-3-isopropyl-1-(2,4,6-trichlorophenyl)pyrazole-4- carboxamide in 6 mL of absolute ethanol was added 777 mg (4.0 mmol) of ethyl 4-(hydroxymethyl)phenylacetate followed by 2.0 mL (5.33 mmol) of 2.66 M sodium ethoxide in ethanol. The solution was stirred 18 h at reflux, and the heating mantle was then removed. The reaction was treated with 25 mL of 5% aq. HOAc, cooled to ambient temperature, and extracted with EtOAc. The organic extract was washed twice with water and once with brine, dried (MgSO$_4$), and chromatographed on silica gel. (elution with 1:1 EtOAc-hexanes) to give, after removal of solvent, 320 mg (67%) of 1-(2,4,6-trichlorophenyl)-3-isopropyl-6-(4-(hydroxymethyl)benzyl)pyrazolo[3,4-d]pyrimidin-4-one as a white, amorphous solid. $^1$H NMR (300 MHz, CDCl$_3$) d 11.46(br. s, 1H); 7.54(s, 2H); 7.42(d, 2H, J=8.1 Hz); 7.31(d, 2H, J=8.5 Hz); 4.66(s, 2H); 4.00(s, 2H); 3.47(septet, 1H, J=7.0 Hz); 1.48(d, 6H, J=7.0 Hz).

Example 121

(+/−)-1-(2,4,6-Trichlorophenyl)-3-isopropyl-6-(4-(1, 4-dimethylpiperazine-2-ylcarboxamido)benzyl) pyrazolo[3.4-d]pyrimidin-4-one Part A: To a stirred, cooled (0° C.) solution of 463 mg (1.0 mmol) of 1-(2,4,6-trichlorophenyl)-3-isopropyl-6-(4-aminobenzyl)pyrazolo[3,4-d]pyrimidin-4-one and 0.28 mL (2.0 mmol) of Et$_3$N in 8 mL of THF was added 0.131 mL (1.2 mmol) of 2,3-dichloropropanoyl chloride. The solution was stirred 0.5 h, warming to ambient temperature. The solution was quenched with water and filtered. The solid was washed with 0.1 N aq. HCl, then water, then 1:1 hexanes-ether. The product was air-dried briefly to afford 390 mg (71%) of 1-(2,4,6-trichlorophenyl)-3-isopropyl-6-(4-(2-chloroacrylamido)benzyl)pyrazolo[3,4-d]pyrimidin-4-one as an amorphous solid. $^1$H NMR (300 MHz, DMSO) δ 12.49(br. s, 1H); 10.14(br. s, 1H); 7.97(s, 2H); 7.53(d, 2H, J=8.4 Hz); 7.22(d, 2H, J=8.4 Hz); 6.36(d, 1H, J=2.6 Hz); 6.03(d, 1H, J=2.5 Hz); 3.82(s, 2H); 3.18–3.32(m, 1H); 1.28(d, 6H, J=7.0 Hz).

Part B: To a stirred, solution of 112 mg (0.2 mmol) of 1-(2,4,6-trichlorophenyl)-3-isopropyl-6-(4-(2-chloroacrylamido)benzyl)pyrazolo[3,4-d]pyrimidin-4-one in 2 mL of THF was added 0.5 mL of N, N'-dimethylethylene diamine. The solution was stirred overnight, poured into water, and extracted with EtOAc. The organic extract was washed (brine), dried (MgSO$_4$), and concentrated under reduced pressure to afford 102 mg (84%) of 1-(2,4,6-trichloro phenyl)-3-isopropyl-6-(4-(1,4-dimethyl piperazine-2-ylcarboxamido)benzyl)pyrazolo[3,4-d] pyrimidin-4-one as an amorphous white solid. Mass spec. (ESI+): 602.1608(M+H)$^+$.

Example 122

1-(2,6-dichlorophenyl)-3-isopropyl-6-(4-(carbethoxymethyl)benzyl)pyrazolo[3,4-d] pyrimidin-4-one The amino carboxamide, 5-amino-3-isopropyl-1-(2,6-dichlorophenyl)pyrazole-4-carboxamide (0.30 g, 0.96 mmol), p-diethyl phenylenediacetate (8 eq, 1.92 g, 7.66 mmol) and sodium ethoxide (21% in ethanol, 8 eq, 2.90 mL, 7.66 mmol) were refluxed overnight in ethanol (20 mL). The reaction was cooled and 10% aq HOAc was added. The mixture was extracted with EtOAc, washed with water and brine, dried over MgSO$_4$ and evaporated to dryness. The oily solid was purified by silica gel column chromotography with 1:1hexane/ether as the eluent. The product, 1-(2,6-dichlorophenyl)-3-isopropyl-6-(4-(carbethoxymethyl) benzyl)pyrazolo[3,4-d]pyrimidin-4-one (0.44 g, 93% yield), was recovered as a white solid, mp 168–169° C. Mass Spec.: 499 (M+H)$^+$.

Example 123

1-(2,6-Dichlorophenyl)-3-isopropyl-6-(4-(carboxymethyl)benzyl)pyrazolo[3,4-d]pyrimidin-4-one The ester, 1-(2,6-dichlorophenyl)-3-isopropyl-6-(4-(carbethoxymethyl)benzyl)pyrazolo[3,4-d]pyrimidin-4-one (1.20 g, 2.4 mmol) was stirred at RT overnight with THF (50 mL), water (15 mL) and 1 N lithium hydroxide (7.20 mL). The solution was evaporated to near dryness, diluted with 1 N hydrochloric acid, vigorously stirred and the solid was collected by filtration and dried under high vacuum to give 1-(2,6-dichlorophenyl)-3-isopropyl-6-(4-carboxymethyl) benzyl)pyrazolo[3,4-d]pyrimidin-4-one (1.01 g, 89% yield) as a white solid, mp 212–214° C. Mass Spec.: 471 (M+H)$^+$.

Example 124

1-(2.6-Dichlorophenyl)-3-isopropyl-6-(4-(2-(N,N-dimethylamino)ethylaminocarbonylmethyl)benzyl) pyrazolo[3,4-d]pyrimidin-4-one The acid, 1-(2,6-dichlorophenyl)-3-isopropyl-6-(4-carboxymethyl)benzyl)pyrazolo[3,4-d]pyrimidin-4-one (0.100 g, 0.21 mmol) and N,N-dimethyethylenediamine (5 eq, 0.12 mL, 1.06 mmol) were suspended in DMF (3 mL). DIEA (5 eq, 0.18 mL, 1.06 mmol) was added and the suspension was stirred at RT for ten minutes. BOP (1.5 eq, 0.141 g, 0.32 mmol) was added and the reaction was stirred at RT overnight. The suspension was diluted with water, extracted with EtOAc, washed with water and brine, dried over MgSO$_4$ and evaporated to dryness. The oily residue was crystallized from a mixture of EtOAc, hexane and ether to give 1-(2,6-dichlorophenyl)-3-isopropyl-6-(4-(2-(N,N-dimethylamino)ethylaminocarbonylmethyl)benzyl)pyrazolo [3,4-d]pyrimidin-4-one (0.039 g, 34% yield) as a white solid, mp 170–172° C. Mass Spec.: 541 (M+H)$^+$.

Example 125

1-(2,4,6-Trichlorophenyl)-3-isopropyl-6-(4-(2-(morpholine-4-yl)ethylaminocarbonylamino)benzyl) pyrazolo[3.4-d]pyrimidin-4-one A flask equipped with a reflux condenser was flame-dried in vacuo and a nitrogen atmosphere was introduced. The flask was charged with triphosgene (1.37 g, 4.62 mmol). The reagent was dissolved in dry 1,2-dichloroethane (25 mL), and triethylamine (0.64 mL, 4.62 mmol) was added. The reaction was cooled to −30° C., and 1-(2,4,6-trichlorophenyl)-3-isopropyl-6-(4-aminobenzyl)pyrazolo[3, 4-d]pyrimidin-4-one (1.1 g, 2.38 mmol) was added. Stirring was continued for 10 minutes and the reaction was the warmed to reflux. After heating for one hour, the reaction was cooled, diluted with methylene chloride, and washed sequentially with water and brine. The organic phase was dried over magnesium sulfate, filtered and evaporated to give the isocyanate (1.2 g). This material was of sufficient quality for the subsequent transformations.

The isocyanate (75.5 mg, 0.155 mmol) was dissolved in dry methylene chloride (2.0 mL) under a nitrogen atmosphere. 4-(2-aminoethyl)morpholine (30 μΛ, 0.232 mmol) was added, and stirring was continued for 1 hour. The precipitate was filtered and rinsed with three portions of methylene chloride and dried in vacuo to give 1-(2,4,6-trichlorophenyl)-3-isopropyl-6-(4-(2-(morphline-4-yl) ethylaminocarbonylamino)benzyl)pyrazolo[3,4-d] pyrimidin-4-one (68 mg, 0.110 mmol, 71%). Mass spec. (ESI+) 618 (M+H)⁺.

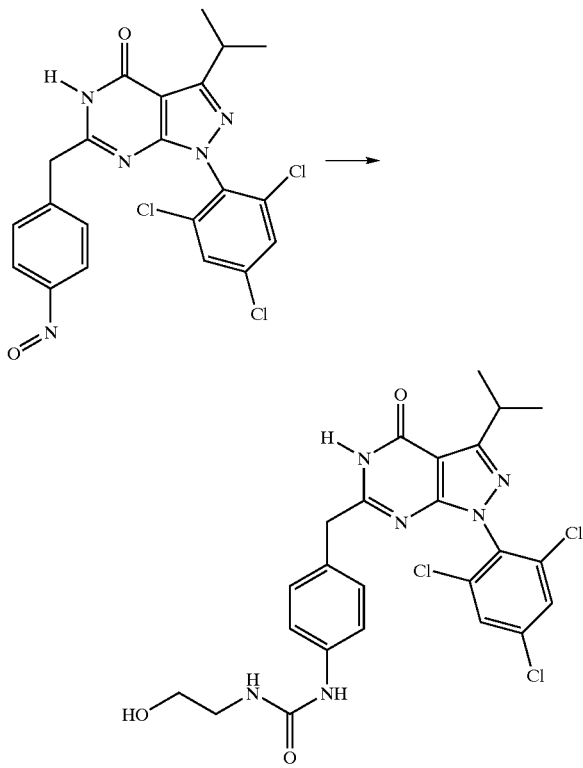

Example 126

1-(2,4,6-Trichlorophenyl)-3-isopropyl-6-(4-(2-hydroxyethylaminocarbonylamino)benzyl)pyrazolo[3,4-d]pyrimidin-4-one Alternatively, the ureas may be prepared by the following procedure, which is suitable for parallel synthesis. The isocyanate (74 mg, 0.152 mmol) was dissolved in dry methylene chloride (3.0 mL) under a nitrogen atmosphere. Ethanolamine (14μΛ, 0.227 mmol) was added and stirring continued for 15 minutes. Methanol (1.0 mL) was added to generate a homogeneous solution. The acidic ion exchange resin AG 50W-X8-(158 mg) was added. The reaction was then filtered and the solvents removed by evaporation. The product 1-(2,4,6-trichlorophenyl)-3-isopropyl-6-(4-(2-hydroxyethyl aminocarbonylamino)benzyl)pyrazolo[3,4-d]pyrimidin-4-one was obtained in excellent yield (78 mg, 93%). Mass spec. (ESI-) 547 (M-H)⁻.

Example 127

1-(2-Chloro-6-methylphenyl)-3-isopropyl-6-(4-aminobenzyl)pyrazolo[3,4-d]pyrimidin-4-one Part A: To a stirred suspension of 14.2 g (100 mmol) of 2-chloro-6-methylaniline in 40 mL conc. HCl at 0° C. was added a solution of 6.9 g (100 mmol) of sodium nitrite in 40 mL water dropwise via addition funnel. After stirring one hour at 0° C. a solution of 67.6 g (300 mmol) tin (II) chloride dihydrate in 70 mL conc. HCl was added dropwise via addition funnel. The reaction was sealed and placed in the refrigerator for 24 h. The mixture was filtered and the solid was washed with brine and then petroleum ether. The solid was taken up in 250 mL of 2 N NaOH, stirred 10 min. and filtered. This solid was dissolved in 100 mL diethyl ether and acidified with 4N HCl in dioxane. The solid was collected by suction filtration, washed with diethyl ether and dried to afford 10.25 g (53%) of 2-chloro-6-methylhydrazine hydrochloride, mp 220–222 (dec)° C. Mass Spec (CI+): 157 (M+H)⁺.

Part B: To a stirred suspension of 3.0 g (15.5 mmol) of 2-chloro-6-methylhydrazine hydrochloride in 20 mL ethanol was added 2.2 mL (15.5 mmol) of triethylamine followed after 10 min by 1.5 mL (16.5 mmol) of isobutyraldehyde. The solution was stirred at room temperature for 2 h, poured into water and extracted with diethyl ether. The organic extract was washed with brine, dried (MgSO₄), and concentrated under reduced pressure to give 2.95 g (90%) of the imine intermediate as a liquid. The imine was taken up in 15 mL dimethylformamide, cooled to 0° C., and 2.99 g (16.8 mmol) of N-bromosuccinimide was added in small portions. After stirring at 0° C. for 30 min the reaction was diluted with diethyl ether and water. The layers were separated and the aqueous phase with extracted with diethyl ether. The organic extracts were combined, washed with water and brine, dried (MgSO₄) and concentrated under reduced pressure to give the bromohydrazone intermediate. To a stirred solution of the bromohydrazone in 25 mL ethanol was added an ice cold solution of the anion of malononitrile prepared by adding 10.4 mL (28 mmol) of sodium ethoxide to 1.82 g (28 mmol) of malononitrile in 25 mL ethanol at 0° C. The mixture was heated to reflux for 30 min and then concentrated to one third the volume under reduced pressure. This solution was treated with 10% glacial acetic acid, diluted with water, and extracted with EtOAc. The organic extract was washed with brine, dried (MgSO₄), and concentrated under reduced pressure. Purification by column chromatography on silica gel using 2:1 hexanes-EtOAc as eluant afforded 1.82 g (47%) of 5-amino-4-cyano-3-isopropyl-1-(2-chloro-6-methylphenyl)pyrazole, mp 116–118° C. Mass Spec. (CI+): 275 (M+H)⁺.

Part C: A mixture of 1.5 g (5.5 mmol) of 5-amino-4-cyano-3-isopropyl-1-(2-chloro-6-methylphenyl)pyrazole in 5 mL conc. H₂SO₄ was stirred at room temperature for 24 hours. The reaction was slowly quenched with ice and then diluted with water. The solution was made basic with saturated Na₂CO₃, stirred 2 h and filtered. The solid was recrystallized from hexanes/EtOAc to afford 847 mg (53%) of 5-amino-3-isopropyl-1-(2-chloro-6-methylphenyl)pyrazole-4-carboxamide, mp 72–74° C. Mass Spec. (ES-): 291 (M-H)⁻.

Part D: To a stirred solution of 1.4 g (4.8 mmol) 5-amino-3-isopropyl-1-(2-chloro-6-methyl-phenyl)pyrazole-4-carboxamide in 100 mL absolute ethanol was added 5.14 g (28.8 mmol) of 4-amino-phenylacetate followed by 10.7 mL (28.8 mmol) of 2.66 M sodium ethoxide in ethanol. The solution was stirred 18 h at reflux and the heating mantle was then removed. The reaction was treated with water and 10% aq. HOAc, cooled to ambient temperature, and filtered. The solid purified by coloumn chromatography on silica gel using 1:1 hexanes-EtOAc as eluant to afford 743 mg (38%) of 1-(2-chloro-6-methylphenyl)-3-isopropyl-6-(4-aminobenzyl)-pyrazolo[3,4-d]pyrimidin-4-one, mp 206–207° C. Mass Spec.(CI+): 408 (M+H)⁺.

Example 128

1-(2-Chloro-6-methylphenyl)-3-isopropyl-6-(4-(N,N-dimethylglycinamido)benzyl)pyrazolo[3,4-d] pyrimidin-4-one hydrochloride salt To a stirred solution of 500 mg (1.22 mmol) of 1-(2-chloro-6-methylphenyl)-3-isopropyl-6-(4-aminobenzyl)- pyrazolo[3,4-d]pyrimidin-4-one in 10 mL dry $CH_2Cl_2$ was added 0.85 mL (6.1 mmol) triethylamine followed by 632 mg (6.1 mmol) N,N-dimethylglycine and then 1.17 g (6.1 mmol) of 1-(3-dimethyl-aminopropyl)-3-ethylcarbodiimide hydrochloride (EDC). The reaction was stirred for 18 h at ambient temperature and then transferred directly to a flash column of silica gel and eluted with 5% MeOH in $CH_2Cl_2$. The isolated solid was dissolved in 20 mL dioxane and 1.1 mL of 4 N HCl in dioxane was added. The solid was collected by suction filtration and dried to give 490 mg (76%) of 1-(2-chloro-6-methylphenyl)-3-isopropyl-6-(4-(N,N-dimethylglycinamido)benzyl)pyrazolo[3,4-d]pyrimidin-4-one hydrochloride salt, mp 297–299° C.

Example 129

1-(2,6-Dichloro-4-methylcarboxamido phenyl)-3-ethyl-6-(4-methoxybenzyl)pyrazolo[3,4-d]pyrimidin-4-one Part A: To a stirred suspension of 4.33 g (18.5 mmol) of ethyl 4-amino-3,5-dichlorobenzoate in 8 mL conc. HCl at 0° C. was added a solution of 1.28 g (18.5 mmol) of sodium nitrite in 8 mL water dropwise. After stirring at 0° C. for 45 min, a solution of 12.52 g (55.5 mmol) tin(II) chloride in 14 ML conc. HCl was added dropwise. The reaction was sealed and placed in the refrigerator for 18 h. The solid was collected by suction filtration, washed with brine and then 2:1 petroleum ether-diethyl ether, treated with 1 N NaOH, and filtered. This solid was dissolved in diethyl ether, acidified with 4 N HCl in dioxane, filtered and washed with diethyl ether to give 2.85 g (54%) of ethyl 3,5-dichloro-4-hydrazinobenzoate hydrochloride, mp 225–227 (dec)° C. Mass Spec.: (CI+) 249 (M+).

Part B: A mixture of 2.5 g (8.75 mmol) ethyl 3,5-dichloro-4-hydrazinobenzoate hydrochloride, 1.1 g (7.3 mmol) 1-(ethoxypropylidine)malononitrile and 1.22 mL (8.75 mmol) triethylamine in 100 mL of ethanol was stirred at reflux for 66 h. The reaction was taken to one-third the volume via rotary evaportation under reduced pressure and the remaining solution was treated with water, stirred 30 min and filtered. Recrystallization from hexanes/EtOAc gave 1.16 g (45%) of 5-amino-4-cyano-3-ethyl-1-(2,6-dichloro-4-carboethoxyphenyl)pyrazole, mp 173–175° C. Mass Spec.: (CI+) 353 (M+).

Part C: A solution of 1.64 g (4.64 mmol) of 5-amino-4-cyano-3-ethyl-1-(2,6-dichloro-4-carboethoxyphenyl)-pyrazole in 8 mL conc. $H_2SO_4$ was stirred at room temperature for 4 hours. The reaction was quenched carefully with ice and diluted with water. The solid was collected by suction filtration, washed with water and dried to give 1.26 g (73%) of 5-amino-3-ethyl-1-(2,6-dichloro-4-carboethoxyphenyl)pyrazole-4-carboxamide, mp 194–196° C. Mass Spec.: (CI+) 371 (M+).

Part D: To a stirred solution of 500 mg (1.35 mmol) of 5-amino-3-ethyl-1-(2,6-dichloro-4-carboethoxyphenyl)pyrazole-4-carboxamide in 10 mL ethanol was added 1.45 g (8.1 mmol) of methyl 4-methoxyphenylacetate followed by 2.6 mL (8.1 mmol) of 2.66 M sodium ehtoxide in ethanol. The reaction was heated at relux for 18 h and then 10% aq. HOAc was added. After stirring an additional hour at relux, the heat was removed and the reaction solution was poured into ice water, stirred 10 min. and filtered. The solid was washed with water and diethyl ether and dried to give 480 mg (75%) of 1-(2,6-dichloro-4-carboxyphenyl)-3-ethyl-6-(4-methoxybenzyl)pyrazolo[3,4-d]pyrimidin-4-one, mp 277° C. Mass Spec.: (ES–) 471 (M–H)⁻.

Part E: To a stirred solution of 100 mg (0.21 mmol) of 1-(2,6-dichloro-4-carboxyphenyl)-3-ethyl-6-(4-methoxybenzyl)pyrazolo[3,4-d]pyrimidin-4-one was added 0.3 mL (2.1 mmol) of triethylamine followed by 71 mg (1.05 mmol) of methylamine hydrochloride and then 202 mg (1.05 mmol) of EDC. The reaction was stirred at ambient temperature for 18 h, transferred directly to a flash column of silica gel and eluted with 5% MeOH in $CH_2Cl_2$ to give 14 mg (14%) of 1-(2,6-dichloro-4-(methylcarboxamido)phenyl)-3-ethyl-6-(4-methoxybenzyl)pyrazolo[3,4-d]pyrimidin-4-one, mp 280–282° C. Mass Spec.: (CI+) 486 (M+).

Example 130

1-(2,4,6-Trichlorophenyl)-3-isopropyl-6-(4-(t-butoxycarbonylaminosulfonamido)benzyl)pyrazolo[3,4]pyrimidin-4-one To a stirred, cooled solution of 0.11 mL (1.26 mmol) of chlorosulfonyl isocyanate in 5 mL of $CH_2Cl_2$ was added 0.13 mL of t-BuOH. The solution was stirred 10 min. and added to a stirred, cooled (0° C.) solution of 231 mg (0.5 mmol) of 1-(2,4,6-trichlorophenyl)-3-isopropyl-6-(4-aminobenzyl)pyrazolo[3,4-d]pyrimidin-4-one and 0.2 mL (1.4 mmol) of $Et_3N$ in 5 mL of $CH_2C_{1-2}$. The solution was stirred 1 h warming to ambient temperature, and it was then poured into 1 N aq. HCl. The mixture was extracted with EtOAc, and the organic extract was washed (brine), dried ($MgSO_4$), concentrated under reduced pressure, and chromatographed on silica gel (elution with 1:1 EtOAc-hexanes, then EtOAc) to afford 250 mg (78%) of 1-(2,4,6-trichlorophenyl)-3-isopropyl-6-(4-(t-butoxycarbonylaminosulfonamido)benzyl)pyrazolo[3,4-d]pyrimidin-4-one as a white solid. $^1H$ NMR (300 MHz, DMSO) δ 12.44(s, 1H); 11.12(br. s, 1H); 9.70(br. s, 1H); 7.97(s, 2H); 7.21(d, 2H, J=8.4 Hz); 7.02(d, 2H, J=8.4 Hz); 3.78(s, 2H); 3.19–3.30(m, 1H); 1.27(d, 6H, J=6.9 Hz); 1.21(s, 9H).

Example 131

1-(2,4 6-Trichlorophenyl)-3-isopropyl-6-(3-aminoindazol-5-ylmethyl)pyrazolo[3,4-d]pyrimidin-4-one To a stirred solution of 139 mg (0.40 mmol) of 5-amino-3-isopropyl-1-(2,4,6-trichlorophenyl)pyrazole-4-carboxamide in 3 mL of absolute ethanol was added 329 mg (1.50 mmol) of ethyl 3-aminoindazol-5-ylacetate followed by 1.13 mL (3.0 mmol) of 2.66 M sodium ethoxide in ethanol. The solution was stirred 16 h at reflux, and the heating mantle was then removed. The reaction was treated with 8 mL of 10% aq. HOAc, poured into water, and extracted with EtOAc. The organic extract was washed with brine, dried ($MgSO_4$), concentrated under reduced pressure, and chromatographed on silica gel (gradient elution with 5% to 10% MeOH-$CH_2Cl_2$) to give, after removal of solvent, 123 mg (61%) of 1-(2,4,6-trichlorophenyl)-3-isopropyl-6-(3-aminoindazol-5-ylmethyl)pyrazolo[3,4-d]pyrimidin-4-one as a white, amorphous solid. Mass spec. 502.0712(M+H)⁺.

Example 132

1-(2,4,6-Trichlorophenyl)-3-isopropyl-6-(benzoxazol-2-on-6-ylmethyl)pyrazolo[3.4-d]pyrimidin-4-one To a stirred, cooled (0° C.) solution of 309 mg (0.063 mmol) of 1-(2,4,6-trichlorophenyl)-3-isopropyl-6-(4-amino- 3-hydroxybenz)pyrazolo[3,4-d]pyrimidin-4-one in 1 mL of THF was added 0.13 mL (1.0 mmol) of triethylamine followed by 0.05 mL (0.095 mmol) of 1.93 M phosgene in toluene. The solution was stirred 15 min., treated with 4 mL of 0.1 N aq. NaOH, and stirred 64 h at RT. The reaction was poured into 1 N aq. HCl and extracted with EtOAc. The organic extract was washed with brine, dried (MgSO$_4$ plus activated charcoal and celite), and concentrated under reduced pressure to afford 26 mg (81%) of 1-(2,4,6-trichlorophenyl)-3-isopropyl-6-(benzoxazol-2-on-6-ylmethyl)pyrazolo[3,4-d]pyrimidin-4-one as an amorphous solid. $^1$H NMR (300 MHz, DMSO) δ 12.48(s, 1H); 11.57(br. s, 1H); 7.98(s, 2H); 7.03(dd, 1H, J=8.1, 1.4 Hz); 6.97(d, 1H, J=8.1 Hz); 3.84(s, 2H); 3.19–3.30(m, 1H); 1.28(d, 6H, J=7.0 Hz).

Example 133

1-(2,4,6-Trichlorophenyl)-3-isopropyl-6-(4-(2-(dimethylamino)ethoxycarbonylamino)benzyl)pyrazolo[3,4-d]pyrimidin-4-one To a stirred, cooled(−78° C.) solution of 0.10 mL(1.0 mmol) of N,N-dimethylethanolamine in 1 mL of THF was added 0.56 mL(0.90 mmol) of 1.6 M n-BuLi in hexanes over 2 min. The solution was stirred 5 min. at −78° C. and treated with 49 mg (0.10 mmol) of the isocyanate prepared in Example 107 above. The mixture was stirred 10 min., becoming homogeneous as it warmed to 0° C. The reaction was diluted with 5% aq. HOAc, then made slightly basic with saturated aq. NaHCO$_3$. The mixture was extracted with EtOAc, and the organic extract was washed (brine), dried (MgSO$_4$), and concentrated under reduced pressure to afford 43 mg(74%) of 1-(2,4,6-Trichlorophenyl)-3-isopropyl-6-(4-(2-(dimethylamino)ethoxycarbonylamino)benzyl)pyrazolo[3,4-d]pyrimidin-4-one as a white solid, mp. 218–220° C. Mass spec: 577(M+H)$^+$.

Example 134

1-(2,4,6-trichlorophenyl)-3-isopropyl-6-(1-methylpyrroy-2-ylmethyl)pyrazolo[3.4-d]pyrimidin-4-one To a stirred solution of 1.74 g (5.0 mmol) of 1-(2,4,6-trichlorophenyl)-3-isopropyl-4-carboxamido-5-aminopyrazole in 30 mL of ethanol was added 2.9 mL (20 mmol) of methyl 1-methyl-2-pyrroleacetate followed by 7.50 mL (20 mmol) of 2.66 M NaOEt in ethanol. The solution was stirred overnight at reflux, and the product was precipitated by treatment with 40 mL of 10% aq. HOAc. The mixture was filtered, and the product was washed with 1:1 MeOH-water then 1:1 ether-hexanes and air dried to afford 2.07 g (92%) of 1-(2,4,6-trichlorophenyl)-3-isopropyl-6-(1-methylpyrroy-2-ylmethyl)pyrazolo[3,4-d]pyrimidin-4-one as an off-white solid, mp 219–221° C. Mass spec.(ESI+): 450(M+H)$^+$.

Example 135

1-(3-Formyl-2,4,6-trichlorophenyl)-3-isopropyl-6-(1-methylpyrroy-2-ylmethyl)pyrazolo[3,4-d]pyrimidin-4-one To a stirred, cooled(−60° C.) solution of 902 mg (2.0 mmol) of 1-(2,4,6-trichlorophenyl)-3-isopropyl-6-(1-methylpyrroy-2-ylmethyl)pyrazolo[3,4-d]pyrimidin-4-one in 10 mL of THF was added 2.56 mL (4.1 mmol) of 1.6 M n-BuLi in hexanes over 2 min. The solution was stirred 10 min. at −60° C. and treated with 1 mL DMF. The reaction solidified and was broken up by stirring, shaking, and warming to ambient temperature. The reaction was quenched with deuteromethanol then aq. HOAc. The mixture was extracted with EtOAc, and the organic extraxt was washed (brine), dried (MgSO4), and concentrated under reduced pressure. The crude product was re-crystallized from EtOAc-hexanes to afford 560 mg(60%) of 1-(3-formyl-2,4,6-trichlorophenyl)-3-isopropyl-6-(1-methylpyrroy-2-ylmethyl)pyrazolo[3,4-d]pyrimidin-4-one as an orange solid. Mass spec. (ESI−): 450(M−H)$^-$.

Example 136

1-(2,4,6-trichlorophenyl)-3-isopropyl-6-(4-(4-methylypiperazin-1-ylaminocarbonyl)benzyl)pyrazolo[3,4-d]pyrimidin-4-one Part A: To a stirred solution of 7.5 g(153 mmol) sodium cyanide in 75 mL of THF was added 40 mL of DMF followed by 11.5 g(50.2 mmol) of of methyl 4-(bromomethyl)benzoate in 30 mL of DMF over 10 min. The solution was stirred 18 and treated with 100 mL water. The mixture was filtered, rinsed with water, and air-dried briefly to give 6.7 g (76%) of 4-(carbomethoxy)phenylacetonitrile as a white solid. $^1$H NMR (300 MHz, DMSO) δ 7.95(d, 2H, J=8.4 Hz); 7.47(d, 2H, J=8.5 Hz); 4.14(s, 2H); 3.82(s, 3H). Part B: The above nitrile ester was stirred with 120 mL of 6 N aq. HCl for 18 h at reflux and then cooled. The mixture was diluted with 160 mL water and then filtered. The white solid was rinsed with water, air-dried briefly, and placed in a vacuum oven at 75° C. for 1 h. This affords 6.89 g (100%) of 4-(carboxy)phenylacetic acid. $^1$H NMR (300 MHz, DMSO) δ 7.92(d, 2H, J=8.5 Hz); 7.49(d, 2H, J=8.4 Hz); 3.63(s, 2H)

Part C: To a stirred solution of 2.0 g (11.1 mmol) of 4-(carboxy)phenylacetic acid in 28 mL of absolute ethanol was added 0.5 mL of conc. Sulfuric acid. The solution was stirred 2 h at reflux and then cooled. The reaction was made basic with sodium carbonate and extracted with ether. The organic extract was washed (brine), dried (MgSO$_4$), and concentrated under reduced pressure to afford 2.3 g (88%) of ethyl 4-(carbethoxy)phenylacetate as an oil. $^1$H NMR (300 MHz, CDCl3) δ 8.01(d, 2H, J=8.4 Hz); 7.36(d, 2H, J=8.1 Hz); 4.37(q, 2H, J=7.1 Hz); 4.16(q, 2H, J=7.2 Hz); 1.39(t, 3H, J=7.2 Hz); 1.25(t, 3H, J=7.2 Hz).

Part D: To a stirred solution of 174 mg (0.50 mmol) of 1-(2,4,6-trichlorophenyl)-3-isopropyl-4-carboxamido-5-aminopyrazole in 6 mL of ethanol was added 473 mg (2.0 mmol) of ethyl 4-(carbethoxy)phenylacetate followed by 0.94 mL (2.5 mmol) of 2.66 M NaOEt in ethanol. The solution was stirred overnight at reflux, and the product was precipitated by treatment with 8 mL of 10% aq. HOAC then 2 mL of saturated aq. NaHCO$_3$. The mixture was filtered, and the product was washed with 1:1 MeOH-water then 1:1 ether-hexanes and air dried to afford 232 mg (89%) of 1-(2,4,6-trichlorophenyl)-3-isopropyl-6-(4-(carbethoxy)benzyl)pyrazolo[3,4-d]pyrimidin-4-one as an off-white solid, mp 233–235° C. Mass spec. (ESI+) 519.0754 (M+H)$^+$.

Part E: To a stirred solution of 130 mg -(0.250 mmol) of 1-(2,4,6-trichlorophenyl)-3-isopropyl-6-(4-(carbethoxy)benzyl)pyrazolo[3,4-d]pyrimidin-4-one in 2 mL of THF was added 42 mg (1.0 mmol) of lithium hydroxide hydrate in 2 mL of water followed by 0.25 mL of methanol. The solution was stirred 3.5 h at RT and 10 min. at reflux. The reaction was diluted with ether, and washed twice with 0.1 N aq. NaOH. The combined aq. washings were acidified, and the resulting mixture was extracted with chloroform, then EtOAc. The combined organic extracts were dried (MgSO$_4$) and concentrated under reduced pressure to afford 123 mg (100%) of 1-(2,4,6-trichlorophenyl)-3-isopropyl-6-(4-(carboxy)benzyl)pyrazolo[3,4-d]pyrimidin-4-on as a white solid, mp. 294–295° C.

Part F: To a stirred solution of 49 mg (0.10 mmol) of 1-(2,4,6-trichlorophenyl)-3-isopropyl-6-(4-(carboxy)benzyl)pyrazolo[3,4-d]pyrimidin-4-one and 0.06 mL(0.5 mmol) of 1-amino-4-methylpiperazine in 1 mL of DMF was added 0.052 mL of DIEA followed by 48 mg (0.15 mmol) of TBTU. The solution was stirred 16 h at 45° C., cooled to RT, and poured into water. The mixture was extracted with EtOAc, and the organic extract was concentrated under reduced pressure. Chromatography with 4:1 chloroform-MeOH afforded 34 mg (58%) of 1-(2,4,6-trichlorophenyl)-3-isopropyl-6-(4-(4-methylpiperazin-1-ylaminocarbonyl)benzyl)pyrazolo[3,4-d]pyrimidin-4-on as a white solid. Mass spec: (ESI+) 588(M+H)$^+$.

Example 137

1-(4-(acetamidophenyl-3-yl)-2,6-dichlorophenyl)-3-isopropyl-6-(3-methoxybenzyl)pyrazolo[3,4-d]pyrimidin-4-one A solution of 1-(4-bromo-2,6-dichlorophenyl)-3-isopropyl-6-(3-methoxybenzyl)pyrazolo[3,4-d]pyrimidin-4-one (200 mg, 0.383 mmol) and 3-acetamidobenzeneboronic acid (82 mg, 0.458 mmol) in a 25% solution of ethanol in toluene was stirred at RT under nitrogen for 30 min. Sodium carbonate solution (0.38 mL of a 2N solution, 0.766 mmol) was added followed by tetrabutylammonium bromide (6.1 mg, 0.019 mmol) and tetrakis(triphenylphosphine)palladium(0) (2 mg, catalytic). The reaction was stirred at reflux overnight, cooled to RT, filtered through Celite, washed with EtOAc, and concentrated. Purification by column chromatography using 1:1 hexanes-EtOAc as eluent afforded 114 mg (52%) of the title as a white solid, mp 224–225° C. Mass Spec: 576 (M+H)$^+$.

Example 138

1-(2,6-dichloro-4-formylphenyl)-3-isopropyl-6-(3-methoxybenzyl)pyrazolo[3,4-d]pyrimidin-4-one A two-neck flask was flame-dried, charged with 1-(4-bromo-2,6-dichlorophenyl)-3-isopropyl-6-(3-methoxybenzyl)pyrazolo[3,4-d]pyrimidin-4-one (250 mg, 0.48 mmol) and 4 mL of THF, and placed under an argon atmosphere. The solution was cooled to 0° C. and isopropylmagnesium chloride (0.26 mL, 0.523 mmol) was added dropwise via syringe. The reaction was stirred at –78° C. for 2 min and DMF (0.08 mL, 1.06 mmol) was added via syringe. The reaction was stirred at –78° C. for 15 min and at RT for 30 min. The reaction was quenched with 10% aq. citric acid and extracted with EtOAc. The organic extract was washed with water then brine, dried (MgSO4), and evaporated. Purification by column chromatography on silica gel using 2:1 hexanes-EtOAc as eluent afforded 68 mg (30%) of the title as a white solid, mp 212–214° C. Mass Spec: 469(M–H)$^-$.

Starting from the appropriate 3-substituted 5-amino-1-arylpyrazole-4-carboxamides the following compounds were prepared by methods similiar to those used to synthesize compounds in the examples and tables above:

TABLE VII

| Ex. # | Y | R$^2$ | R$^1$ | mp. (° C.) | MS |
|---|---|---|---|---|---|
| 139 | Cl | Et | 4-Methoxyphenyl | Amorphous | 393 |
| 140 | Cl | Et | 4-Hydroxyphenyl | Amorphous | 379 |
| 141 | Cl | Et | 3-Methoxyphenyl | Amorphous | 393 |
| 142 | Cl | Et | 3-Hydroxyphenyl | Amorphous | 379 |
| 143 | Cl | i-Pr | 3-Hydroxyphenyl | 227–228 | 395 |
| 144 | Cl | i-Pr | 4-Aminophenyl | Amorphous | 394 |
| 145 | Cl | i-Pr | 3-Methoxyphenyl |  | 407 |
| 146 | Cl | i-Pr | 4-Methoxyphenyl | Amorphous | 407 |
| 147 | Cl | i-Pr | 4-Hydroxyphenyl | Amorphous | 395 |
| 148 | Cl | Et | 4-(N,N-dimethylglycinamido)phenylHCl |  | 479 |
| 149 | Cl | SCH$_3$ | 4-Hydroxyphenyl | 243–244 | 397 |
| 150 | Cl | SCH$_3$ | 4-Methoxyphenyl | 227–228 | 413 |
| 151 | Br | Et | 3-Methoxyphenyl | 178–180 | 439 |
| 152 | Br | Et | 4-Aminophenyl | 246–249 | 424 |
| 153 | Br | Et | 3-Hydroxyphenyl | 199–201 | 425 |
| 154 | F | Et | 3-Methoxyphenyl | 193–194 | 379 |
| 155 | F | Et | 3-Hydroxyphenyl | 235–237 | 365 |
| 156 | Br | Et | 4-(N,N-dimethylglycinamido)phenyl | 156–158 | 509 |
| 157 | F | Et | 4-Aminophenyl | 231–233 | 364 |

TABLE VIII

| Ex. # | R$^6$ | R$^7$ | mp. (° C.) | MS |
|---|---|---|---|---|
| 158 | H | CH$_3$NHCH$_2$CH$_2$N(CH$_3$)COCH$_2$ | 154–155 | 541 |
| 159 | H | H$_2$NCH$_2$CH$_2$NHCOCH$_2$ | 140–142 | 513 |
| 160 | H | Piperazin-1-ylCOCH$_2$ | 181–183 | 539 |
| 161 | H | CH$_3$CH$_2$NHCOCH$_2$ | 242–244 | 496 |
| 162 | H | CH$_3$NHCOCH$_2$ | 249–250 | 482 |
| 163 | H | 1-CH$_3$-piperazin-4-ylCOCH$_2$ | 236–237 | 553 |
| 164 | H | (CH$_3$)$_2$NCH$_2$CH$_2$N(CH$_3$)COCH$_2$ | 134–136 | 555 |
| 165 | Cl | 4-CH$_3$-piperazin-1-ylCOCH$_2$ | 205–207 | 587 |

TABLE IX

![Structure: pyrazolo-pyrimidinone with R1-CH2 group, R2 at pyrazole, N-phenyl bearing Cl (ortho), R5 (ortho), R6 (para)]

| Ex. # | R⁵ | R⁶ | R² | R¹ | mp. (° C.) | MS |
|---|---|---|---|---|---|---|
| 166 | Cl | CF₃ | Et | 3-Methoxyphenyl | 192–193 | 497 |
| 167 | Cl | CF₃ | Et | 4-Aminophenyl | 235–236 | 495 |
| 168 | Cl | CF₃ | Et | 4-Methoxyphenyl | 240–241 | 497 |
| 169 | Cl | Br | Et | 4-Hydroxyphenyl | 284–286 | 493 |
| 170 | Cl | Br | Et | 3-Hydroxyphenyl | 242–244 | 495 |
| 171 | Cl | H | Et | 4-Hydroxyphenyl | 262–263 | 413 |
| 172 | Cl | H | Et | 4-Aminoxyphenyl | 159–161 | 414 |
| 173 | Cl | H | Et | 3-Hydroxyphenyl | 242–244 | 413 |
| 174 | Cl | Br | Et | 3-Methoxyphenyl | 232–233 | 507 |
| 175 | Cl | Br | Et | 4-Methoxyphenyl | 252–253 | 507 |
| 176 | Cl | H | Et | 4-Methoxyphenyl | 220–222 | 427 |
| 177 | Cl | H | Et | 3-Methoxyphenyl | 186–187 | 427 |
| 178 | F | H | SCH₃ | 4-Hydroxyphenyl | 267–268 | 415 |
| 179 | F | H | SCH₃ | 3-Hydroxyphenyl | 252–253 | 415 |
| 180 | Cl | Br | SCH₃ | 4-Hydroxyphenyl | 255–256 | 511 |
| 181 | F | H | SCH₃ | 4-Methoxyphenyl | 193–194 | 429 |
| 182 | F | H | SCH₃ | 3-Methoxyphenyl | 244–245 | 431 |
| 183 | Cl | Br | SCH₃ | 4-Methoxyphenyl | 267–268 | 524 |
| 184 | Me | H | Et | 4-Hydroxyphenyl | 255–256 | 395 |
| 185 | Me | Cl | SCH₃ | 4-Methoxyphenyl | 252–255 | 459 |
| 186 | Me | H | SCH₃ | 4-Methoxyphenyl | 233–235 | 425 |
| 187 | Me | Cl | Et | 4-Methoxyphenyl | 245–246 | 441 |
| 188 | Me | Cl | SCH₃ | 4-Hydroxyphenyl | 277–279 | 445 |
| 189 | Me | Cl | Et | 4-Hydroxyphenyl | Amorphous | 429 |
| 190 | Me | H | SCH₃ | 4-Hydroxyphenyl | 264–266 | 413 |
| 191 | Me | H | Et | 4-Methoxyphenyl | 220–221 | 409 |
| 192 | Me | H | Et | 4-Hydroxyphenyl | 257–259 | 395 |
| 193 | Me | H | Et | 3-Methoxyphenyl | 188–190 | 409 |
| 194 | Me | H | Et | 4-Hydroxyphenyl | 255–256 | 395 |
| 195 | Cl | CO₂H | Et | 4-Methoxyphenyl | 292–294 | |
| 196 | Cl | CO₂H | Et | 4-Hydroxyphenyl | 308–310 | 457 |
| 197 | Cl | CO₂H | Et | 3-Methoxyphenyl | Amorphous | 471 |
| 198 | Cl | CO₂H | Et | 3-Hydroxyphenyl | 280–282 | |
| 199 | Me | H | i-Pr | 4-Aminophenyl | 205–206 | 408 |
| 200 | Me | H | i-Pr | 4-(N,N-Dimethylglycinamido)phenyl | 277–279 | 491 |
| 201 | Cl | CONHMe | Et | 4-Methoxyphenyl | 278–280 | 486 |
| 202 | Me | H | Et | 4-Methoxyphenyl | 220–221 | 409 |
| 203 | Me | H | Et | 4-Hydroxyphenyl | 257–259 | 395 |
| 204 | Me | H | Et | 3-Methoxyphenyl | 188–190 | 409 |
| 205 | Cl | CO₂H | Et | 4-Aminophenyl | 226–228 | 458 |
| 206 | Cl | Cl | t-Bu | 3-Hydroxy-4-methoxyphenyl | | 505 |
| 207 | Cl | Cl | CHF₂ | 3-Hydroxy-4-methoxyphenyl | | 499 |
| 208 | Cl | Cl | CH₂OH | 3-Methoxyphenyl | 227–229 | |
| 209 | Cl | Cl | i-Pr | 3-(Ethoxycarbonylmethyl)phenyl | 174–175 | |
| 210 | Cl | Cl | i-Pr | 3-(carboxymethyl)phenyl | 210–211 | |

TABLE IX-continued

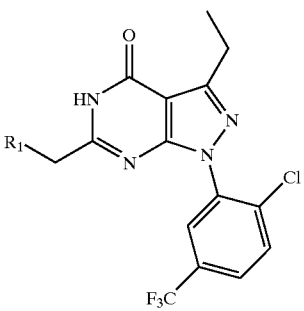

| Ex. # | R⁵ | R⁶ | R² | R¹ | mp. (° C.) | MS |
|---|---|---|---|---|---|---|
| 211 | Cl | Cl | i-Pr | 3-(2-hydroxyethyl)phenyl | | 489 |
| 212 | Cl | Cl | n-Bu | 3-Hydroxy-4-methoxyphenyl | | 505 |
| 213 | Me | H | i-Pr | 4-(1-CH₃-piperidin-4-ylN(CH₃)CH₂CONH)phenyl | | 576 |
| 214 | Me | H | i-Pr | 4-(1-CH₃-piperidin-4-ylN(CH₃)CONH)phenyl | | 562 |
| 215 | Me | Cl | i-Pr | 4-(1-CH₃-piperidin-4-ylN(CH₃)CONH)phenyl | | 596 |
| 216 | Me | Cl | i-Pr | 4-(1-CH₃-piperidin-4-ylN(CH₃)CH₂CONH)phenyl | 108–110 | 610 |
| 217 | Me | Cl | i-Pr | 4-aminophenyl | 212–213 | 442 |
| 218 | Me | Cl | i-Pr | 4-(morpholin-4-ylCONH)phenyl | 256–258 | 555 |
| 219 | Me | Cl | i-Pr | 4-(4-CH₃-piperazin-1-ylCONH)phenyl | 154–156 | 568 |
| 220 | Me | Cl | i-Pr | 4-(4-CH₃-piperazin-1-ylCH₂CONH)phenyl | 199–210 | 582 |
| 221 | Me | Cl | i-Pr | 4-(Me₂NCH₂CONH)phenyl HCl | >300 | 561 |
| 222 | Me | Cl | i-Pr | 4-(morpholin-4-yl CH₂CONH)phenyl | 246–249 | 569 |
| 223 | Cl | Cl | i-Pr | 5-(Me₂NCH₂)-1-methyl pyrrol-2-yl | 182–184 | 507 |
| 224 | Cl | CH₂NH₂ | i-Pr | 3-Methoxyphenyl | | 472 |
| 225 | Cl | SO₂NH₂ | i-Pr | 3-Methoxyphenyl | 244–245 | 520 |

TABLE X

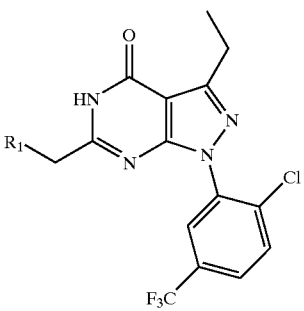

| Ex. # | R¹ | mp. (° C.) | MS |
|---|---|---|---|
| 226 | 4-(N,N-Dimethyl glycinamido)phenyl | 235–237 | 533 |
| 227 | 3-Hydroxyphenyl | 227–229 | 449 |

TABLE XI

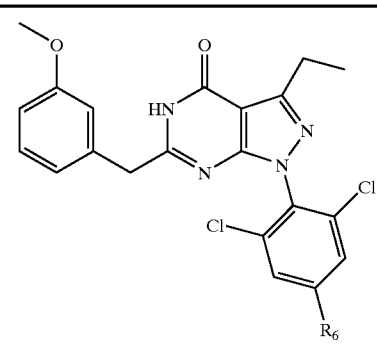

| Ex. # | R⁶ | mp (° C.) | MS |
|---|---|---|---|
| 228 | CONHCH₂CH₂N(CH₃)₂ | 203–205 | 543 |
| 229 | CONHCH₂CH₃ | 229–231 | 512 |
| 230 | CONHCH(CH₃)₂ | 233–235 | 512 |
| 231 | CONHCH₂Ph | 239–240 | 560 |
| 232 | CO-(4-CH₃-piperazin)-1-yl | 128–130 | 555 |
| 233 | CONHCH₂pyridin-3-yl | Amorphous | 563 |
| 234 | CONHCH₂pyridin-2-yl | 188–190 | 563 |
| 235 | CONHCH₂pyridin-4-yl | 238–239 | 563 |
| 236 | CONHCH₂CH₃ | 226–228 | 498 |

TABLE XI-continued

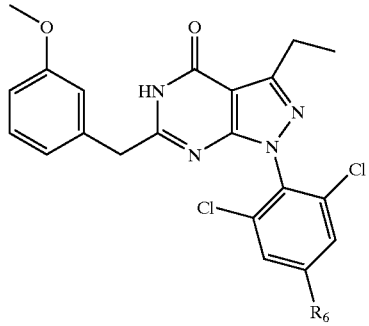

| Ex. # | R⁶ | mp (° C.) | MS |
|---|---|---|---|
| 237 | CONHPh | Amorphous | 546 |
| 238 | CONHC(CH₃)₃ | 222–224 | 528 |
| 239 | CO-piperazin-1-yl | Amorphous | 541 |
| 240 | CONHcyclo-C₃H₅ | 236–239 | 510 |
| 241 | CONHpyridin-3-yl | 256–258 | 549 |
| 242 | CONHpyridin-4-yl | Amorphous | 549 |
| 243 | CCNH(4-CH₃-piperazin)-1-yl | Amorphous | 570 |
| 244 | CONHpyridin-2-yl | 237–239 | 549 |
| 245 | CONHOCH₃ | 204–206 | 502 |

TABLE XII

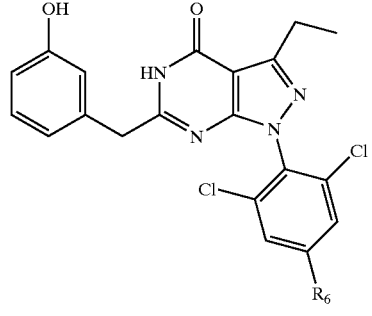

| Ex. # | R⁵ | mp (° C.) | MS |
|---|---|---|---|
| 246 | CONHCH₂CH₂N(CH₃)₂ | 263–265 | 529 |
| 247 | CONHCH₂Ph | 247–249 | 546 |

By reacting a p-substituted aniline with suitable acylating agents and performing further synthetic manipulations as necessary, the following compounds were prepared:

TABLE XIII

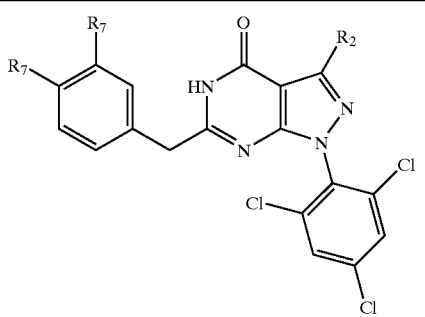

| Ex. # | R² | R⁷ (para) | R⁷ (meta) | mp (° C.) | MS |
|---|---|---|---|---|---|
| 248 | c-Pr | (CH₃)₂NCH₂CONH | H | | 545 |
| 249 | Et | CH₃CONH | H | | 488 |
| 250 | Et | CH₃OCONH | H | | 504 |
| 251 | Et | CH₃NHCONH | H | | 503 |
| 252 | i-Pr | CH₃OCONH | H | | 518 |
| 253 | i-Pr | CH₃OCON(Me) | H | | 532 |
| 254 | Et | (CH₃)₂NCH₂CONH | H | | 531 |
| 255 | i-Pr | CH₃NHCONH | HO | | 535 |
| 256 | i-Pr | CH₃NHCON(Me) | H | 235–237 | 531 |
| 257 | i-Pr | 4-CH₃-piperazin-1-ylN(Me) | H | | 616 |
| 258 | i-Pr | (CH₃)₂NCH₂CON(Me) | H | 235–237 | 561 |
| 259 | i-Pr | CH₃NHCON(Me) | H | 235–237 | 531 |
| 260 | i-Pr | (CH₃)₂NCH₂CONH | HO | 255–258 | 563 |
| 261 | i-Pr | (+/−)-(CH₃)₂NCH(CH₃)CONH | H | | 561 |
| 262 | i-Pr | (CH₃)₂NCH₂CONH | MeO | Amorphous | 577 |
| 263 | i-Pr | CH₃NHCONH | MeO | 258–261 | |
| 264 | i-Pr | imidazol-1-ylCH₂CONH | HO | | 586 |
| 265 | i-Pr | (CH₃)₂NCH₂CONH | H | 255–257 | 547 |
| 266 | i-Pr | 4-CH₃-piperazin-1-yl CH₂CONH | H | | 602 |

TABLE XIII-continued

| Ex. # | R² | R⁷ (para) | R⁷ (meta) | mp (° C.) | MS |
|---|---|---|---|---|---|
| 267 | i-Pr | CH₃NHCONH | H | 268–274 | 519 |
| 268 | i-Pr | Morpholin-4-ylCH₂CONH | H | 252–255 | 589 |
| 269 | i-Pr | Azetidin-1-ylCH₂CONH | H | | 559 |
| 270 | i-Pr | (CH₃)₂NCH₂CH₂SO₂NH | H | | 597.1011 |
| 271 | i-Pr | EtO₂CCH₂NHCONH | H | 229–230 | 589 |
| 272 | i-Pr | Hydantoin-1-yl | H | >300 | 543 |
| 273 | i-Pr | HOCH₂CH₂NHCONH | H | 160–162 | 547.0799 |
| 274 | i-Pr | HO₂C(CH₂)₂CONH | H | 256–258 | 560 |
| 275 | i-Pr | Imidazol-1-ylCH₂CONH | H | 276–278 | 570 |
| 276 | i-Pr | Morpholin-4-ylCH₂CH₂NHCSNH | H | | 634 |
| 277 | i-Pr | HO₂CCH₂NHCONH | H | | 561 |
| 278 | i-Pr | HO₂C(CH₂)₃CONH | H | | 574 |
| 279 | i-Pr | H₂NCH₂CONH | H | >300 | 519 |
| 280 | i-Pr | CH₃NHCH₂CONH | H | Amorphous | 533.1029 |
| 281 | i-Pr | 4-F-phenyl CH₂NHCH₂CONH | H | 217–223 | 627 |
| 282 | i-Pr | Pyrrolidin-1-ylCH₂CONH | H | 235–240 | 573 |
| 283 | i-Pr | pyrid-2-ylCH₂NHCH₂CONH | H | | 610 |
| 284 | i-Pr | pyrid-3-ylCH₂NHCH₂CONH | H | 145–150 | 610 |
| 285 | i-Pr | pyrid-4-ylCH₂NHCH₂CONH | H | 180–185 | 610 |
| 286 | i-Pr | BocNHCH₂CH₂NHCH₂CONH | H | | 662.1829 |
| 287 | i-Pr | HOCH₂CH(CH₂)NHCH₂CONH | H | 190–192 | 577 |
| 288 | i-Pr | CH₃CH(OH)CH₂NHCH₂CONH | | 152–160 | 577 |
| 289 | i-Pr | H₂NCH₂CH₂NHCH₂CONH | H | | 562 |
| 290 | i-Pr | Morpholin-4-ylCH₂CH₂NHCH₂CONH | H | | 632 |
| 291 | i-Pr | 1-CH₃-piperidin-4-yl N(CH₃)CH₂CONH | H | | 630 |
| 292 | i-Pr | (CH₃)₂NCH₂CH₂N(CH₃)CH₂CONH | H | 188–190 | 604 |
| 293 | i-Pr | (CH₃)₂NCH₂CH₂N(CH₃CONH | H | | 590 |
| 294 | i-Pr | (CH₃)₂NCH₂CH₂N(CH₂CONH | OH | | 606 |
| 295 | i-Pr | (CH₃)₂NCH₂CH₂N(CH₃)CH₂CONH | OMe | | 620 |
| 296 | i-Pr | (CH₃)₂NCH(CH₃)CONH | H | | 561 |
| 297 | i-Pr | 1-CH₃-L-prolylNH | H | | |
| 298 | i-Pr | Homopiperazin-1-yl CH₂CONH | H | | 602.1610 |
| 299 | i-Pr | CH₃CH₂NHCH₂CONH | H | | 547 |
| 300 | i-Pr | 4-(H₂NCH₂)piperidin-1-yl CH₂CONH | H | Amorphous | 616 |
| 301 | i-Pr | (CH₃)₂NCH₂CH₂NHCH₂CONH | H | 133–135 | 590.1610 |
| 302 | i-Pr | Cyclo-C₃H₅NHCH₂CONH | H | 213–216 | 559 |
| 303 | i-Pr | Piperidin-4-ylCH₂NH CH₂CONH | H | | 616 |
| 304 | i-Pr | HO(CH₂)₃NHCH₂CONH | H | 200–205 | 575 |
| 305 | i-Pr | 1-Bocpiperidin-4-ylCH₂NH CH₂CONH | H | | 716 |
| 306 | i-Pr | HOCH₂CH₂NHCH₂CONH | H | 210–212 | 563 |
| 307 | i-Pr | Cyclo-C₄H₇NHCH₂CONH | H | 225–228 | 573 |
| 308 | i-Pr | Azetidin-3-ylCONH | H | | 545 |
| 309 | i-Pr | D-prolylNH.HCl | H | 225–226 | 559 |
| 310 | i-Pr | Boc-D-prolylNH | H | | 559.1185 |
| 311 | i-Pr | L-prolylNH.HCl | H | 225–226 | 659.1707 |
| 312 | i-Pr | Boc-L-prolylNH | H | | 657 |
| 313 | i-Pr | Piperidin-1-ylCH₂CH₂NHCH₂CONH | H | 213–215 | 630 |
| 314 | i-Pr | (CH₃)₂CHNHCH₂CONH | H | 130–135 | 559 |
| 315 | i-Pr | BocNHCH₂CH₂CONH | H | | 631 |
| 316 | i-Pr | piperazin-2-yl-CONH | H | Amorphous | 547.1286 |
| 317 | i-Pr | 4-Me-piperazin-2-yl-CONH | H | Amorphous | 588.1448 |
| 318 | i-Pr | piperidin-1-ylNHCONH | H | 264–266 | 588 |
| 319 | i-Pr | H₂NCH₂CH₂NHCONH.F₃CCO₂H | H | | 548 |

TABLE XIII-continued

| Ex. # | R² | R⁷ (para) | R⁷ (meta) | mp (° C.) | MS |
|---|---|---|---|---|---|
| 320 | i-Pr | pyrid-2-ylNHCONH | H | 277–281 | |
| 321 | i-Pr | (CH₃)₂NCH₂CH₂NHCONH | H | 220–222 | 576 |
| 322 | i-Pr | (CH₃)₂NCH₂CH₂NHCONH | OMe | 244–248 | 606 |
| 323 | i-Pr | BocNHCH₂CH₂NHCONH | H | 208–210 | 646 |
| 324 | i-Pr | HO(CH₂)₄NHCONH | H | 208–210 | 577 |
| 325 | i-Pr | (CH₃)₂NNHCONH | H | 240–242 | 546 |
| 326 | i-Pr | (CH₃)₂N(CH₂)₃NHCONH | H | | 590 |
| 327 | i-Pr | (CH₃)₂N(CH₂)₃NHCONH | OMe | 226–228 | 620 |
| 328 | i-Pr | 4-CH₃-homo-piperazin-1-yl-CONH | H | | 602 |
| 329 | i-Pr | CH₃SO₂NHCONH | H | | 581 |
| 330 | i-Pr | CH₃ONHCONH | H | | 534 |
| 331 | i-Pr | 1-CH₃-piperidin-4-yl N(CH₃)CONH | H | | 616 |
| 332 | i-Pr | 1-CH₃-piperidin-4-yl N(CH₃)CONH | OH | | 632 |
| 333 | i-Pr | 1-CH₃-piperidin-4-yl N(CH₃)CONH | OMe | 243–245 | 646 |
| 334 | i-Pr | Tetrahydrofur-2-yl CH₂NHCONH | H | | 587 |
| 335 | i-Pr | CH₃(CH₂)₂CH(OH)CH₂NHCONH | H | | 589 |
| 336 | i-Pr | HOCH₂CH(CH₃)NHCONH | H | 156–158 | 561 |
| 337 | i-Pr | CH₃CH(OH)CH₂NHCONH | H | | 561 |
| 338 | i-Pr | HOCH₂CH₂NHCONH | H | 222–225 | 547 |
| 339 | i-Pr | Morpholin-4-ylNHCONH | H | 272–274 | 588 |
| 340 | i-Pr | (CH₃)₂NCH(CH₃)CH₂NHCONH | H | | 590 |
| 341 | i-Pr | 4-CH₃-piperazin-1-yl NHCONH | H | | 603 |
| 342 | i-Pr | 4-CH₃-piperazin-1-yl NHCONH | OH | | 619 |
| 343 | i-Pr | 4-CH₃-piperazin-1-yl NHCONH | OMe | 245–246 | 633 |
| 344 | i-Pr | Morpholin-4-yl CH₂CH₂NHCONH | H | | 618 |
| 345 | i-Pr | 4-CH₃-piperazin-1-ylCONH | H | | 588 |
| 346 | i-Pr | Piperazin-1-ylCONH.HCl | H | | 574 |
| 347 | Et | 4-CH₃-piperazin-1-ylCONH | H | | 574 |
| 348 | Et | (CH₃)₂NCH₂CH₂NHCONH | H | | 563 |
| 349 | Et | pyrid-2-ylNHCONH | H | Amorphous | 582 |
| 350 | Et | pyrid-4-ylNHCONH | H | Amorphous | 582 |
| 351 | i-Pr | H | MeNHCONHCH₂ | | 533 |
| 352 | i-Pr | (+/−)-2-(Me₂NCH₂)piperid-1-ylCONH | H | | 630 |

TABLE XIII-continued

| Ex. # | R² | R⁷ (para) | R⁷ (meta) | mp (° C.) | MS |
|---|---|---|---|---|---|
| 353 | i-Pr | (+/−)-2-(Me₂NCH₂)piperid-1-ylCONH.CF₃CO₂H | OH | | 646 |
| 354 | i-Pr | (+/−)-2-(Me₂NCH₂)piperid-1-ylCONH | OMe | 131–135 | 660 |
| 355 | i-Pr | CH₃NCH₂CH₂N(CH₃)CONH | OMe | 146–148 | 606 |
| 356 | i-Pr | (CH₃)₂NCH₂CH₂NCO | H | 278–280 | 561 |
| 357 | i-Pr | (CH₃)NCH₂CH₂N(CH₃)CO | H | | 561 |
| 358 | i-Pr | (CH₃)₂NCH₂CH₂N(CH₃)CO | H | | 575 |

Following procedures similar to those used to synthesize the examples above, the following compounds were prepared or could be prepared:

TABLE XIV

| Ex. # | R² | R⁷ (para) | R⁷ (meta) | MS |
|---|---|---|---|---|
| 1 | i-Pr | Pyrrolidin-1-ylCH₂CH₂NHCH₂CONH | H | 616 |
| 2 | i-Pr | Pyrrolidin-1-ylCH₂CH₂NHCONH | OMe | 632 |
| 3 | i-Pr | pyrrolidin-1-ylCH₂CH₂NHCONH | OH | 618 |
| 4 | i-Pr | pyrrolidin-1-ylCH₂CH₂NHCONH | H | 602 |
| 5 | i-Pr | 2-CH₃-piperazin-1-ylCONH | H | |
| 6 | i-Pr | 3-CH₃-piperazin-1-ylCH₂CONH | H | 602 |
| 7 | i-Pr | trans-2,5-di-CH₃-piperazin-1-ylCH₂CONH | H | 616 |
| 8 | i-Pr | cis-2,6-di-CH₃-piperazin-1-ylCH₂CONH | H | |
| 9 | i-Pr | cis-3,4-di-CH₃-piperazin-1-ylCH₂CONH | H | 616 |
| 10 | i-Pr | cis-3,5-di-CH₃-piperazin-1-ylCH₂CONH | H | |
| 11 | i-Pr | trans-2,6-di-CH₃-piperazin-1-ylCH₂CONH | H | |
| 12 | i-Pr | trans-3,5-di-CH₃-piperazin-1-ylCH₂CONH | H | |

TABLE XIV-continued

| Ex. # | R² | R⁷ (para) | R⁷ (meta) | MS |
|---|---|---|---|---|
| 13 | i-Pr | (R)-1-Ethylpyrrolidin-2-ylCH₂NHCONH | H | |
| 14 | i-Pr | (S)-1-Ethylpyrrolidin-2-ylCH₂NHCONH | H | |
| 15 | i-Pr | 5-CH₃-pyrazin-2-ylCH₂NHCH₂CONH | H | |
| 16 | i-Pr | (CH₃)₂NCH₂CH₂CH₂OCONH | H | 591 |
| 17 | i-Pr | (+/−)-N—(CH₃)piperidin-3-ylCH₂OCONH | H | 617 |
| 18 | i-Pr | (+/−)-N—(CH₃)piperidin-3-ylOCONH | H | 603 |
| 19 | i-Pr | (+/−)-N—(CH₃)piperidin-2-ylCH₂OCONH | H | 617 |
| 20 | i-Pr | (+/−)-N—(CH₃)piperidin-3-ylOCONH | H | 589 |
| 21 | i-Pr | 2-CH₃-piperazin-1-ylCONH | H | |
| 22 | i-Pr | pyrrolidin-1-ylCH₂CH₂NHCH₂CONH | H | |
| 23 | i-Pr | (CH₃)₂NCH₂CH₂N(CH₃)CONH | H | 590 |
| 24 | i-Pr | (CH₃)₂NCH₂CH₂N(CH₃)CO | H | 575 |
| 25 | i-Pr | 2-CH₃-piperazin-1-ylCONH | H | |
| 26 | i-Pr | 3-CH₃-piperazin-1-ylCH₂CONH | H | |
| 27 | i-Pr | trans-2,5-di-CH₃-piperazin-1-ylCH₂CONH | H | |
| 28 | i-Pr | cis-2,6-di-CH₃-piperazin-1-ylCH₂CONH | H | |
| 29 | i-Pr | cis-3,5-di-CH₃-piperazin-1-ylCH₂CONH | H | |
| 30 | i-Pr | trans-2,6-di-CH₃-piperazin-1-ylCH₂CONH | H | |

TABLE XV (a) Structure: R7-substituted phenol with 4-hydroxy group, linked via CH2 to a pyrazolo[3,4-d]pyrimidin-4(5H)-one core bearing R2 at position 3 and 2,4,6-trichlorophenyl at N1.

(b) Structure: R7-substituted phenyl with 3-methoxy group, linked via CH2 to a pyrazolo[3,4-d]pyrimidin-4(5H)-one core bearing R2 at position 3 and 2,4,6-trichlorophenyl at N1.

| Ex. # | R² | R⁷ |
|---|---|---|
| 1 | i-Pr | 1-CH₃-piperazin-4-ylCH₂CONH |
| 2 | i-Pr | BocNHSO₂NH |
| 3 | i-Pr | Morpholin-4-ylCH₂CONH |
| 4 | i-Pr | Azetidin-1-ylCH₂CONH |
| 5 | i-Pr | (CH₃)₂NCH₂CH₂SO₂NH |
| 6 | i-Pr | EtO₂CCH₂NHCONH |
| 7 | i-Pr | HOCH₂CH₂NHCONH |
| 8 | i-Pr | Hydantoin-1-yl |
| 9 | i-Pr | HOCH₂CH₂NHCONH |
| 10 | i-Pr | HO₂C(CH₂)₂CONH |
| 11 | i-Pr | imidazol-1-ylCH₂CONH |
| 12 | i-Pr | Morpholin-4-ylCH₂CH₂NHCSNH |
| 13 | i-Pr | HO₂CCH₂NHCONH |
| 14 | i-Pr | HO₂C(CH₂)₃CONH |
| 15 | i-Pr | (CH₃)₂NCH₂CONH |
| 16 | i-Pr | H₂NCH₂CONH |
| 17 | i-Pr | CH₃NHCH₂CONH |
| 18 | i-Pr | 4-F-phenylCH₂NHCH₂CONH |
| 19 | i-Pr | pyrrolidin-1-ylCH₂CONH |
| 20 | i-Pr | pyrid-2-ylCH₂NHCH₂CONH |
| 21 | i-Pr | pyrid-3-ylCH₂NHCH₂CONH |
| 22 | i-Pr | pyrid-4-ylCH₂NHCH₂CONH |
| 23 | i-Pr | BocNHCH₂CH₂NHCH₂CONH |
| 24 | i-Pr | HOCH₂CH(CH₃)NHCH₂CONH |
| 25 | i-Pr | CH₃CH(OH)CH₂NHCH₂CONH |
| 26 | i-Pr | H₂NCH₂CH₂NHCH₂CONH |
| 27 | i-Pr | morpholin-4-ylCH₂CH₂NHCH₂CONH |
| 28 | i-Pr | 1-CH₃-piperidin-4-ylN(CH₃)CH₂CONH |
| 29 | i-Pr | (CH₃)₂NCH₂CH₂N(CH₃)CH₂CONH |
| 30 | i-Pr | piperazin-1-ylCH₂CONH |
| 31 | i-Pr | (CH₃)₂NCH(CH₃)CONH |
| 32 | i-Pr | 1-CH₃-L-prolylNH |
| 33 | i-Pr | Homopiperazin-1-ylCH₂CONH |
| 34 | i-Pr | CH₃CH₂NHCH₂CONH |
| 35 | i-Pr | 4-(CH₂NH₂)piperidin-1-ylCH₂CONH |
| 36 | i-Pr | (CH₃)₂NCH₂CH₂NHCH₂CONH |
| 37 | i-Pr | H₂NCH₂CONH |
| 38 | i-Pr | cyclo-C₃H₅NHCH₂CONH |
| 39 | i-Pr | piperidin-4-ylCH₂NHCH₂CONH |
| 40 | i-Pr | HO(CH₂)₃NHCH₂CONH |
| 41 | i-Pr | 1-Bocpiperidin-4-ylCH₂NHCH₂CONH |
| 42 | i-Pr | HOCH₂CH₂NHCH₂CONH |
| 43 | i-Pr | cyclo-C₄H₇NHCH₂CONH |
| 44 | i-Pr | azetidin-3-ylCONH |
| 45 | i-Pr | D-prolylNH.HCl |
| 46 | i-Pr | Boc-D-prolylNH |
| 47 | i-Pr | L-prolylNH.HCl |
| 48 | i-Pr | Boc-L-prolylNH |
| 49 | i-Pr | piperidin-1-ylCH₂CH₂NHCH₂CONH |
| 50 | i-Pr | (CH₃)₂CHNHCH₂CONH |
| 51 | i-Pr | BocNHCH₂CH₂CONH |
| 52 | i-Pr | pyrrolidin-1-ylCH₂CH₂NHCH₂CONH |
| 53 | i-Pr | 2-CH₃-piperazin-1-ylCONH |
| 54 | i-Pr | 3-CH₃-piperazin-1-ylCH₂CONH |
| 55 | i-Pr | trans-2,5-di-CH₃-piperazin-1-ylCH₂CONH |
| 56 | i-Pr | cis-2,6-di-CH₃-piperazin-1-ylCH₂CONH |
| 57 | i-Pr | cis-3,5-di-CH₃-piperazin-1-ylCH₂CONH |
| 58 | i-Pr | trans-2,6-di-CH₃-piperazin-1-ylCH₂CONH |
| 59 | i-Pr | trans-3,5-di-CH₃-piperazin-1-ylCH₂CONH |
| 60 | i-Pr | (R)-1-Ethylpyrrolidin-2-ylCH₂NHCONH |
| 61 | i-Pr | (S)-1-Ethylpyrrolidin-2-ylCH₂NHCONH |
| 62 | i-Pr | 5-CH₃-pyrazin-2-ylCH₂NHCH₂ CONH |
| 63 | i-Pr | piperazin-2-yl-CONH |
| 64 | i-Pr | 4-Me-piperazin-2-ylCONH |

TABLE XVI (a) Structure: R7-substituted phenyl (with H on ring) linked via CH2 to pyrazolo[3,4-d]pyrimidin-4(5H)-one core with R2 and 2,4,6-trichlorophenyl.

(b) Structure: R7-substituted 4-hydroxyphenyl linked via CH2 to pyrazolo[3,4-d]pyrimidin-4(5H)-one core with R2 and 2,4,6-trichlorophenyl.

(c) Structure: R7-substituted 3-methoxyphenyl linked via CH2 to pyrazolo[3,4-d]pyrimidin-4(5H)-one core with R2 and 2,4,6-trichlorophenyl.

| Ex. # | R² | R⁷ |
|---|---|---|
| 1 | Cyc-Bu | (CH₃)₂NCH₂CONH |
| 2 | Cyc-Bu | 1-CH₃-piperazin-4-ylCH₂CONH |
| 3 | Cyc-Bu | CH₃NHCONH |
| 4 | Cyc-Bu | Morpohlin-4-ylCH₂CONH |
| 5 | Cyc-Bu | Azetidin-1-ylCH₂CONH |
| 6 | Cyc-Bu | (CH₃)₂NCH₂CH₂SO₂NH |

TABLE XVI-continued

| | | |
|---|---|---|
| 7 | Cyc-Bu | EtO$_2$CCH$_2$NHCONH |
| 8 | Cyc-Bu | Hydantoin-1-yl |
| 9 | Cyc-Bu | HOCH$_2$CH$_2$NHCONH |
| 10 | Cyc-Bu | HO$_2$C(CH$_2$)$_2$CONH |
| 11 | Cyc-Bu | imidazol-1-ylCH$_2$CONH |
| 12 | Cyc-Bu | Morpholin-4-ylCH$_2$CH$_2$NHCSNH |
| 13 | Cyc-Bu | HO$_2$CCH$_2$NHCONH |
| 14 | Cyc-Bu | HO$_2$C(CH$_2$)$_3$CONH |
| 15 | Cyc-Bu | H$_2$NCH$_2$CONH |
| 16 | Cyc-Bu | CH$_3$NHCH$_2$CONH |
| 17 | Cyc-Bu | 4-F-phenylCH$_2$NHCH$_2$CONH |
| 18 | Cyc-Bu | pyrrolidin-1-ylCH$_2$CONH |
| 19 | Cyc-Bu | pyrid-2-ylCH$_2$NHCH$_2$CONH |
| 20 | Cyc-Bu | pyrid-3-ylCH$_2$NHCH$_2$CONH |
| 21 | Cyc-Bu | pyrid-4-ylCH$_2$NHCH$_2$CONH |
| 22 | Cyc-Bu | BocNHCH$_2$CH$_2$NHCH$_2$CONH |
| 23 | Cyc-Bu | HOCH$_2$CH(CH$_3$)NHCH$_2$CONH |
| 24 | Cyc-Bu | CH$_3$CH(OH)CH$_2$NHCH$_2$CONH |
| 25 | Cyc-Bu | H$_2$NCH$_2$CH$_2$NHCH$_2$CONH |
| 26 | Cyc-Bu | morpholin-4-ylCH$_2$CH$_2$NHCH$_2$CONH |
| 27 | Cyc-Bu | 1-CH$_3$-piperidin-4-ylN(CH$_3$)CH$_2$CONH |
| 28 | Cyc-Bu | (CH$_3$)$_2$NCH$_2$CH$_2$N(CH$_3$)CH$_2$CONH |
| 29 | Cyc-Bu | (CH$_3$)$_2$NCH(CH$_3$)CONH |
| 30 | Cyc-Bu | 1-CH$_3$-L-prolylNH |
| 31 | Cyc-Bu | Homopiperazin-1-ylCH$_2$CONH |
| 32 | Cyc-Bu | CH$_3$CH$_2$NHCH$_2$CONH |
| 33 | Cyc-Bu | 4-(CH$_2$NH$_2$)piperidin-1-ylCH$_2$CONH |
| 34 | Cyc-Bu | (CH$_3$)$_2$NCH$_2$CH$_2$NHCH$_2$CONH |
| 35 | Cyc-Bu | cyclo-C$_3$H$_5$NHCH$_2$CONH |
| 36 | Cyc-Bu | Piperidin-4-ylCH$_2$NHCH$_2$CONH |
| 37 | Cyc-Bu | HO(CH$_2$)$_3$NHCH$_2$CONH |
| 38 | Cyc-Bu | 1-Bocpiperidin-4-ylCH$_2$NHCH$_2$CONH |
| 39 | Cyc-Bu | HOCH$_2$CH$_2$NHCH$_2$CONH |
| 40 | Cyc-Bu | cyclo-C$_4$H$_7$NHCH$_2$CONH |
| 41 | Cyc-Bu | azetidin-3-ylCONH |
| 42 | Cyc-Bu | D-prolylNH.HCl |
| 43 | Cyc-Bu | Boc-D-prolylNH |
| 44 | Cyc-Bu | L-prolylNH.HCl |
| 45 | Cyc-Bu | Boc-L-prolylNH |
| 46 | Cyc-Bu | piperidin-1-ylCH$_2$CH$_2$NHCH$_2$CONH |
| 47 | Cyc-Bu | (CH$_3$)$_2$CHNHCH$_2$CONH |
| 48 | Cyc-Bu | BocNHCH$_2$CH$_2$CONH |
| 49 | Cyc-Bu | piperazin-2-yl-CONH |
| 50 | Cyc-Bu | 4-Me-piperazin-2-yl-CONH |
| 51 | Cyc-Bu | piperidin-1-ylNHCONH |
| 52 | Cyc-Bu | H$_2$NCH$_2$CH$_2$NHCONH.F$_3$CCO$_2$H |
| 53 | Cyc-Bu | pyrid-2-ylNHCONH |
| 54 | Cyc-Bu | (CH$_3$)$_2$NCH$_2$CH$_2$NHCONH |
| 55 | Cyc-Bu | BocNHCH$_2$CH$_2$NHCONH |
| 56 | Cyc-Bu | HO(CH$_2$)$_4$NHCONH |
| 57 | Cyc-Bu | (CH$_3$)$_2$NNHCONH |
| 58 | Cyc-Bu | (CH$_3$)$_2$N(CH$_2$)$_3$NHCONH |
| 59 | Cyc-Bu | 1-CH$_3$-homopiperazin-4-yl-CONH |
| 60 | Cyc-Bu | CH$_3$SO$_2$NHCONH |
| 61 | Cyc-Bu | CH$_3$ONHCONH |
| 62 | Cyc-Bu | (CH$_3$)$_2$NCH$_2$CH$_2$NHCONH |
| 63 | Cyc-Bu | 1-CH$_3$-piperidin-4-ylN(CH$_3$)CONH |
| 64 | Cyc-Bu | tetrahydrofur-2-ylCH$_2$NHCONH |
| 65 | Cyc-Bu | CH$_3$(CH$_2$)$_2$CH(OH)CH$_2$NHCONH |
| 66 | Cyc-Bu | HOCH$_2$CH(CH$_3$)NHCONH |
| 67 | Cyc-Bu | CH$_3$CH(OH)CH$_2$NHCONH |
| 68 | Cyc-Bu | HOCH$_2$CH$_2$NHCONH |
| 69 | Cyc-Bu | morpholin-4-ylNHCONH |
| 70 | Cyc-Bu | (CH$_3$)$_2$NCH(CH$_3$)CH$_2$NHCONH |
| 71 | Cyc-Bu | 1-CH$_3$-piperazin-4-ylNHCONH |
| 72 | Cyc-Bu | morpholin-4-ylCH$_2$CH$_2$CONH |
| 73 | Cyc-Bu | 1-CH$_3$-piperazin-4-ylCONH |
| 74 | Cyc-Bu | pyrid-2-ylNHCONH |
| 75 | Cyc-Bu | pyrid-4-ylNHCONH |
| 76 | Cyc-Bu | pyrrolidin-1-ylCH$_2$CH$_2$NHCH$_2$CONH |
| 77 | Cyc-Bu | 2-CH$_3$-piperazin-1-ylCONH |
| 78 | Cyc-Bu | 3-CH$_3$-piperazin-1-ylCH$_2$CONH |
| 79 | Cyc-Bu | trans-2,5-di-CH$_3$-ipiperazin-1-ylCH$_2$CONH |
| 80 | Cyc-Bu | cis-2,6-di-CH$_3$-piperazin-1-ylCH$_2$CONH |
| 81 | Cyc-Bu | cis-3,5-di-CH$_3$-piperazin-1-ylCH$_2$CONH |
| 82 | Cyc-Bu | trans-2,6-di-CH$_3$-piperazin-1-ylCH$_2$CONH |
| 83 | Cyc-Bu | trans-3,5-di-CH$_3$-piperazin-1-ylCH$_2$CONH |
| 84 | Cyc-Bu | (R)-1-Ethylpyrrolidin-2-ylCH$_2$NHCONH |
| 85 | Cyc-Bu | (S)-1-Ethylpyrrolidin-2-ylCH$_2$NHCONH |
| 86 | Cyc-Bu | 5-CH$_3$-pyrazin-2-ylCH$_2$NHCH$_2$CONH |

TABLE XVII

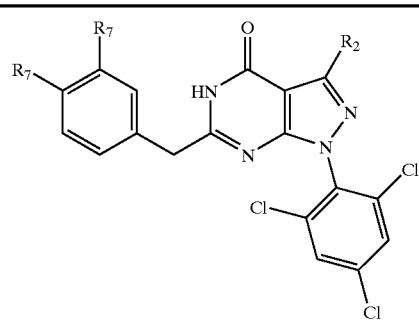

| Ex. # | R$^2$ | R$^7$ (para) | R$^7$ (meta) |
|---|---|---|---|
| 1 | i-Pr | (CH$_3$)$_2$NCH$_2$CONH | Me |
| 2 | i-Pr | 1-CH$_3$-piperazin-4-ylCH$_2$CONH | Me |
| 3 | i-Pr | CH$_3$NHCONH | Me |
| 4 | i-Pr | Morpholin-4-ylCH$_2$CONH | Me |
| 5 | i-Pr | Azetidin-1-ylCH$_2$CONH | Me |
| 6 | i-Pr | (CH$_3$)$_2$NCH$_2$CH$_2$SO$_2$NH | Me |
| 7 | i-Pr | EtO$_2$CCH$_2$NHCONH | Me |
| 8 | i-Pr | Hydantoin-1-yl | Me |
| 9 | i-Pr | HOCH$_2$CH$_2$NHCONH | Me |
| 10 | i-Pr | HO$_2$C(CH$_2$)$_2$CONH | Me |
| 11 | i-Pr | imidazol-1-ylCH$_2$CONH | Me |
| 12 | i-Pr | Morpholin-4-ylCH$_2$CH$_2$NHCSNH | Me |
| 13 | i-Pr | HO$_2$CCH$_2$NHCONH | Me |
| 14 | i-Pr | HO$_2$C(CH$_2$)$_3$CONH | Me |
| 15 | i-Pr | H$_2$NCH$_2$CONH | Me |
| 16 | i-Pr | CH$_3$NHCH$_2$CONH | Me |
| 17 | i-Pr | 4-F-phenylCH$_2$NHCH$_2$CONH | Me |
| 18 | i-Pr | pyrrolidin-1-ylCH$_2$CONH | Me |
| 19 | i-Pr | pyrid-2-ylCH$_2$NHCH$_2$CONH | Me |
| 20 | i-Pr | pyrid-3-ylCH$_2$NHCH$_2$CONH | Me |
| 21 | i-Pr | pyrid-4-ylCH$_2$NHCH$_2$CONH | Me |
| 22 | i-Pr | BocNHCH$_2$CH$_2$NHCH$_2$CONH | Me |
| 23 | i-Pr | HOCH$_2$CH(CH$_3$)NHCH$_2$CONH | Me |
| 24 | i-Pr | CH$_3$CH(OH)CH$_2$NHCH$_2$CONH | Me |
| 25 | i-Pr | H$_2$NCH$_2$CH$_2$NHCH$_2$CONH | Me |
| 26 | i-Pr | morpholin-4-ylCH$_2$CH$_2$NHCH$_2$CONH | Me |
| 27 | i-Pr | 1-CH$_3$-piperidin-4-ylN(CH$_3$)CH$_2$CONH | Me |
| 28 | i-Pr | (CH$_3$)$_2$NCH$_2$CH$_2$N(CH$_3$)CH$_2$CONH | Me |
| 29 | i-Pr | (CH$_3$)$_2$NCH(CH$_3$)CONH | Me |
| 30 | i-Pr | 1-CH$_3$-L-prolylNH | Me |
| 31 | i-Pr | Homopiperazin-1-ylCH$_2$CONH | Me |
| 32 | i-Pr | CH$_3$CH$_2$NHCH$_2$CONH | Me |
| 33 | i-Pr | 4-(CH$_2$NH$_2$)piperidin-1-ylCH$_2$CONH | Me |
| 34 | i-Pr | (CH$_3$)$_2$NCH$_2$CH$_2$NHCH$_2$CONH | Me |
| 35 | i-Pr | cyclo-C$_3$H$_5$NHCH$_2$CONH | Me |
| 36 | i-Pr | Piperidin-4-ylCH$_2$NHCH$_2$CONH | Me |
| 37 | i-Pr | HO(CH$_2$)$_3$NHCH$_2$CONH | Me |
| 38 | i-Pr | 1-Bocpiperidin-4-ylCH$_2$NHCH$_2$CONH | Me |
| 39 | i-Pr | HOCH$_2$CH$_2$NHCH$_2$CONH | Me |
| 40 | i-Pr | cyclo-C$_4$H$_7$NHCH$_2$CONH | Me |
| 41 | i-Pr | azetidin-3-ylCONH | Me |
| 42 | i-Pr | D-prolylNH.HCl | Me |
| 43 | i-Pr | Boc-D-prolylNH | Me |
| 44 | i-Pr | L-prolylNH.HCl | Me |
| 45 | i-Pr | Boc-L-prolylNH | Me |
| 46 | i-Pr | piperidin-1-ylCH$_2$CH$_2$NHCH$_2$CONH | Me |
| 47 | i-Pr | (CH$_3$)$_2$CHNHCH$_2$CONH | Me |
| 48 | i-Pr | BocNHCH$_2$CH$_2$CONH | Me |
| 49 | i-Pr | piperazin-2-yl-CONH | Me |
| 50 | i-Pr | 4-Me-piperazin-2-yl-CONH | Me |
| 51 | i-Pr | piperidin-1-ylNHCONH | Me |
| 52 | i-Pr | H$_2$NCH$_2$CH$_2$NHCONH.F$_3$CCO$_2$H | Me |
| 53 | i-Pr | pyrid-2-ylNHCONH | Me |
| 54 | i-Pr | (CH$_3$)$_2$NCH$_2$CH$_2$NHCONH | Me |
| 55 | i-Pr | BocNHCH$_2$CH$_2$NHCONH | Me |

TABLE XVII-continued

| Ex. # | R² | R⁷ (para) | R⁷ (meta) |
|---|---|---|---|
| 56 | i-Pr | HO(CH₂)₄NHCONH | Me |
| 57 | i-Pr | (CH₃)₂NNHCONH | Me |
| 58 | i-Pr | (CH₃)₂N(CH₂)₃NHCONH | Me |
| 59 | i-Pr | 1-CH₃-homopiperazin-4-yl-CONH | Me |
| 60 | i-Pr | CH₃SO₂NHCONH | Me |
| 61 | i-Pr | CH₃ONHCONH | Me |
| 62 | i-Pr | (CH₃)₂NCH₂CH₂NHCONH | Me |
| 63 | i-Pr | 1-CH₃-piperidin-4-ylN(CH₃)CONH | Me |
| 64 | i-Pr | Tetrahydrofur-2-ylCH₂NHCONH | Me |
| 65 | i-Pr | CH₃(CH₂)₂CH(OH)CH₂NHCONH | Me |
| 66 | i-Pr | HOCH₂CH(CH₃)NHCONH | Me |
| 67 | i-Pr | CH₃CH(OH)CH₂NHCONH | Me |
| 68 | i-Pr | HOCH₂CH₂NHCONH | Me |
| 69 | i-Pr | morpholin-4-ylNHCONH | Me |
| 70 | i-Pr | (CH₃)₂NCH(CH₃)CH₂NHCONH | Me |
| 71 | i-Pr | 1-CH₃-piperazin-4-ylNHCONH | Me |
| 72 | i-Pr | morpholin-4-ylCH₂CH₂NHCONH | Me |
| 73 | i-Pr | 1-CH₃-piperazin-4-ylCONH | Me |
| 74 | i-Pr | pyrid-2-ylNHCONH | Me |
| 75 | i-Pr | pyrid-4-ylNHCONH | Me |
| 76 | i-Pr | Pyrrolidin-1-ylCH₂CH₂NHCH₂CONH | Me |
| 77 | i-Pr | 2-CH₃-piperazin-1-ylCONH | Me |
| 78 | i-Pr | 3-CH₃-piperazin-1-ylCH₂CONH | Me |
| 79 | i-Pr | trans-2,5-di-CH₃-piperazin-1-ylCH₂CONH | Me |
| 80 | i-Pr | cis-2,6-di-CH₃-piperazin-1-ylCH₂CONH | Me |
| 81 | i-Pr | cis-3,5-di-CH₃-piperazin-1-ylCH₂CONH | Me |
| 82 | i-Pr | trans-2,6-di-CH₃-piperazin-1-ylCH₂CONH | Me |
| 83 | i-Pr | trans-3,5-di-CH₃-piperazin-1-ylCH₂CONH | Me |
| 84 | i-Pr | (R)-1-Ethylpyrrolidin-2-ylCH₂NHCONH | Me |
| 85 | i-Pr | (S)-1-Ethylpyrrolidin-2-ylCH₂NHCONH | Me |
| 86 | i-Pr | 5-CH₃-pyrazin-2-ylCH₂NHCH₂CONH | Me |

TABLE XVIII

| Ex. # | R² | R⁷ (meta) | R⁷ (ortho) |
|---|---|---|---|
| 1 | i-Pr | 1-CH₃-piperazin-4-ylCH₂CONH | Me |
| 2 | i-Pr | CH₃NHCONH | Me |
| 3 | i-Pr | morpholin-4-ylCH₂CONH | Me |
| 4 | i-Pr | azetidin-1-ylCH₂CONH | Me |
| 5 | i-Pr | (CH₃)₂NCH₂CH₂SO₂NH | Me |
| 6 | i-Pr | EtO₂CCH₂NHCONH | Me |
| 7 | i-Pr | Hydantoin-1-yl | Me |
| 8 | i-Pr | HOCH₂CH₂NHCONH | Me |
| 9 | i-Pr | HO₂C(CH₂)₂CONH | Me |
| 10 | i-Pr | imidazol-1-ylCH₂CONH | Me |
| 11 | i-Pr | Morpholin-4-ylCH₂CH₂NHCSNH | Me |
| 12 | i-Pr | HO₂CCH₂NHCONH | Me |
| 13 | i-Pr | HO₂C(CH₂)₃CONH | Me |
| 14 | i-Pr | H₂NCH₂CONH | Me |
| 15 | i-Pr | CH₃NHCH₂CONH | Me |
| 16 | i-Pr | 4-F-phenylCH₂NHCH₂CONH | Me |
| 17 | i-Pr | pyrrolidin-1-ylCH₂CONH | Me |
| 18 | i-Pr | pyrid-2-ylCH₂NHCH₂CONH | Me |
| 19 | i-Pr | pyrid-3-ylCH₂NHCH₂CONH | Me |
| 20 | i-Pr | pyrid-4-ylCH₂NHCH₂CONH | Me |
| 21 | i-Pr | BocNHCH₂CH₂NHCONH | Me |
| 22 | i-Pr | HOCH₂CH(CH₃)NHCH₂CONH | Me |
| 23 | i-Pr | CH₃CH(OH)CH₂NHCH₂CONH | Me |
| 24 | i-Pr | H₂NCH₂CH₂NHCH₂CONH | Me |
| 25 | i-Pr | morpholin-4-ylCH₂CH₂NHCH₂CONH | Me |
| 26 | i-Pr | 1-CH₃-piperidin-4-ylN(CH₃)CH₂CONH | Me |
| 27 | i-Pr | (CH₃)₂NCH₂CH₂N(CH₃)CH₂CONH | Me |
| 28 | i-Pr | (CH₃)₂NCH(CH₃)CONH | Me |
| 29 | i-Pr | 1-CH₃-L-prolylNH | Me |
| 30 | i-Pr | Homopiperazin-1-ylCH₂CONH | Me |
| 31 | i-Pr | CH₃CH₂NHCH₂CONH | Me |
| 32 | i-Pr | 4-(CH₃NH₂)piperidin-1-ylCH₂CONH | Me |
| 33 | i-Pr | (CH₃)₂NCH₂CH₂NHCH₂CONH | Me |
| 34 | i-Pr | cyclo-C₃H₅NHCH₂CONH | Me |
| 35 | i-Pr | Piperidin-4-ylCH₂NHCONH | Me |
| 36 | i-Pr | HO(CH₂)₃NHCH₂CONH | Me |
| 37 | i-Pr | 1-Bocpiperidin-4-ylCH₂NHCH₂CONH | Me |
| 38 | i-Pr | HOCH₂CH₂NHCH₂CONH | Me |
| 39 | i-Pr | cyclo-C₄H₇NHCH₂CONH | Me |
| 40 | i-Pr | azetidin-3-ylCONH | Me |
| 41 | i-Pr | D-prolylNH.HCl | Me |
| 42 | i-Pr | Boc-D-prolylNH | Me |
| 43 | i-Pr | L-prolylNH.HCl | Me |
| 44 | i-Pr | Boc-L-prolylNH | Me |
| 45 | i-Pr | piperidin-1-ylCH₂CH₂NHCH₂CONH | Me |
| 46 | i-Pr | (CH₃)₂CHNHCH₂CONH | Me |
| 47 | i-Pr | BocNHCH₂CH₂CONH | Me |
| 48 | i-Pr | piperazin-2-yl-CONH | Me |
| 49 | i-Pr | 4-Me-piperazin-2-yl-CONH | Me |
| 50 | i-Pr | piperidin-1-ylNHCONH | Me |
| 51 | i-Pr | H₂NCH₂CH₂NHCONH.F₃CCO₂H | Me |
| 52 | i-Pr | pyrid-2-ylNHCONH | Me |
| 53 | i-Pr | (CH₃)₂NCH₂CH₂NHCONH | Me |
| 54 | i-Pr | BocNHCH₂CH₂NHCONH | Me |
| 55 | i-Pr | HO(CH₂)₄NHCONH | Me |
| 56 | i-Pr | (CH₃)₂NNHCONH | Me |
| 57 | i-Pr | (CH₃)₂N(CH₂)₃NHCONH | Me |
| 58 | i-Pr | 1-CH₃-homopiperazin-4-yl-CONH | Me |
| 59 | i-Pr | CH₃SO₂NHCONH | Me |
| 60 | i-Pr | CH₃ONHCONH | Me |
| 61 | i-Pr | (CH₃)₂NCH₂CH₂NHCONH | Me |
| 62 | i-Pr | 1-CH₃-piperidin-4-ylN(CH₃)CONH | Me |
| 63 | i-Pr | tetrahydrofur-2-ylCH₂NHCONH | Me |
| 64 | i-Pr | CH₃(CH₂)₂CH(OH)CH₂NHCONH | Me |
| 65 | i-Pr | HOCH₂CH(CH₃)NHCONH | Me |
| 66 | i-Pr | CH₃CH(OH)CH₂NHCONH | Me |

TABLE XVIII-continued

Structure: pyrazolo-pyrimidinone core with R7 (meta) and R7 (ortho) on benzyl phenyl, R2 on pyrazole, and 2,4,6-trichlorophenyl on N1.

| Ex. # | R² | R⁷ (meta) | R⁷ (ortho) |
|---|---|---|---|
| 67 | i-Pr | HOCH₂CH₂NHCONH | Me |
| 68 | i-Pr | morpholin-4-ylNHCONH | Me |
| 69 | i-Pr | (CH₃)₂NCH(CH₃)CH₂NHCONH | Me |
| 70 | i-Pr | 1-CH₃-piperazin-4-ylNHCONH | Me |
| 71 | i-Pr | morpholin-4-ylCH₂CH₂NHCONH | Me |
| 72 | i-Pr | 1-CH₃-piperazin-4-ylCONH | Me |
| 73 | i-Pr | pyrid-2-ylNHCONH | Me |
| 74 | i-Pr | pyrid-4-ylNHCONH | Me |
| 75 | i-Pr | Pyrrolidin-1-ylCH₂CH₂NHCH₂CONH | Me |
| 76 | i-Pr | 2-CH₃-piperazin-1-ylCONH | Me |
| 77 | i-Pr | 3-CH₃-piperazin-1-ylCH₂CONH | Me |
| 78 | i-Pr | trans-2,5-di-CH₃-piperazin-1-ylCH₂CONH | Me |
| 79 | i-Pr | cis-2,6-di-CH₃-piperazin-1-ylCH₂CONH | Me |
| 80 | i-Pr | cis-3,5-di-CH₃-piperazin-1-ylCH₂CONH | Me |
| 81 | i-Pr | trans-2,6-di-CH₃-piperazin-1-ylCH₂CONH | Me |
| 82 | i-Pr | trans-3,5-di-CH₃-piperazin-1-ylCH₂CONH | Me |
| 83 | i-Pr | (R)-1-Ethylpyrrolidin-2-ylCH₂NHCONH | Me |
| 84 | i-Pr | (S)-1-Ethylpyrrolidin-2-ylCH₂NHCONH | Me |
| 85 | i-Pr | 5-CH₃-pyrazin-2-ylCH₂NHCH₂CONH | Me |

TABLE XIX

Structure: pyrazolo-pyrimidinone core with R7 (para) and R7 (ortho) on benzyl phenyl, R2 on pyrazole, and 2,4,6-trichlorophenyl on N1.

| Ex. # | R² | R⁷ (para) | R⁷ (ortho) |
|---|---|---|---|
| 1 | i-Pr | (CH₃)₂NCH₂CONH | Me |
| 2 | i-Pr | 1-CH₃-piperazin-4-ylCH₂CONH | Me |
| 3 | i-Pr | CH₃NHCONH | Me |
| 4 | i-Pr | Morpholin-4-ylCH₂CONH | Me |
| 5 | i-Pr | Azetidin-1-ylCH₂CONH | Me |
| 6 | i-Pr | (CH₃)₂NCH₂CH₂SO₂NH | Me |
| 7 | i-Pr | EtO₂CCH₂NHCONH | Me |
| 8 | i-Pr | Hydantoin-1-yl | Me |
| 9 | i-Pr | HOCH₂CH₂NHCONH | Me |
| 10 | i-Pr | HO₂C(CH₂)₂CONH | Me |
| 11 | i-Pr | Imidazol-1-ylCH₂CONH | Me |
| 12 | i-Pr | Morpholin-4-ylCH₂CH₂NHCSNH | Me |
| 13 | i-Pr | HO₂CCH₂NHCONH | Me |
| 14 | i-Pr | HO₂C(CH₂)₃CONH | Me |
| 15 | i-Pr | H₂NCH₂CONH | Me |
| 16 | i-Pr | CH₃NHCH₂CONH | Me |
| 17 | i-Pr | 4-F-phenylCH₂NHCH₂CONH | Me |

TABLE XIX-continued

| Ex. # | R² | R⁷ (para) | R⁷ (ortho) |
|---|---|---|---|
| 18 | i-Pr | pyrrolidin-1-ylCH₂CONH | Me |
| 19 | i-Pr | pyrid-2-ylCH₂NHCH₂CONH | Me |
| 20 | i-Pr | pyrid-3-ylCH₂NHCH₂CONH | Me |
| 21 | i-Pr | pyrid-4-ylCH₂NHCH₂CONH | Me |
| 22 | i-Pr | BocNHCH₂CH₂NHCH₂CONH | Me |
| 23 | i-Pr | HOCH₂CH(CH₃)NHCH₂CONH | Me |
| 24 | i-Pr | CH₃CH(OH)CH₂NHCH₂CONH | Me |
| 25 | i-Pr | H₂NCH₂CH₂NHCH₂CONH | Me |
| 26 | i-Pr | morpholin-4-ylCH₂CH₂NHCH₂CONH | Me |
| 27 | i-Pr | 1-CH₃-piperidin-4-ylN(CH₃)CH₂CONH | Me |
| 28 | i-Pr | (CH₃)₂NCH₂CH₂N(CH₃)CH₂CONH | Me |
| 29 | i-Pr | (CH₃)₂NCH(CH₃)CONH | Me |
| 30 | i-Pr | 1-CH₃-L-prolylNH | Me |
| 31 | i-Pr | Homopiperazin-1-ylCH₂CONH | Me |
| 32 | i-Pr | CH₃NHCH₂CH₂CONH | Me |
| 33 | i-Pr | 4-(CH₂NH₂)piperidin-1-ylCH₂CONH | Me |
| 34 | i-Pr | (CH₃)₂NCH₂CH₂NHCONH | Me |
| 35 | i-Pr | cyclo-C₃H₅NHCH₂CONH | Me |
| 36 | i-Pr | Piperidin-4-ylCH₂NHCH₂CONH | Me |
| 37 | i-Pr | HO(CH₂)₃NHCH₂CONH | Me |
| 38 | i-Pr | 1-Bocpiperidin-4-ylCH₂NHCH₂CONH | Me |
| 39 | i-Pr | HOCH₂CH₂NHCH₂CONH | Me |
| 40 | i-Pr | cyclo-C₄H₇NHCH₂CONH | Me |
| 41 | i-Pr | azetidin-3-ylCONH | Me |
| 42 | i-Pr | D-prolylNH.HCl | Me |
| 43 | i-Pr | Boc-D-prolylNH | Me |
| 44 | i-Pr | L-prolylNH.HCl | Me |
| 45 | i-Pr | Boc-L-prolylNH | Me |
| 46 | i-Pr | piperidin-1-ylCH₂CH₂NHCH₂CONH | Me |
| 47 | i-Pr | (CH₃)₂CHNHCH₂CONH | Me |
| 48 | i-Pr | BocNHCH₂CH₂CONH | Me |
| 49 | i-Pr | piperazin-2-yl-CONH | Me |
| 50 | i-Pr | 4-Me-piperazin-2-yl-CONH | Me |
| 51 | i-Pr | piperidin-1-ylNHCONH | Me |
| 52 | i-Pr | H₂NCH₂CH₂NHCONH.F₃CCO₂H | Me |
| 53 | i-Pr | pyrid-2-ylNHCONH | Me |
| 54 | i-Pr | (CH₃)₂NCH₂CH₂NHCONH | Me |
| 55 | i-Pr | BocNHCH₂CH₂NHCONH | Me |
| 56 | i-Pr | HO(CH₂)₄NHCONH | Me |
| 57 | i-Pr | (CH₃)₂NNHCONH | Me |
| 58 | i-Pr | (CH₃)₂N(CH₂)₃NHCONH | Me |
| 59 | i-Pr | 1-CH₃-homopiperazin-4-yl-CONH | Me |
| 60 | i-Pr | CH₃SO₂NHCONH | Me |
| 61 | i-Pr | CH₃ONHCONH | Me |
| 62 | i-Pr | (CH₃)₂NCH₂CH₂NHCONH | Me |
| 63 | i-Pr | 1-CH₃-piperidin-4-ylN(CH₃)CONH | Me |
| 64 | i-Pr | tetrahydrofur-2-ylCH₂NHCONH | Me |
| 65 | i-Pr | CH₃(CH₂)₂CH(OH)CH₂NHCONH | Me |
| 66 | i-Pr | HOCH₂CH(CH₃)NHCONH | Me |
| 67 | i-Pr | CH₃CH(OH)CH₂NHCONH | Me |
| 68 | i-Pr | HOCH₂CH₂NHCONH | Me |
| 69 | i-Pr | morpholin-4-ylNHCONH | Me |
| 70 | i-Pr | (CH₃)₂NCH(CH₃)CH₂NHCONH | Me |
| 71 | i-Pr | 1-CH₃-piperazin-4-ylNHCONH | Me |
| 72 | i-Pr | morpholin-4-ylCH₂CH₂NHCONH | Me |
| 73 | i-Pr | 1-CH₃-piperazin-4-ylCONH | Me |
| 74 | i-Pr | pyrid-2-ylNHCONH | Me |
| 75 | i-Pr | pyrid-4-ylNHCONH | Me |
| 76 | i-Pr | pyrrolidin-1-ylCH₂CH₂NHCONH | Me |
| 77 | i-Pr | 2-CH₃-piperazin-1-ylCONH | Me |

TABLE XIX-continued

[Structure: pyrazolopyrimidinone with R2, benzyl bearing R7 (para) and R7 (ortho), N-linked 2,4,6-trichlorophenyl]

| Ex. # | R² | R⁷ (para) | R⁷ (ortho) |
|---|---|---|---|
| 78 | i-Pr | 3-CH₃-piperazin-1-ylCH₂CONH | Me |
| 79 | i-Pr | trans-2,5-di-CH₃-piperazin-1-ylCH₂CONH | Me |
| 80 | i-Pr | cis-2,6-di-CH₃-piperazin-1-ylCH₂CONH | Me |
| 81 | i-Pr | cis-3,5-di-CH₃-piperazin-1-ylCH₂CONH | Me |
| 82 | i-Pr | trans-2,6-di-CH₃-piperazin-1-ylCH₂CONH | Me |
| 83 | i-Pr | trans-3,5-di-CH₃-piperazin-1-ylCH₂CONH | Me |
| 84 | i-Pr | (R)-1-Ethylpyrrolidin-2-ylCH₂NHCONH | Me |
| 85 | i-Pr | (S)-1-Ethylpyrrolidin-2-ylCH₂NHCONH | Me |
| 86 | i-Pr | 5-CH₃-pyrazin-2-ylCH₂NHCH₂CONH | Me |

TABLE XX (a) [Structure with H at ortho, R7 at para]
(b) [Structure with OH at ortho, R7 at para]
(c) [Structure with OMe at ortho, R7 at para]

TABLE XX-continued

| Ex. # | R² | R⁷ |
|---|---|---|
| 1 | Et | 1-CH₃-piperazin-4-ylCH₂CONH |
| 2 | Et | CH₃NHCONH |
| 3 | Et | Morpholin-4-ylCH₂CONH |
| 4 | Et | Azetidin-1-ylCH₂CONH |
| 5 | Et | (CH₃)₂NCH₂CH₂SO₂NH |
| 6 | Et | EtO₂CCH₂NHCONH |
| 7 | Et | Hydantoin-1-yl |
| 8 | Et | HOCH₂CH₂NHCONH |
| 9 | Et | HO₂C(CH₂)₂CONH |
| 10 | Et | Imidazol-1-ylCH₂CONH |
| 11 | Et | Morpholin-4-ylCH₂CH₂NHCSNH |
| 12 | Et | HO₂CCH₂NHCONH |
| 13 | Et | HO₂C(CH₂)₃CONH |
| 14 | Et | H₂NCH₂CONH |
| 15 | Et | CH₃NHCH₂CONH |
| 16 | Et | 4-F-phenylCH₂NHCH₂CONH |
| 17 | Et | pyrrolidin-1-ylCH₂CONH |
| 18 | Et | pyrid-2-ylCH₂NHCH₂CONH |
| 19 | Et | pyrid-3-ylCH₂NHCH₂CONH |
| 20 | Et | pyrid-4-ylCH₂NHCH₂CONH |
| 21 | Et | BocNHCH₂CH₂NHCH₂CONH |
| 22 | Et | HOCH₂CH(CH₃)NHCH₂CONH |
| 23 | Et | CH₃CH(OH)CH₂NHCH₂CONH |
| 24 | Et | H₂NCH₂CH₂NHCH₂CONH |
| 25 | Et | morpholin-4-ylCH₂CH₂NHCH₂CONH |
| 26 | Et | 1-CH₃-piperidin-4-ylN(CH₃)CH₂CONH |
| 27 | Et | (CH₃)₂NCH₂CH₂N(CH₃)CH₂CONH |
| 28 | Et | (CH₃)₂NCH(CH₃)CONH |
| 29 | Et | 1-CH₃-L-prolylNH |
| 30 | Et | Homopiperazin-1-ylCH₂CONH |
| 31 | Et | CH₃CH₂NHCH₂CONH |
| 32 | Et | 4-(CH₂NH₂)piperidin-1-ylCH₂CONH |
| 33 | Et | (CH₃)₂NCH₂CH₂NHCH₂CONH |
| 34 | Et | cyclo-C₃H₅NHCH₂CONH |
| 35 | Et | Piperidin-4-ylCH₂NHCH₂CONH |
| 36 | Et | HO(CH₂)₃NHCH₂CONH |
| 37 | Et | 1-BocpiperIdin-4-ylCH₂NHCH₂CONH |
| 38 | Et | HOCH₂CH₂NHCH₂CONH |
| 39 | Et | cyclo-C₄H₇NHCH₂CONH |
| 40 | Et | azetidin-3-ylCONH |
| 41 | Et | D-prolylNH.HCl |
| 42 | Et | Boc-D-prolylNH |
| 43 | Et | L-prolylNH.HCl |
| 44 | Et | Boc-L-prolylNH |
| 45 | Et | piperidin-1-ylCH₂CH₂NHCH₂CONH |
| 46 | Et | (CH₃)₂CHNHCH₂CONH |
| 47 | Et | BocNHCH₂CH₂CONH |
| 48 | Et | piperazin-2-yl-CONH |
| 49 | Et | 4-Me-piperazin-2-yl-CONH |
| 50 | Et | piperidin-1-ylNHCONH |
| 51 | Et | H₂NCH₂CH₂NHCONH.F₃CCO₂H |
| 52 | Et | pyrid-2-ylNHCONH |
| 53 | Et | (CH₃)₂NCH₂CH₂NHCONH |
| 54 | Et | BocNHCH₂CH₂NHCONH |
| 55 | Et | HO(CH₂)₄NHCONH |
| 56 | Et | (CH₃)₂NNHCONH |
| 57 | Et | (CH₃)₂N(CH₂)₃NHCONH |
| 58 | Et | 1-CH₃-homopiperazin-4-yl-CONH |
| 59 | Et | CH₃SO₂NHCONH |
| 60 | Et | CH₃ONHCONH |
| 61 | Et | (CH₃)₂NCH₂CH₂NHCONH |
| 62 | Et | 1-CH₃-piperidin-4-ylN(CH₃)CONH |
| 63 | Et | Tetrahydrofur-2-ylCH₂NHCONH |
| 64 | Et | CH₃(CH₂)₂CH(OH)CH₂NHCONH |
| 65 | Et | HOCH₂CH(CH₃)NHCONH |
| 66 | Et | CH₃CH(OH)CH₂NHCONH |
| 67 | Et | HOCH₂CH₂NHCONH |
| 68 | Et | morpholin-4-ylNHCONH |
| 69 | Et | (CH₃)₂NCH(CH₃)CH₂NHCONH |
| 70 | Et | 1-CH₃-piperazin-4-ylNHCONH |
| 71 | Et | morpholin-4-ylCH₂CH₂NHCONH |
| 72 | Et | 1-CH₃-piperazin-4-ylCONH |
| 73 | Et | pyrid-2-ylNHCONH |
| 74 | Et | pyrid-4-ylNHCONH |
| 75 | Et | pyrrolidin-1-ylCH₂CH₂NHCH₂CONH |
| 76 | Et | 2-CH₃-piperazin-1-ylCONH |

TABLE XX-continued

| | | |
|---|---|---|
| 77 | Et | 3-$CH_3$-piperazin-1-yl$CH_2$CONH |
| 78 | Et | trans-2,5-di-$CH_3$-piperazin-1-yl$CH_2$CONH |
| 79 | Et | cis-2,6-di-$CH_3$-piperazin-1-yl$CH_2$CONH |
| 80 | Et | cis-3,5-di-$CH_3$-piperazin-1-yl$CH_2$CONH |
| 81 | Et | trans-2,6-di-$CH_3$-piperazin-1-yl$CH_2$CONH |
| 82 | Et | trans-3,5-di-$CH_3$-piperazin-1-yl$CH_2$CONH |
| 83 | Et | (R)-1-Ethylpyrrolidin-2-yl$CH_2$NHCONH |
| 84 | Et | (S)-1-Ethylpyrrolidin-2-yl$CH_2$NHCONH |
| 85 | Et | 5-$CH_3$-pyrazin-2-yl$CH_2$NHCH$_2$CONH |

TABLE XXI

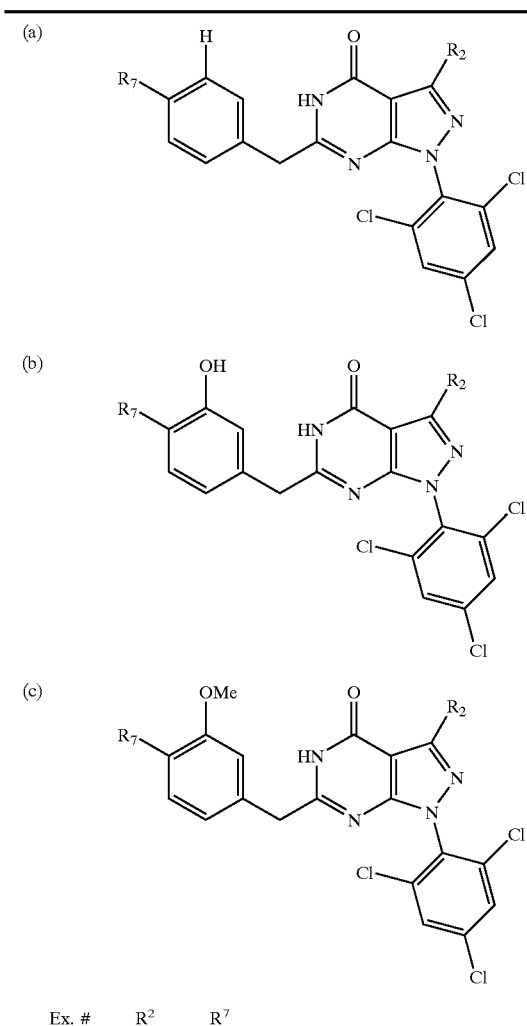

| Ex. # | $R^2$ | $R^7$ |
|---|---|---|
| 1 | cyc-Pr | 1-$CH_3$-piperazin-4-yl$CH_2$CONH |
| 2 | cyc-Pr | $CH_3$NHCONH |
| 3 | cyc-Pr | Morpholin-4-yl$CH_2$CONH |
| 4 | cyc-Pr | Azetidin-1-yl$CH_2$CONH |
| 5 | cyc-Pr | $(CH_3)_2$N$CH_2CH_2SO_2$NH |
| 6 | cyc-Pr | EtO$_2$CC$H_2$NHCONH |
| 7 | cyc-Pr | Hydantoin-1-yl |
| 8 | cyc-Pr | HOC$H_2$C$H_2$NHCONH |
| 9 | cyc-Pr | HO$_2$C(C$H_2$)$_2$CONH |
| 10 | cyc-Pr | Imidazol-1-yl$CH_2$CONH |
| 11 | cyc-Pr | Morpholin-4-yl$CH_2CH_2$NHCSNH |
| 12 | cyc-Pr | HO$_2$CC$H_2$NHCONH |
| 13 | cyc-Pr | HO$_2$C(C$H_2$)$_3$CONH |
| 14 | cyc-Pr | $H_2$NC$H_2$CONH |
| 15 | cyc-Pr | $CH_3$NHC$H_2$CONH |
| 16 | cyc-Pr | 4-F-phenylC$H_2$NHC$H_2$CONH |
| 17 | cyc-Pr | pyrrolidin-1-yl$CH_2$CONH |
| 18 | cyc-Pr | pyrid-2-yl$CH_2$NHC$H_2$CONH |
| 19 | cyc-Pr | pyrid-3-yl$CH_2$NHC$H_2$CONH |
| 20 | cyc-Pr | pyrid-4-yl$CH_2$NHC$H_2$CONH |
| 21 | cyc-Pr | BocNHC$H_2CH_2$NHC$H_2$CONH |
| 22 | cyc-Pr | HOC$H_2$CH($CH_3$)NHC$H_2$CONH |
| 23 | cyc-Pr | $CH_3$CH(OH)C$H_2$NHC$H_2$CONH |
| 24 | cyc-Pr | $H_2$NC$H_2CH_2$NHC$H_2$CONH |
| 25 | cyc-Pr | morpholin-4-yl$CH_2CH_2$NHC$H_2$CONH |
| 26 | cyc-Pr | 1-$CH_3$-piperidin-4-ylN($CH_3$)C$H_2$CONH |
| 27 | cyc-Pr | $(CH_3)_2$NC$H_2CH_2$N($CH_3$)C$H_2$CONH |
| 28 | cyc-Pr | $(CH_3)_2$NCH($CH_3$)CONH |
| 29 | cyc-Pr | 1-$CH_3$-L-prolylNH |
| 30 | cyc-Pr | Homopiperazin-1-yl$CH_2$CONH |
| 31 | cyc-Pr | $CH_3CH_2$NHC$H_2$CONH |
| 32 | cyc-Pr | 4-($CH_2$NH$_2$)piperidin-1-yl$CH_2$CONH |
| 33 | cyc-Pr | $(CH_3)_2$NC$H_2CH_2$NHC$H_2$CONH |
| 34 | cyc-Pr | cyclo-$C_3H_5$NHC$H_2$CONH |
| 35 | cyc-Pr | Piperidin-4-yl$CH_2$NHC$H_2$CONH |
| 36 | cyc-Pr | HO(C$H_2$)$_3$NHC$H_2$CONH |
| 37 | cyc-Pr | 1-Bocpiperidin-4-yl$CH_2$NHC$H_2$CONH |
| 38 | cyc-Pr | HOC$H_2$C$H_2$NHC$H_2$CONH |
| 39 | cyc-Pr | cyclo-$C_4H_7$NHC$H_2$CONH |
| 40 | cyc-Pr | azetidin-3-ylCONH |
| 41 | cyc-Pr | D-prolylNH.HCl |
| 42 | cyc-Pr | Boc-D-prolylNH |
| 43 | cyc-Pr | L-prolylNH.HCl |
| 44 | cyc-Pr | Boc-L-prolylNH |
| 45 | cyc-Pr | piperidin-1-yl$CH_2CH_2$NHC$H_2$CONH |
| 46 | cyc-Pr | $(CH_3)_2$CHNHC$H_2$CONH |
| 47 | cyc-Pr | BocNHC$H_2$C$H_2$CONH |
| 48 | cyc-Pr | piperazin-2-yl-CONH |
| 49 | cyc-Pr | 4-Me-piperazin-2-yl-CONH |
| 50 | cyc-Pr | piperidin-1-ylNHCONH |
| 51 | cyc-Pr | $H_2$NC$H_2CH_2$NHCONH.$F_3$CCO$_2$H |
| 52 | cyc-Pr | pyrid-2-ylNHCONH |
| 53 | cyc-Pr | $(CH_3)_2$NC$H_2CH_2$NHCONH |
| 54 | cyc-Pr | BocNHC$H_2CH_2$NHCONH |
| 55 | cyc-Pr | HO(C$H_2$)$_4$NHCONH |
| 56 | cyc-Pr | $(CH_3)_2$NNHCONH |
| 57 | cyc-Pr | $(CH_3)_2$N(C$H_2$)$_3$NHCONH |
| 58 | cyc-Pr | 1-$CH_3$-homopiperazin-4-yl-CONH |
| 59 | cyc-Pr | $CH_3SO_2$NHCONH |
| 60 | cyc-Pr | $CH_3$ONHCONH |
| 61 | cyc-Pr | $(CH_3)_2$NC$H_2CH_2$NHCONH |
| 62 | cyc-Pr | 1-$CH_3$-piperidin-4-ylN($CH_3$)CONH |
| 63 | cyc-Pr | tetrahydrofur-2-yl$CH_2$NHCONH |
| 64 | cyc-Pr | $CH_3(CH_2)_2$CH(OH)C$H_2$NHCONH |
| 65 | cyc-Pr | HOC$H_2$CH($CH_3$)NHCONH |
| 66 | cyc-Pr | $CH_3$CH(OH)C$H_2$NHCONH |
| 67 | cyc-Pr | HOC$H_2$C$H_2$NHCONH |
| 68 | cyc-Pr | morpholin-4-ylNHCONH |
| 69 | cyc-Pr | $(CH_3)_2$NCH($CH_3$)C$H_2$NHCONH |
| 70 | cyc-Pr | 1-$CH_3$-piperazin-4-ylNHCONH |
| 71 | cyc-Pr | morpholin-4-yl$CH_2CH_2$NHCONH |
| 72 | cyc-Pr | 1-$CH_3$-piperazin-4-ylCONH |
| 73 | cyc-Pr | pyrid-2-ylNHCONH |
| 74 | cyc-Pr | pyrid-4-ylNHCONH |
| 75 | cyc-Pr | pyrrolidin-1-yl$CH_2CH_2$NHCONH |
| 76 | cyc-Pr | 2-$CH_3$-piperazin-1-ylCONH |
| 77 | cyc-Pr | 3-$CH_3$-piperazin-1-yl$CH_2$CONH |
| 78 | cyc-Pr | trans-2,5-di-$CH_3$-piperazin-1-yl$CH_2$CONH |
| 79 | cyc-Pr | cis-2,6-di-$CH_3$-piperazin-1-yl$CH_2$CONH |
| 80 | cyc-Pr | cis-3,5-di-$CH_3$-piperazin-1-yl$CH_2$CONH |
| 81 | cyc-Pr | trans-2,6-di-$CH_3$-piperazin-1-yl$CH_2$CONH |
| 82 | cyc-Pr | trans-3,5-di-$CH_3$-piperazin-1-yl$CH_2$CONH |
| 83 | cyc-Pr | (R)-1-Ethylpyrrolidin-2-yl$CH_2$NHCONH |
| 84 | cyc-Pr | (S)-1-Ethylpyrrolidin-2-yl$CH_2$NHCONH |
| 85 | cyc-Pr | 5-$CH_3$-pyrazin-2-yl$CH_2$NHC$H_2$CONH |

TABLE XXII (a) Structure with H on phenyl, R7, pyrazolopyrimidinone core with R2, N-linked 2,4,6-trichlorophenyl.

(b) Structure with OH on phenyl, R7, same core.

(c) Structure with OMe on phenyl, R7, same core.

| Ex. # | R² | R⁷ |
|---|---|---|
| 1 | 1-Methylcyc-Pr | 1-CH₃-piperazin-4-ylCH₂CONH |
| 2 | 1-Methylcyc-Pr | CH₃NHCONH |
| 3 | 1-Methylcyc-Pr | Morpholin-4-ylCH₂CONH |
| 4 | 1-Methylcyc-Pr | Azetidin-1-ylCH₂CONH |
| 5 | 1-Methylcyc-Pr | (CH₃)₂NCH₂CH₂SO₂NH |
| 6 | 1-Methylcyc-Pr | EtO₂CCH₂NHCONH |
| 7 | 1-Methylcyc-Pr | Hydantoin-1-yl |
| 8 | 1-Methylcyc-Pr | HOCH₂CH₂NHCONH |
| 9 | 1-Methylcyc-Pr | HO₂C(CH₂)₂CONH |
| 10 | 1-Methylcyc-Pr | Imidazol-1-ylCH₂CONH |
| 11 | 1-Methylcyc-Pr | Morpholin-4-ylCH₂CH₂NHCSNH |
| 12 | 1-Methylcyc-Pr | HO₂CCH₂NHCONH |
| 13 | 1-Methylcyc-Pr | HO₂C(CH₂)₃CONH |
| 14 | 1-Methylcyc-Pr | H₂NCH₂CONH |
| 15 | 1-Methylcyc-Pr | CH₃NHCH₂CONH |
| 16 | 1-Methylcyc-Pr | 4-F-phenylCH₂NHCH₂CONH |
| 17 | 1-Methylcyc-Pr | Pyrrolidin-1-ylCH₂CONH |
| 18 | 1-Methylcyc-Pr | Pyrid-2-ylCH₂NHCH₂CONH |
| 19 | 1-Methylcyc-Pr | Pyrid-3-ylCH₂NHCH₂CONH |
| 20 | 1-Methylcyc-Pr | Pyrid-4-ylCH₂NHCH₂CONH |
| 21 | 1-Methylcyc-Pr | BocNHCH₂CH₂NHCH₂CONH |
| 22 | 1-Methylcyc-Pr | HOCH₂CH(CH₃)NHCH₂CONH |
| 23 | 1-Methylcyc-Pr | CH₃CH(OH)CH₂NHCH₂CONH |
| 24 | 1-Methylcyc-Pr | H₂NCH₂CH₂NHCH₂CONH |
| 25 | 1-Methylcyc-Pr | Morpholin-4-ylCH₂CH₂NHCH₂CONH |
| 26 | 1-Methylcyc-Pr | 1-CH₃-piperidin-4-ylN(CH₃)CH₂CONH |
| 27 | 1-Methylcyc-Pr | (CH₃)₂NCH₂CH₂N(CH₃)CH₂CONH |
| 28 | 1-Methylcyc-Pr | (CH₃)₂NCH(CH₃)CONH |
| 29 | 1-Methylcyc-Pr | 1-CH₃-L-prolylNH |
| 30 | 1-Methylcyc-Pr | Homopiperazin-1-ylCH₂CONH |
| 31 | 1-Methylcyc-Pr | CH₃CH₂NHCH₂CONH |
| 32 | 1-Methylcyc-Pr | 4-(CH₂NH₂)piperidin-1-ylCH₂CONH |
| 33 | 1-Methylcyc-Pr | (CH₃)₂NCH₂CH₂NHCH₂CONH |
| 34 | 1-Methylcyc-Pr | Cyclo-C₃H₅NHCH₂CONH |
| 35 | 1-Methylcyc-Pr | Piperidin-4-ylCH₂NHCH₂CONH |
| 36 | 1-Methylcyc-Pr | HO(CH₂)₃NHCH₂CONH |
| 37 | 1-Methylcyc-Pr | 1-Bocpiperidin-4-ylCH₂NHCH₂CONH |
| 38 | 1-Methylcyc-Pr | HOCH₂CH₂NHCH₂CONH |
| 39 | 1-Methylcyc-Pr | Cyclo-C₄H₇NHCH₂CONH |
| 40 | 1-Methylcyc-Pr | Azetidin-3-ylCONH |
| 41 | 1-Methylcyc-Pr | D-prolylNH.HCl |
| 42 | 1-Methylcyc-Pr | Boc-D-prolylNH |
| 43 | 1-Methylcyc-Pr | L-prolylNH.HCl |
| 44 | 1-Methylcyc-Pr | Boc-L-prolylNH |
| 45 | 1-Methylcyc-Pr | Piperidin-1-ylCH₂CH₂NHCH₂CONH |
| 46 | 1-Methylcyc-Pr | (CH₃)₂CHNHCH₂CONH |
| 47 | 1-Methylcyc-Pr | BocNHCH₂CH₂CONH |
| 48 | 1-Methylcyc-Pr | Piperazin-2-yl-CONH |
| 49 | 1-Methylcyc-Pr | 4-Me-piperazin-2-yl-CONH |
| 50 | 1-Methylcyc-Pr | Piperidin-1-ylNHCONH |
| 51 | 1-Methylcyc-Pr | H₂NCH₂CH₂NHCONH.F₃CCO₂H |
| 52 | 1-Methylcyc-Pr | Pyrid-2-ylNHCONH |
| 53 | 1-Methylcyc-Pr | (CH₃)₂NCH₂CH₂NHCONH |
| 54 | 1-Methylcyc-Pr | BocNHCH₂CH₂NHCONH |
| 55 | 1-Methylcyc-Pr | HO(CH₂)₄NHCONH |
| 56 | 1-Methylcyc-Pr | (CH₃)₂NNHCONH |
| 57 | 1-Methylcyc-Pr | (CH₃)₂N(CH₂)₃NHCONH |
| 58 | 1-Methylcyc-Pr | 1-CH₃-homopiperazin-4-yl-CONH |
| 59 | 1-Methylcyc-Pr | CH₃SO₂NHCONH |
| 60 | 1-Methylcyc-Pr | CH₃ONHCONH |
| 61 | 1-Methylcyc-Pr | (CH₃)₂NCH₂CH₂NHCONH |
| 62 | 1-Methylcyc-Pr | 1-CH₃-piperidin-4-ylN(CH₃)CONH |
| 63 | 1-Methylcyc-Pr | Tetrahydrofur-2-ylCH₂NHCONH |
| 64 | 1-Methylcyc-Pr | CH₃(CH₂)₂CH(OH)CH₂NHCONH |
| 65 | 1-Methylcyc-Pr | HOCH₂CH(CH₃)NHCONH |
| 66 | 1-Methylcyc-Pr | CH₃CH(OH)CH₂NHCONH |
| 67 | 1-Methylcyc-Pr | HOCH₂CH₂NHCONH |
| 68 | 1-Methylcyc-Pr | Morpholin-4-ylNHCONH |
| 69 | 1-Methylcyc-Pr | (CH₃)₂NCH(CH₃)CH₂NHCONH |
| 70 | 1-Methylcyc-Pr | 1-CH₃-piperazin-4-ylNHCONH |
| 71 | 1-Methylcyc-Pr | Morpholin-4-ylCH₂CH₂NHCONH |
| 72 | 1-Methylcyc-Pr | 1-CH₃-piperazin-4-ylCONH |
| 73 | 1-Methylcyc-Pr | Pyrid-2-ylNHCONH |
| 74 | 1-Methylcyc-Pr | Pyrid-4-ylNHCONH |
| 75 | 1-Methylcyc-Pr | Pyrrolidin-1-ylCH₂CH₂NHCH₂CONH |
| 76 | 1-Methylcyc-Pr | 2-CH₃-piperazin-1-ylCONH |
| 77 | 1-Methylcyc-Pr | 3-CH₃-piperazin-1-ylCH₂CONH |
| 78 | 1-Methylcyc-Pr | Trans-2,5-di-CH₃-piperazin-1-ylCH₂CONH |
| 79 | 1-Methylcyc-Pr | Cis-2,6-di-CH₃-piperazin-1-ylCH₂CONH |
| 80 | 1-Methylcyc-Pr | Cis-3,5-di-CH₃-piperazin-1-ylCH₂CONH |
| 81 | 1-Methylcyc-Pr | Trans-2,6-di-CH₃-piperazin-1-ylCH₂CONH |
| 82 | 1-Methylcyc-Pr | Trans-3,5-di-CH₃-piperazin-1-ylCH₂CONH |
| 83 | 1-Methylcyc-Pr | (R)-1-Ethylpyrrolidin-2-ylCH₂NHCH₂CONH |
| 84 | 1-Methylcyc-Pr | (S)-1-Ethylpyrrolidin-2-ylCH₂NHCH₂CONH |
| 85 | 1-Methylcyc-Pr | 5-CH₃-pyrazin-2-ylCH₂NHCH₂CONH |

TABLE XXIII (a) Structure with H on phenyl, R7, pyrazolopyrimidinone core with R2, N-linked 2,4-dichlorophenyl.

TABLE XXIII-continued (b) Structure: R_7-substituted 2-hydroxyphenyl linked via CH_2 to a pyrazolo[3,4-d]pyrimidin-4(5H)-one bearing R_2 at position 3 and a 2,4,6-trichlorophenyl at N-1.

(c) Structure: R_7-substituted 2-methoxyphenyl linked via CH_2 to a pyrazolo[3,4-d]pyrimidin-4(5H)-one bearing R_2 at position 3 and a 2,4,6-trichlorophenyl at N-1.

| Ex. # | R² | R⁷ |
|---|---|---|
| 1 | i-Bu | 1-CH₃-piperazin-4-ylCH₂CONH |
| 2 | i-Bu | CH₃NHCONH |
| 3 | i-Bu | Morpholin-4-ylCH₂CONH |
| 4 | i-Bu | Azetidin-1-ylCH₂CONH |
| 5 | i-Bu | (CH₃)₂NCH₂CH₂SO₂NH |
| 6 | i-Bu | EtO₂CCH₂NHCONH |
| 7 | i-Bu | Hydantoin-1-yl |
| 8 | i-Bu | HOCH₂CH₂NHCONH |
| 9 | i-Bu | HO₂C(CH₂)₂CONH |
| 10 | i-Bu | Imidazol-1-ylCH₂CONH |
| 11 | i-Bu | Morpholin-4-ylCH₂CH₂NHCSNH |
| 12 | i-Bu | HO₂CCH₂NHCONH |
| 13 | i-Bu | HO₂C(CH₂)₃CONH |
| 14 | i-Bu | H₂NCH₂CONH |
| 15 | i-Bu | CH₃NHCH₂CONH |
| 16 | i-Bu | 4-F-phenylCH₂NHCH₂CONH |
| 17 | i-Bu | Pyrrolidin-1-ylCH₂CONH |
| 18 | i-Bu | Pyrid-2-ylCH₂NHCH₂CONH |
| 19 | i-Bu | Pyrid-3-ylCH₂NHCH₂CONH |
| 20 | i-Bu | Pyrid-4-ylCH₂NHCH₂CONH |
| 21 | i-Bu | BocNHCH₂CH₂NHCH₂CONH |
| 22 | i-Bu | HOCH₂CH(CH₃)NHCH₂CONH |
| 23 | i-Bu | CH₃CH(OH)CH₂NHCH₂CONH |
| 24 | i-Bu | H₂NCH₂CH₂NHCH₂CONH |
| 25 | i-Bu | Morpholin-4-ylCH₂CH₂NHCH₂CONH |
| 26 | i-Bu | 1-CH₃-piperidin-4-ylN(CH₃)CH₂CONH |
| 27 | i-Bu | (CH₃)₂NCH₂CH₂N(CH₃)CH₂CONH |
| 28 | i-Bu | (CH₃)₂NCH(CH₃)CONH |
| 29 | i-Bu | 1-CH₃-L-prolylNH |
| 30 | i-Bu | Homopiperazin-1-ylCH₂CONH |
| 31 | i-Bu | CH₃CH₂NHCH₂CONH |
| 32 | i-Bu | 4-(CH₂NH₂)piperidin-1-ylCH₂CONH |
| 33 | i-Bu | (CH₃)₂NCH₂CH₂NHCH₂CONH |
| 34 | i-Bu | cyclo-C₃H₅NHCH₂CONH |
| 35 | i-Bu | Piperidin-4-ylCH₂NHCH₂CONH |
| 36 | i-Bu | HO(CH₂)₃NHCH₂CONH |
| 37 | i-Bu | 1-Bocpiperidin-4-ylCH₂NHCH₂CONH |
| 38 | i-Bu | HOCH₂CH₂NHCH₂CONH |
| 39 | i-Bu | cyclo-C₄H₇NHCH₂CONH |
| 40 | i-Bu | azetidin-3-ylCONH |
| 41 | i-Bu | D-prolylNH.HCl |
| 42 | i-Bu | Boc-D-prolylNH |
| 43 | i-Bu | L-prolylNH.HCl |
| 44 | i-Bu | Boc-L-prolylNH |
| 45 | i-Bu | Piperidin-1-ylCH₂CH₂NHCH₂CONH |
| 46 | i-Bu | (CH₃)₂CHNHCH₂CONH |
| 47 | i-Bu | BocNHCH₂CH₂CONH |
| 48 | i-Bu | Piperazin-2-yl-CONH |
| 49 | i-Bu | 4-Me-piperazin-2-yl-CONH |
| 50 | i-Bu | Piperidin-1-ylNHCONH |
| 51 | i-Bu | H₂NCH₂CH₂NHCONH.F₃CCO₂H |
| 52 | i-Bu | pyrid-2-ylNHCONH |
| 53 | i-Bu | (CH₃)₂NCH₂CH₂NHCONH |
| 54 | i-Bu | BocNHCH₂CH₂NHCONH |
| 55 | i-Bu | HO(CH₂)₄NHCONH |
| 56 | i-Bu | (CH₃)₂NNHCONH |
| 57 | i-Bu | (CH₃)₂N(CH₂)₃NHCONH |
| 58 | i-Bu | 1-CH₃-homopiperazin-4-yl-CONH |
| 59 | i-Bu | CH₃SO₂NHCONH |
| 60 | i-Bu | CH₃ONHCONH |
| 61 | i-Bu | (CH₃)₂NCH₂CH₂NHCONH |
| 62 | i-Bu | 1-CH₃-piperidin-4-ylN(CH₃)CONH |
| 63 | i-Bu | Tetrahydrofur-2-ylCH₂NHCONH |
| 64 | i-Bu | CH₃(CH₂)₂CH(OH)CH₂NHCONH |
| 65 | i-Bu | HOCH₂CH(CH₃)NHCONH |
| 66 | i-Bu | CH₃CH(OH)CH₂NHCONH |
| 67 | i-Bu | HOCH₂CH₂NHCONH |
| 68 | i-Bu | Morpholin-4-ylNHCONH |
| 69 | i-Bu | (CH₃)₂NCH(CH₃)CH₂NHCONH |
| 70 | i-Bu | 1-CH₃-piperazin-4-ylNHCONH |
| 71 | i-Bu | Morpholin-4-ylCH₂CH₂NHCONH |
| 72 | i-Bu | 1-CH₃-piperazin-4-ylCONH |
| 73 | i-Bu | pyrid-2-ylNHCONH |
| 74 | i-Bu | pyrid-4-ylNHCONH |
| 75 | i-Bu | Pyrrolidin-1-ylCH₂CH₂NHCH₂CONH |
| 76 | i-Bu | 2-CH₃-piperazin-1-ylCONH |
| 77 | i-Bu | 3-CH₃-piperazin-1-ylCH₂CONH |
| 78 | i-Bu | trans-2,5-di-CH₃-piperazin-1-ylCH₂CONH |
| 79 | i-Bu | cis-2,6-di-CH₃-piperazin-1-ylCH₂CONH |
| 80 | i-Bu | cis-3,5-di-CH₃-piperazin-1-ylCH₂CONH |
| 81 | i-Bu | trans-2,6-di-CH₃-piperazin-1-ylCH₂CONH |
| 82 | i-Bu | trans-3,5-di-CH₃-piperazin-1-ylCH₂CONH |
| 83 | i-Bu | (R)-1-Ethylpyrrolidin-2-ylCH₂NHCONH |
| 84 | i-Bu | (S)-1-Ethylpyrrolidin-2-ylCH₂NHCONH |
| 85 | i-Bu | 5-CH₃-pyrazin-2-ylCH₂NHCH₂CONH |

TABLE XXIV (a) Structure: R_7-substituted phenyl linked via CH_2 to a pyrazolo[3,4-d]pyrimidin-4(5H)-one bearing R_2 at position 3 and a 2-chloro-6-R_5-phenyl at N-1.

(b) Structure: R_7-substituted 2-hydroxyphenyl linked via CH_2 to a pyrazolo[3,4-d]pyrimidin-4(5H)-one bearing R_2 at position 3 and a 2-chloro-6-R_5-phenyl at N-1.

TABLE XXIV-continued (c) Structure: R7-substituted 4-methoxyphenyl-CH2- pyrazolopyrimidinone with R2 at 3-position, N-linked to 2-chloro-R5-phenyl, with 4-oxo group.

| Ex. # | R5 | R2 | R7 |
|---|---|---|---|
| 1 | Me | Et | 1-CH$_3$-piperazin-4-ylCH$_2$CONH |
| 2 | Me | Et | CH$_3$NHCONH |
| 3 | Me | Et | Morpholin-4-ylCH$_2$CONH |
| 4 | Me | Et | Azetidin-1-ylCH$_2$CONH |
| 5 | Me | Et | (CH$_3$)$_2$NCH$_2$CH$_2$SO$_2$NH |
| 6 | Me | Et | EtO$_2$CCH$_2$NHCONH |
| 7 | Me | Et | Hydantoin-1-yl |
| 8 | Me | Et | HOCH$_2$CH$_2$NHCONH |
| 9 | Me | Et | HO$_2$C(CH$_2$)$_2$CONH |
| 10 | Me | Et | Imidazol-1-ylCH$_2$CONH |
| 11 | Me | Et | Morpholin-4-ylCH$_2$CH$_2$NHCSNH |
| 12 | Me | Et | HO$_2$CCH$_2$NHCONH |
| 13 | Me | Et | HO$_2$C(CH$_2$)$_3$CONH |
| 14 | Me | Et | H$_2$NCH$_2$CONH |
| 15 | Me | Et | CH$_3$NHCH$_2$CONH |
| 16 | Me | Et | 4-F-phenylCH$_2$NHCH$_2$CONH |
| 17 | Me | Et | Pyrrolidin-1-ylCH$_2$CONH |
| 18 | Me | Et | Pyrid-2-ylCH$_2$NHCH$_2$CONH |
| 19 | Me | Et | Pyrid-3-ylCH$_2$NHCH$_2$CONH |
| 20 | Me | Et | Pyrid-4-ylCH$_2$NHCH$_2$CONH |
| 21 | Me | Et | BocNHCH$_2$CH$_2$NHCH$_2$CONH |
| 22 | Me | Et | HOCH$_2$CH(CH$_3$)NHCH$_2$CONH |
| 23 | Me | Et | CH$_3$CH(OH)CH$_2$NHCH$_2$CONH |
| 24 | Me | Et | H$_2$NCH$_2$CH$_2$NHCH$_2$CONH |
| 25 | Me | Et | Morpholin-4-ylCH$_2$CH$_2$NHCH$_2$CONH |
| 26 | Me | Et | 1-CH$_3$-piperidin-4-ylN(CH$_3$)CH$_2$CONH |
| 27 | Me | Et | (CH$_3$)$_2$NCH$_2$CH$_2$N(CH$_3$)CH$_2$CONH |
| 28 | Me | Et | (CH$_3$)$_2$NCH(CH$_3$)CONH |
| 29 | Me | Et | 1-CH$_3$-L-prolylNH |
| 30 | Me | Et | Homopiperazin-1-ylCH$_2$CONH |
| 31 | Me | Et | CH$_3$CH$_2$NHCH$_2$CONH |
| 32 | Me | Et | 4-(CH$_2$NH$_2$)piperidin-1-ylCH$_2$CONH |
| 33 | Me | Et | (CH$_3$)$_2$NCH$_2$CH$_2$NHCH$_2$CONH |
| 34 | Me | Et | Cyclo-C$_3$H$_5$NHCH$_2$CONH |
| 35 | Me | Et | Piperidin-4-ylCH$_2$NHCH$_2$CONH |
| 36 | Me | ET | HO(CH$_2$)$_3$NHCH$_2$CONH |
| 37 | Me | Et | 1-Bocpiperidin-4-ylCH$_2$NHCH$_2$CONH |
| 38 | Me | ET | HOCH$_2$CH$_2$NHCH$_2$CONH |
| 39 | Me | Et | Cyclo-C$_4$H$_7$NHCH$_2$CONH |
| 40 | Me | Et | Azetidin-3-ylCONH |
| 41 | Me | Et | D-prolylNH.HCl |
| 42 | Me | Et | Boc-D-prolylNH |
| 43 | Me | Et | L-prolylNH.HCl |
| 44 | Me | Et | Boc-L-prolylNH |
| 45 | Me | Et | Piperidin-1-ylCH$_2$CH$_2$NHCH$_2$CONH |
| 46 | Me | Et | (CH$_3$)$_2$CHNHCH$_2$CONH |
| 47 | Me | Et | BocNHCH$_2$CONH |
| 48 | Me | Et | Piperazin-2-yl-CONH |
| 49 | Me | Et | 4-Me-piperazin-2-yl-CONH |
| 50 | Me | Et | Piperidin-1-ylNHCONH |
| 51 | Me | Et | H$_2$NCH$_2$CH$_2$NHCONH.F$_3$CCO$_2$H |
| 52 | Me | Et | Pyrid-2-ylNHCONH |
| 53 | Me | Et | (CH$_3$)$_2$NCH$_2$CH$_2$NHCONH |
| 54 | Me | Et | BocNHCH$_2$CH$_2$NHCONH |
| 55 | Me | Et | HO(CH$_2$)$_4$NHCONH |
| 56 | Me | Et | (CH$_3$)$_2$NNHCONH |
| 57 | Me | Et | (CH$_3$)$_2$N(CH$_2$)$_3$NHCONH |
| 58 | Me | Et | 1-CH$_3$-homopiperazin-4-yl-CONH |
| 59 | Me | Et | CH$_3$SO$_2$NHCONH |
| 60 | Me | Et | CH$_3$ONHCONH |
| 61 | Me | Et | (CH$_3$)$_2$NCH$_2$CH$_2$NHCONH |
| 62 | Me | Et | 1-CH$_3$-piperidin-4-ylN(CH$_3$)CONH |
| 63 | Me | Et | Tetrahydrofur-2-ylCH$_2$NHCONH |
| 64 | Me | Et | CH$_3$(CH$_2$)$_2$CH(OH)CH$_2$NHCONH |
| 65 | Me | Et | HOCH$_2$CH(CH$_3$)NHCONH |
| 66 | Me | Et | CH$_3$CH(OH)CH$_2$NHCONH |
| 67 | Me | Et | HOCH$_2$CH$_2$NHCONH |
| 68 | Me | Et | Morpholin-4-ylNHCONH |
| 69 | Me | Et | (CH$_3$)$_2$NCH(CH$_3$)CH$_2$NHCONH |
| 70 | Me | Et | 1-CH$_3$-piperazin-4-ylNHCONH |
| 71 | Me | Et | Morpholin-4-ylCH$_2$CH$_2$NHCONH |
| 72 | Me | Et | 1-CH$_3$-piperazin-4-ylCONH |
| 73 | Me | Et | Pyrid-2-ylNHCONH |
| 74 | Me | Et | Pyrid-4-ylNHCONH |
| 75 | Me | Et | Pyrrolidin-1-ylCH$_2$CH$_2$NHCH$_2$CONH |
| 76 | Me | Et | 2-CH$_3$-piperazin-1-ylCONH |
| 77 | Me | Et | 3-CH$_3$-piperazin-1-ylCH$_2$CONH |
| 78 | Me | Et | Trans-2,5-di-CH$_3$-piperazin-1-ylCH$_2$CONH |
| 79 | Me | Et | cis-2,6-di-CH$_3$-piperazin-1-ylCH$_2$CONH |
| 80 | Me | Et | cis-3,5-di-CH$_3$-piperazin-1-ylCH$_2$CONH |
| 81 | Me | Et | Trans-2,6-di-CH$_3$-piperazin-1-ylCH$_2$CONH |
| 82 | Me | Et | Trans-3,5-di-CH$_3$-piperazin-1-ylCH$_2$CONH |
| 83 | Me | Et | (R)-1-Ethylpyrrolidin-2-ylCH$_2$NHCONH |
| 84 | Me | Et | (S)-1-Ethylpyrrolidin-2-ylCH$_2$NHCONH |
| 85 | Me | Et | 5-CH$_3$-pyrazin-2-ylCH$_2$NHCH$_2$CONH |

TABLE XXV (a) Structure with H at 2-position of R7-phenyl; pyrazolopyrimidinone with R2 and 2-chloro-R5-phenyl.

(b) Structure with OH at 2-position of R7-phenyl.

(c) Structure with OMe at 2-position of R7-phenyl.

| Ex. # | R5 | R2 | R7 |
|---|---|---|---|
| 1 | Me | cyc-Pr | 1-CH$_3$-piperazin-4-ylCH$_2$CONH |
| 2 | Me | cyc-Pr | CH$_3$NHCONH |
| 3 | Me | cyc-Pr | Morpholin-4-ylCH$_2$CONH |
| 4 | Me | cyc-Pr | Azetidin-1-ylCH$_2$CONH |
| 5 | Me | cyc-Pr | (CH$_3$)$_2$NCH$_2$CH$_2$SO$_2$NH |
| 6 | Me | cyc-Pr | EtO$_2$CCH$_2$NHCONH |
| 7 | Me | cyc-Pr | Hydantoin-1-yl |
| 8 | Me | cyc-Pr | HOCH$_2$CH$_2$NHCONH |
| 9 | Me | cyc-Pr | HO$_2$C(CH$_2$)$_2$CONH |

TABLE XXV-continued

| | | | |
|---|---|---|---|
| 10 | Me | cyc-Pr | Imidazol-1-ylCH$_2$CONH |
| 11 | Me | cyc-Pr | Morpholin-4-ylCH$_2$CH$_2$NHCSNH |
| 12 | Me | cyc-Pr | HO$_2$CCH$_2$NHCONH |
| 13 | Me | cyc-Pr | HO$_2$C(CH$_2$)$_3$CONH |
| 14 | Me | cyc-Pr | H$_2$NCH$_2$CONH |
| 15 | Me | cyc-Pr | CH$_3$NHCH$_2$CONH |
| 16 | Me | cyc-Pr | 4-F-phenylCH$_2$NHCH$_2$CONH |
| 17 | Me | cyc-Pr | Pyrrolidin-1-ylCH$_2$CONH |
| 18 | Me | cyc-Pr | pyrid-2-ylCH$_2$NHCH$_2$CONH |
| 19 | Me | cyc-Pr | pyrid-3-ylCH$_2$NHCH$_2$CONH |
| 20 | Me | cyc-Pr | pyrid-4-ylCH$_2$NHCH$_2$CONH |
| 21 | Me | cyc-Pr | BocNHCH$_2$CH$_2$NHCH$_2$CONH |
| 22 | Me | cyc-Pr | HOCH$_2$CH(CH$_3$)NHCH$_2$CONH |
| 23 | Me | cyc-Pr | CH$_3$CH(OH)CH$_2$NHCH$_2$CONH |
| 24 | Me | cyc-Pr | H$_2$NCH$_2$CH$_2$NHCH$_2$CONH |
| 25 | Me | cyc-Pr | Morpholin-4-ylCH$_2$CH$_2$NHCH$_2$CONH |
| 26 | Me | cyc-Pr | 1-CH$_3$-piperidin-4-ylN(CH$_3$)CH$_2$CONH |
| 27 | Me | cyc-Pr | (CH$_3$)$_2$NCH$_2$CH$_2$N(CH$_3$)CH$_2$CONH |
| 28 | Me | cyc-Pr | (CH$_3$)$_2$NCH(CH$_3$)CONH |
| 29 | Me | cyc-Pr | 1-CH$_3$-L-prolylNH |
| 30 | Me | cyc-Pr | Homopiperazin-1-ylCH$_2$CONH |
| 31 | Me | cyc-Pr | CH$_3$CH$_2$NHCH$_2$CONH |
| 32 | Me | cyc-Pr | 4-(CH$_2$NH$_2$)piperidin-1-ylCH$_2$CONH |
| 33 | Me | cyc-Pr | (CH$_3$)$_2$NCH$_2$CH$_2$NHCH$_2$CONH |
| 34 | Me | cyc-Pr | cyclo-C$_3$H$_5$NHCH$_2$CONH |
| 35 | Me | cyc-Pr | Piperidin-4-ylCH$_2$NHCH$_2$CONH |
| 36 | Me | cyc-Pr | HO(CH$_2$)$_3$NHCH$_2$CONH |
| 37 | Me | cyc-Pr | 1-Bocpiperidin-4-ylCH$_2$NHCH$_2$CONH |
| 38 | Me | cyc-Pr | HOCH$_2$CH$_2$NHCH$_2$CONH |
| 39 | Me | cyc-Pr | cyclo-C$_4$H$_7$NHCH$_2$CONH |
| 40 | Me | cyc-Pr | Azetidin-3-ylCONH |
| 41 | Me | cyc-Pr | D-prolylNH.HCl |
| 42 | Me | cyc-Pr | Boc-D-prolylNH |
| 43 | Me | cyc-Pr | L-prolylNH.HCl |
| 44 | Me | cyc-Pr | Boc-L-prolylNH |
| 45 | Me | cyc-Pr | Piperidin-1-ylCH$_2$CH$_2$NHCH$_2$CONH |
| 46 | Me | cyc-Pr | (CH$_3$)$_2$CHNHCH$_2$CONH |
| 47 | Me | cyc-Pr | BocNHCH$_2$CH$_2$CONH |
| 48 | Me | cyc-Pr | Piperazin-2-yl-CONH |
| 49 | Me | cyc-Pr | 4-Me-piperazin-2-yl-CONH |
| 50 | Me | cyc-Pr | Piperidin-1-ylNHCONH |
| 51 | Me | cyc-Pr | H$_2$NCH$_2$CH$_2$NHCONH.F$_3$CCO$_2$H |
| 52 | Me | cyc-Pr | pyrid-2-ylNHCONH |
| 53 | Me | cyc-Pr | (CH$_3$)$_2$NCH$_2$CH$_2$NHCONH |
| 54 | Me | cyc-Pr | BocNHCH$_2$CH$_2$NHCONH |
| 55 | Me | cyc-Pr | HO(CH$_2$)$_4$NHCONH |
| 56 | Me | cyc-Pr | (CH$_3$)$_2$NNHCONH |
| 57 | Me | cyc-Pr | (CH$_3$)$_2$N(CH$_2$)$_3$NHCONH |
| 58 | Me | cyc-Pr | 1-CH$_3$-homopiperazin-4-yl-CONH |
| 59 | Me | cyc-Pr | CH$_3$SO$_2$NHCONH |
| 60 | Me | cyc-Pr | CH$_3$ONHCONH |
| 61 | Me | cyc-Pr | (CH$_3$)$_2$NCH$_2$CH$_2$NHCONH |
| 62 | Me | cyc-Pr | 1-CH$_3$-piperidin-4-ylN(CH$_3$)CONH |
| 63 | Me | cyc-Pr | Tetrahydrofur-2-ylCH$_2$NHCONH |
| 64 | Me | cyc-Pr | CH$_3$(CH$_2$)$_2$CH(OH)CH$_2$NHCONH |
| 65 | Me | cyc-Pr | HOCH$_2$CH(CH$_3$)NHCONH |
| 66 | Me | cyc-Pr | CH$_3$CH(OH)CH$_2$NHCONH |
| 67 | Me | cyc-Pr | HOCH$_2$CH$_2$NHCONH |
| 68 | Me | cyc-Pr | Morpholin-4-ylNHCONH |
| 69 | Me | cyc-Pr | (CH$_3$)$_2$NCH(CH$_3$)CH$_2$NHCONH |
| 70 | Me | cyc-Pr | 1-CH$_3$-piperazin-4-ylNHCONH |
| 71 | Me | cyc-Pr | Morpholin-4-ylCH$_2$CH$_2$NHCONH |
| 72 | Me | cyc-Pr | 1-CH$_3$-piperazin-4-ylCONH |
| 73 | Me | cyc-Pr | pyrid-2-ylNHCONH |
| 74 | Me | cyc-Pr | pyrid-4-ylNHCONH |
| 75 | Me | cyc-Pr | Pyrrolidin-1-ylCH$_2$CH$_2$NHCH$_2$CONH |
| 76 | Me | cyc-Pr | 2-CH$_3$-piperazin-1-ylCONH |
| 77 | Me | cyc-Pr | 3-CH$_3$-piperazin-1-ylCONH |
| 78 | Me | cyc-Pr | trans-2,5-di-CH$_3$-piperazin-1-ylCH$_2$CONH |
| 79 | Me | cyc-Pr | cis-2,6-di-CH$_3$-piperazin-1-ylCH$_2$CONH |
| 80 | Me | cyc-Pr | cis-3,5-di-CH$_3$-piperazin-1-ylCH$_2$CONH |
| 81 | Me | cyc-Pr | trans-2,6-di-CH$_3$-piperazin-1-ylCH$_2$CONH |
| 82 | Me | cyc-Pr | trans-3,5-di-CH$_3$-piperazin-1-ylCH$_2$CONH |
| 83 | Me | cyc-Pr | (R)-1-Ethylpyrrolidin-2-ylCH$_2$NHCONH |
| 84 | Me | cyc-Pr | (S)-1-Ethylpyrrolidin-2-ylCH$_2$NHCONH |
| 85 | Me | cyc-Pr | 5-CH$_3$-pyrazin-2-ylCH$_2$NHCH$_2$CONH |

TABLE XXVI (a), (b), (c) structures with R$_7$, R$_5$, R$_2$ substituents on pyrazolopyrimidinone scaffolds (H, OH, OMe respectively at the R$_7$-bearing phenyl position).

| Ex. # | R$^5$ | R$^2$ | R$^7$ |
|---|---|---|---|
| 1 | Me | i-Pr | 1-CH$_3$-piperazin-4-ylCH$_2$CONH |
| 2 | Me | i-Pr | CH$_3$NHCONH |
| 3 | Me | i-Pr | Morpholin-4-ylCH$_2$CONH |
| 4 | Me | i-Pr | Azetidin-1-ylCH$_2$CONH |
| 5 | Me | i-Pr | (CH$_3$)$_2$NCH$_2$CH$_2$SO$_2$NH |
| 6 | Me | i-Pr | EtO$_2$CCH$_2$NHCONH |
| 7 | Me | i-Pr | Hydantoin-1-yl |
| 8 | Me | i-Pr | HOCH$_2$CH$_2$NHCONH |
| 9 | Me | i-Pr | HO$_2$C(CH$_2$)$_2$CONH |
| 10 | Me | i-Pr | Imidazol-1-ylCH$_2$CONH |
| 11 | Me | i-Pr | Morpholin-4-ylCH$_2$CH$_2$NHCSNH |
| 12 | Me | i-Pr | HO$_2$CCH$_2$NHCONH |
| 13 | Me | i-Pr | HO$_2$C(CH$_2$)$_3$CONH |
| 14 | Me | i-Pr | H$_2$NCH$_2$CONH |
| 15 | Me | i-Pr | CH$_3$NHCH$_2$CONH |
| 16 | Me | i-Pr | 4-F-phenylCH$_2$NHCH$_2$CONH |
| 17 | Me | i-Pr | Pyrrolidin-1-ylCH$_2$CONH |
| 18 | Me | i-Pr | Pyrid-2-ylCH$_2$NHCH$_2$CONH |
| 19 | Me | i-Pr | Pyrid-3-ylCH$_2$NHCH$_2$CONH |
| 20 | Me | i-Pr | Pyrid-4-ylCH$_2$NHCH$_2$CONH |
| 21 | Me | i-Pr | BocNHCH$_2$CH$_2$NHCH$_2$CONH |
| 22 | Me | i-Pr | HOCH$_2$CH(CH$_3$)NHCH$_2$CONH |
| 23 | Me | i-Pr | CH$_3$CH(OH)CH$_2$NHCH$_2$CONH |
| 24 | Me | i-Pr | H$_2$NCH$_2$CH$_2$NHCH$_2$CONH |
| 25 | Me | i-Pr | Morpholin-4-ylCH$_2$CH$_2$NHCH$_2$CONH |
| 26 | Me | i-Pr | 1-CH$_3$-piperidin-4-ylN(CH$_3$)CH$_2$CONH |
| 27 | Me | i-Pr | (CH$_3$)$_2$NCH$_2$CH$_2$N(CH$_2$)CH$_2$CONH |
| 28 | Me | i-Pr | (CH$_3$)$_2$NCH(CH$_3$)CONH |
| 29 | Me | i-Pr | 1-CH$_3$-L-prolylNH |
| 30 | Me | i-Pr | Homopiperazin-1-ylCH$_2$CONH |
| 31 | Me | i-Pr | CH$_3$CH$_2$NHCH$_2$CONH |
| 32 | Me | i-Pr | 4-(CH$_2$NH$_2$)piperidin-1-ylCH$_2$CONH |
| 33 | Me | i-Pr | (CH$_3$)$_2$NCH$_2$CH$_2$NHCH$_2$CONH |
| 34 | Me | i-Pr | Cyclo-C$_3$H$_5$NHCH$_2$CONH |
| 35 | Me | i-Pr | Piperidin-4-ylCH$_2$NHCH$_2$CONH |
| 36 | Me | i-Pr | HO(CH$_2$)$_3$NHCH$_2$CONH |
| 37 | Me | i-Pr | 1-Bocpiperidin-4-ylCH$_2$NHCH$_2$CONH |

TABLE XXVI-continued

| | | | |
|---|---|---|---|
| 38 | Me | i-Pr | HOCH$_2$CH$_2$NHCH$_2$CONH |
| 39 | Me | i-Pr | Cyclo-C$_4$H$_7$NHCH$_2$CONH |
| 40 | Me | i-Pr | Azetidin-3-ylCONH |
| 41 | Me | i-Pr | D-prolylNH.HCl |
| 42 | Me | i-Pr | Boc-D-prolylNH |
| 43 | Me | i-Pr | L-prolylNH.HCl |
| 44 | Me | i-Pr | Boc-L-prolylNH |
| 45 | Me | i-Pr | Piperidin-1-ylCH$_2$CH$_2$NHCH$_2$CONH |
| 46 | Me | i-Pr | (CH$_3$)$_2$CHNHCH$_2$CONH |
| 47 | Me | i-Pr | BocNHCH$_2$CH$_2$CONH |
| 48 | Me | i-Pr | Piperazin-2-yl-CONH |
| 49 | Me | i-Pr | 4-Me-piperazin-2-yl-CONH |
| 50 | Me | i-Pr | Piperidin-1-ylNHCONH |
| 51 | Me | i-Pr | H$_2$NCH$_2$CH$_2$NHCONH.F$_3$CCO$_2$H |
| 52 | Me | i-Pr | Pyrid-2-ylNHCONH |
| 53 | Me | i-Pr | (CH$_3$)$_2$NCH$_2$CH$_2$NHCONH |
| 54 | Me | i-Pr | BocNHCH$_2$CH$_2$NHCONH |
| 55 | Me | i-Pr | HO(CH$_2$)$_4$NHCONH |
| 56 | Me | i-Pr | (CH$_3$)$_2$NNHCONH |
| 57 | Me | i-Pr | (CH$_3$)$_2$N(CH$_2$)$_3$NHCONH |
| 58 | Me | i-Pr | 1-CH$_3$-homopiperazin-4-yl-CONH |
| 59 | Me | i-Pr | CH$_3$SO$_2$NHCONH |
| 60 | Me | i-Pr | CH$_3$ONHCONH |
| 61 | Me | i-Pr | (CH$_3$)$_2$NCH$_2$CH$_2$NHCONH |
| 62 | Me | i-Pr | 1-CH$_3$-piperidin-4-ylN(CH$_3$)CONH |
| 63 | Me | i-Pr | Tetrahydrofur-2-ylCH$_2$NHCONH |
| 64 | Me | i-Pr | CH$_3$(CH$_2$)$_2$CH(OH)CH$_2$NHCONH |
| 65 | Me | i-Pr | HOCH$_2$CH(CH$_3$)NHCONH |
| 66 | Me | i-Pr | CH$_3$CH(OH)CH$_2$NHCONH |
| 67 | Me | i-Pr | HOCH$_2$CH$_2$NHCONH |
| 68 | Me | i-Pr | Morpholin-4-ylNHCONH |
| 69 | Me | i-Pr | (CH$_3$)$_2$NCH(CH$_3$)CH$_2$NHCONH |
| 70 | Me | i-Pr | 1-CH$_3$-piperazin-4-ylNHCONH |
| 71 | Me | i-Pr | Morpholin-4-ylCH$_2$CH$_2$NHCONH |
| 72 | Me | i-Pr | 1-CH$_3$-piperazin-4-ylCONH |
| 73 | Me | i-Pr | Pyrid-2-ylNHCONH |
| 74 | Me | i-Pr | Pyrid-4-ylNHCONH |
| 75 | Me | i-Pr | Pyrrolidin-1-ylCH$_2$CH$_2$NHCH$_2$CONH |
| 76 | Me | i-Pr | 2-CH$_3$-piperazin-1-ylCONH |
| 77 | Me | i-Pr | 3-CH$_3$-piperazin-1-ylCH$_2$CONH |
| 78 | Me | i-Pr | Trans-2,5-di-CH$_3$-piperazin-1-ylCH$_2$CONH |
| 79 | Me | i-Pr | Cis-2,6-di-CH$_3$-piperazin-1-ylCH$_2$CaNH |
| 80 | Me | i-Pr | Cis-3,5-di-CH$_3$-piperazin-1-ylCH$_2$CONH |
| 81 | Me | i-Pr | Trans-2,6-di-CH$_3$-piperazin-1-ylCH$_2$CONH |
| 82 | Me | i-Pr | Trans-3,5-di-CH$_3$-piperazin-1-ylCH$_2$CONH |
| 83 | Me | i-Pr | (R)-1-Ethylpyrrolidin-2-ylCH$_2$NHCONH |
| 84 | Me | i-Pr | (S)-1-Ethylpyrrolidin-2-ylCH$_2$NHCONH |
| 85 | Me | i-Pr | 5-CH$_3$-pyrazin-2-ylCH$_2$NHCH$_2$CONH |

UTILITY

The present invention provides a method of treating cancer or other proliferative diseases comprising administering to a host in need of such treatment a therapeutically effective amount of a compound of formula (I) or (II), or a pharmaceutically acceptable salt form thereof.

The present invention also provides a novel method of treating cancer or other proliferative diseases comprising administering to a host in need of such treatment a therapeutically effective amount of:
(a) a compound of formula (I) or (II), or a pharmaceutically acceptable salt form thereof; and,
(b) at least one compound selected from the group consisting of anti-cancer agents and anti-proliferative agents.

Selected species were selective for their activity against cyclin dependent kinases and their cyclin bound complexes and were less active against other known serine/threonine kinases such as Protein Kinase A (PKA) and Protein Kinase C (PKC). In addition, these inhibitors were less active against tyrosine kinases such as c-Abl.

Inhibition of Kinase/Cyclin Complex Enzymatic Activity

Several of the compounds disclosed in this invention were assayed for their inhibitory activity against cyclin dependent kinase4/D1, cyclin dependent kinase1/B kinase, cyclin dependent kinase2/A kinase, and cyclin dependent kinase2/E kinase complexes. Briefly, the in vitro assays employ cell lysates from insect cells expressing either of the kinases and subsequently their corresponding regulatory units. The cyclin dependent kinase2/cyclinE is purified from insect cells expressing His-tagged cyclin dependent kinase 2 and cyclin E. The cyclin dependent kinase/cyclin lysate is combined in a microtitre-type plate along with a kinase compatible buffer, $^{32}$P-labeled ATP at a concentration of 50 mM, a GST-Rb fusion protein and the test compound at varying concentrations. The kinase reaction is allowed to proceeded with the radiolabled ATP, then effectively stopped by the addition of a large excess of EDTA and unlabeled ATP. The GST-Rb labeled protein is sequestered on a GSH-Sepharose bead suspension, washed, resuspended in scintillant, and the $^{32}$P activity detected in a scintillation counter. The compound concentration which inhibits 50% of the kinase activity was calculated for each compound. A compound was considered active if its IC$_{50}$ was found to be less than 1 µM.

Inhibition of HCT 116 Cancer Cell Proliferation

To test the cellular activity of several compounds disclosed in this invention, we examined the effect of these compounds on cultured HCT116 cells and determined their effect on cell-cycle progression by the calorimetric cytotoxcity test using sulforhodamine B (Skehan et al. J. Natl. Cancer Inst. 82:1107–12, 1990). Briefly, HCT116 cells are cultured in the-presence of test compounds at increasing concentrations. At selected time points, groups of cells are fixed with trichloroacetic acid and stained with sulforhodamine B (SRB). Unbound dye was removed by washing and protein-bound dye was extracted for determination of optical density. A compound was considered active if its IC$_{50}$ was found to be less than 10 µM.

All patents, patent applications and other applicable publications mentioned herein, are incorporated by reference as though set forth in full in this specification.

The scope of the following claims is intended to encompas all obvious chnages in the details, materials, and arrangement of steps that will occur to one of ordinary skill in the art.

What is claimed is:
1. A compound of formula (I) or its tautomer, formula (II):

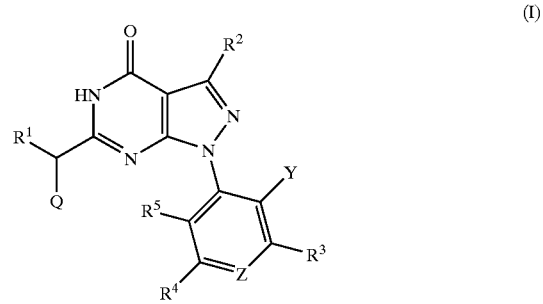

-continued

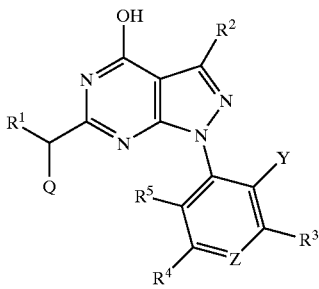

(II)

or a stereoisomer or pharmaceutically acceptable salt form thereof, wherein:

Q is selected from the group consisting of: H, OH, and $C_{1-7}$ alkyl;

Y is selected from the group consisting of: F, Cl, Br, and I;

Z is selected from the group consisting of: N, C—H, C—F, C—Cl, C—Br, C—I, C—$CF_3$, C—$NO_2$, C—$C_{1-4}$ alkyl optionally containing from 1–8 substitution groups, C—$C_{2-4}$ alkenyl optionally containing from 1–8 substitution groups, C—$C_{2-4}$ alkynyl optionally containing from 1–8 substitution groups, C—$C_{1-4}$ alkoxy optionally containing from 1–8 substitution groups, C—$CO_2H$, C—CHO, C—$CONR^6R^9$, C—$CO_2C_{1-3}$ alkyl, C—$C(O)C_{1-2}$ alkyl, C—$CH_2NHR^6$, C—$CONR^6NR^6R^9$, C—$NR^6R^9$; C—$SO_2NR^6R^9$, C—CR=$NNR^6R^9$, C—$CR^6$=$NOR^6$, and C—$R^6$;

$R^1$ is selected from the group consisting of aryl and 5–10 membered aromatic heterocycle containing from 1–4 heteroatoms selected from O, N, and S, and wherein the aryl or the 5–10 membered aromatic heterocycle is optionally substituted with 1–5 $R^7$ groups;

$R^2$ is selected from the group consisting of: $C_{1-4}$ alkyl, $C_{2-4}$ alkenyl, $C_{2-4}$ alkynyl, S—$C_{1-3}$ alkyl, O—$C_{1-3}$ alkyl, $NH_2$, NH—$C_{1-3}$ alkyl, $N(C_{1-2}$ alkyl$)_2$, $OCF_3$, cyclopropyl optionally containing from 1–4 substitution groups, cyclobutyl, cyclopropylmethyl, cyclobutylmethyl, 1-methylcyclopropyl, 1-methylcyclobutyl, $CH_2CN$, $CH_2OH$, $CH_2OCH_3$, $CH_2$, $NH_2$, $CH_2NHC_{1-3}$ alkyl, $CH_2NMe_2$, $CF_3$, CHO, $OCH_2CH_2OH$, OCH(Me)$CH_2OH$, $OCH_2CH(Me)OH$, $OCH_2CH_2NMe_2$, and $CHF_2$;

$R^3$ is selected from the group consisting of: H, F, Cl, Br, I, $CF_3$, CHO, $CHR^6OH$, $COCF_3$, CH=NOH, CH=$NOCH_3$, CH=$NNH_2$, CH=NNHMe, CH=$NNMe_2$, CH=$CHR^6$, $C_{1-3}$ alkyl, $C_{1-3}$ alkoxy, $CO_2H$, $CONH_2$, $CONH(C_{1-3}$ alkyl), $CONR^6R^9$, $CO_2C_{1-3}$ alkyl, $C(O)C_{1-2}$ alkyl, $NH_2$, $NHR^6$, and $NR^6R^9$;

$R^4$ is selected from the group consisting of: H, F, Cl, Br, I, $CF_3$, $C_{1-3}$ alkyl, $C_{2-3}$ alkenyl, $NH_2$, $NHR^6$, and $NR^6R^9$;

$R^5$ is selected from the group consisting of: H, $C_{1-3}$ alkyl, F, Cl, Br, I, $CF_3$, and $C_{2-3}$ alkenyl;

$R^6$ and $R^9$ are independently, at each occurrence, the same or different, and are selected from the group consisting of: H, $C_{1-8}$ alkyl optionally containing from 1–8 substitution groups, and $C_{3-7}$ cyclo-alkyl;

alternatively, $R^6$ and $R^9$, together with the atoms to which they are attached, form a heterocycle having 5–7 atoms in the ring and containing 0–1 additional N, O, or S atom; or, $R^6$ and $R^9$, together with the atoms to which they are attached, form a bicyclic heterocycle having 9–11 atoms in the ring and containing one additional N, S, or O atom; or, $R^6$ and $R^9$, together with the atoms to which they are attached, form a 5–7 membered ring and containing 0–3 additional N, S, or O atoms;

$R^7$ is independently, at each occurrence, selected from the group consisting of: OH, $C_{1-6}$ alkoxy, $OC_{2-6}$ alkyl-$CO_2H$, O—$C_{2-6}$-alkyl-$NR^6R^9$, F, Cl, Br, I, $CF_3$, $OCF_3$, —CN, —$NO_2$, $CO_2H$, $CO_2(C_{1-6}$ alkyl), $CONR^6R^9$, $NR^6CONHOR^6$, $NR^6CONHSO_2R^6$, $NHNR^6C(O)OR^6$, $NR^6C(O)NR^6R^9$, $NH_2$, NH($C_{1-3}$ alkyl), N($C_{1-3}$ alkyl)$_2$, —$SO_2NR^6R^9$, $NHSO_2NHCO_2C_{1-4}$ alkyl, $NR^6SO_2NR^6R^9$, $NR^6SO_2CHR^6CH_2NR^6R^9$, $NR^6COCHR^6NR^6R^9$, $NR^6COCHR^6NR^6CHR^6R^9$, $NR^6COCH_2CHR^6NR^6R^9$, $NR^6COCHR^6CH_2NR^6R^9$, $NR^6CO(CH_2)_mNR^6R^9$, $NR^6CONR^6(CH_2)_nNR^6R^9$, $NR^6CO_2(CHR^6)_nNR^6R^9$, $CONR^6NR^6R^9$, $NR^6CONR^6NR^6R^9$, $C_{3-10}$ carbocycle, $NHCONR^6$, $NHCONHCH_2R^6$, $NHCOR^6$, $NHCOCH_2R^6$, $C_{1-10}$ alkyl optionally substituted with 1–5 substitution groups, $C_{2-10}$ alkenyl optionally substituted with 1–5 substitution groups, $C_{2-10}$ alkynyl optionally substituted with 1–5 substitution groups, and $C_{3-10}$ heterocycle containing 1–4 heteroatoms selected from O, N, and S;

$R^8$ is independently, at each occurrence, selected from the group consisting of: =O, OH, $C_{3-6}$ cycloalkyl, $C_{1-16}$ alkoxy, $NH_2$, NH($C_{1-6}$ alkyl), N($C_{1-6}$ alkyl)$_2$, F, Cl, Br, I, $CO_2H$, $COR^6$, $CO_2$(benzyl), $CO_2(C_{1-6}$ alkyl), and $CONR^6R^9$;

n at each occurrence is independently selected from 2, 3, 4, 5, and 6; and, m at each occurrence is independently selected from 3, 4, 5, and 6.

2. A compound according to claim 1, wherein:

Q is selected from the group.: H, OH, and $CH_3$;

Y is selected from the group: F, Cl, and Br;

Z is selected from the group consisting of: N, CH, CF, CCl, CBr, CI, C—$CF_3$, C—$NO_2$, C—$C_{1-4}$ alkyl optionally substituted with 1–5 substitution groups, C—$C_{2-4}$ alkenyl optionally substituted with 1–5 substitution groups, C—$C_{2-4}$ alkynyl optionally substituted with 1–5 substitution groups, C—$C_{1-4}$ alkoxy, C—$CO_2H$, C—CHO, C—$CONR^6R^9$, C—$CO_2C_{1-3}$ alkyl, C—C(O)$C_{1-2}$ alkyl, C—$CH_2NHR^6$, C—$CONR^6NR^6R^9$, C—$NR^6R^9$; C—$SO_2NR^6R^9$, C—CR=$NNR^6R^9$, C—$CR^6$=$NOR^6$, and C—$R^6$;

$R^1$ is selected from the group: phenyl and a 5–10 membered aromatic heterocycle containing from 1–4 heteroatoms selected from O, N, and S, and $R^1$ is substituted with 0–3 $R^7$;

$R^2$ is selected from the group: $C_{2-4}$ alkyl, $C_{2-4}$ alkenyl, $C_{2-4}$ alkynyl, S—$C_{1-2}$ alkyl, O—$C_{1-2}$ alkyl, cyclopropyl, cyclobutyl, 1-methylcyclopropyl, $CH_2CN$, $CH_2OH$, $CH_2OCH_3$, $CH_2NH_2$, $CH_2NMe_2$, $CF_3$, and CHO;

$R^3$ is independently selected from the group: H, F, Cl, $CH_3$, $CH_2CH_3$, CHO, $CHR^gOH$, $COCF_3$, CH=NOH, CH=$NOCH_3$, CH=$NNH_2$, CH=NNHMe, CH=$NNMe_2$, and CH=$CHR^a$;

$R^4$ is independently selected from the group: H, F, Cl, and $CH_3$;

$R^5$ is independently selected from the group: H, $CH_3$, F, Cl, Br, and $CF_3$;

R⁶ and R⁹ are the same or different, and are selected from the group consisting of H, $C_{1-8}$ optionally substituted with 1–5 substitution groups, and cyclo-alkyl $C_{3-7}$;

alternatively, R⁶ and R⁹, together with the atoms to which they are attached, form a heterocycle having 5–7 atoms in the ring and containing 0–1 additional N, O, or S atom or, form a bicyclic heterocycle having 9–11 atoms in the ring and containing one additional N, S, or O atom or, form a 5–7 membered ring and containing 0–3 additional N, S, or O atoms;

R⁷ is independently, at each occurrence, selected from the group consisting of: OH, $C_{1-6}$ alkoxy, $OC_{2-6}$ alkyl-$CO_2H$, O—$C_{2-6}$-alkyl-NR⁶R⁹, F, Cl, Br, I, $CF_3$, $OCF_3$, —CN, —$NO_2$, $CO_2H$, $CO_2(C_{1-6}$ alkyl), CONR⁶R⁹, NR⁶CONHOR⁶, NR⁶CONHSO₂R⁶, NHNR⁶C(O)OR⁶, NR⁶C(O)NR⁶R⁹, $NH_2$, NH($C_{1-3}$ alkyl), N($C_{1-3}$ alkyl)₂, —SO₂NR⁶R⁹, NHSO₂NHCO₂$C_{1-4}$ alkyl, NR⁶SO₂NR⁶R⁹, NR⁶SO₂CHR⁶CH₂NR⁶R⁹, NR⁶COCHR⁶NR⁶R⁹, NR⁶COCHR⁶NR⁶CHR⁶R⁹, NR⁶COCH₂CHR⁶NR⁶R⁹, NR⁶COCHR⁶CH₂NR⁶R⁹, NR⁶CO(CH₂)ₘNR⁶R⁹, NR⁶CONR⁶(CH₂)ₙNR⁶R⁹, NR⁶CO₂(CHR⁶)ₙNR⁶R⁹, CONR⁶NR⁶R⁹, NR⁶CONR⁶NR⁶R⁹, $C_{3-10}$ carbocycle, NHCONR⁶, NHCONHCH₂R⁶, NHCOR⁶, NHCOCH₂R⁶, $C_{1-10}$ alkyl optionally substituted with 0, 1, 2 or 3 R⁸ groups, $C_{2-10}$ alkenyl optionally substituted with 0, 1, 2 or 3 R⁸ groups, $C_{2-10}$ alkynyl optionally substituted with 0, 1, 2, or 3 R⁸ groups, and $C_{3-10}$ heterocycle containing 1–4 heteroatoms selected from O, N, and S;

R⁸ is independently, at each occurrence, selected from the group: =O, OH, $C_{3-6}$ cycloalkyl, $C_{1-6}$ alkoxy, $NH_2$, NH($C_{1-6}$ alkyl), N($C_{1-6}$ alkyl)₂, F, Cl, Br, I, $CO_2H$, COR⁶, $CO_2$(benzyl), $CO_2(C_{1-6}$ alkyl), and CONR⁶R⁹;

n at each occurrence is independently selected from 2, 3, 4, 5, and 6; and, m at each occurrence is independently selected from 3, 4, 5, and 6.

3. A compound according to claim 2, wherein: R² is selected from the group consisting of: ethyl, cyclopropyl, cyclobutyl, 1-methylcyclopropyl, and $CF_3$.

4. A compound accordoing to claim 3 wherein:

R⁵ is $CH_3$.

5. A compound according to claim 1, wherein the ompound is selected from the group consisting of:

a) 1-(2,4,6-trichlorophenyl)-3-ethyl-6-(4-hydroxy-3-methoxybenzyl)pyrazolo[3,4-d]pyrimidin-4-one;

b) 1-(2,4,6-trichlorophenyl)-3-ethyl-6-(4-hydroxybenzyl)pyrazolo[3,4-d]pyrimidin-4-one;

c) 1-(2,4,6-trichlorophenyl)-3-ethyl-6-(3-hydroxy-4-methoxybenzyl)pyrazolo[3,4-d]pyrimidin-4-one;

d) 1-(2,4,6-trichlorophenyl)-3-ethyl-6-(3-aminobenzyl)pyrazolo[3,4-d]pyrimidin-4-one;

e) 1-(2,4,6-trichlorophenyl)-3-ethyl-6-(3-hydroxybenzyl)pyrazolo[3,4-d]pyrimidin-4-one;

f) 1-(2,4,6-trichlorophenyl)-3-ethyl-6-(4-aminobenzyl)pyrazolo[3,4-d]pyrimidin-4-one;

g) 1-(2,4,6-trichlorophenyl)-3-ethyl-6-(4-acetamidobenzyl)pyrazolo[3,4-d]pyrimidin-4-one;

h) 1-(2,4,6-trichlorophenyl)-3-ethyl-6-(4-(N-(t-butoxycarbonyl)glycinamido)benzyl)pyrazolo[3,4-d]pyrimidin-4-one;

i) 1-(2,4,6-trichlorophenyl)-3-ethyl-6-(4-(2-(N,N-dimethylamino)ethylaminocarbonylamino)benzyl)pyrazolo[3,4-d]pyrimidin-4-one;

j) 1-(2,4,6-trichlorophenyl)-3-ethyl-6-(3-amino-2-methylbenzyl)pyrazolo[3,4-d]pyrimidin-4-one;

k) 1-(2,4,6-trichlorophenyl)-3-ethyl-6-(4-(pyrid-2-ylmethylaminocarbonylamino)benzyl)pyrazolo[3,4-d]pyrimidin-4-one;

l) 1-(2,4,6-trichlorophenyl)-3-ethyl-6-(4-glycinamidobenzyl)pyrazolo[3,4-d]pyrimidin-4-one;

m) 1-(2,4,6-trichlorophenyl)-3-ethyl-6-(4-(pyrid-4-ylmethylaminocarbonylamino)benzyl)pyrazolo[3,4-d]pyrimidin-4-one;

n) 1-(2,4,6-trichlorophenyl)-3-ethyl-6-(para-biphen-4-ylmethyl)pyrazolo[3,4-d]pyrimidin-4-one;

o) 1-(2,6-dichlorophenyl)-3-ethyl-6-(4-aminobenzyl)pyrazolo[3,4-d]pyrimidin-4-one;

p) 1-(2,4,6-trichlorophenyl)-3-ethyl-6-(4-(4-methylpiperazin-1-ylcarbonylamino)benzyl)pyrazolo[3,4-d]pyrimidin-4-one;

q) 1-(2,4,6-trichlorophenyl)-3-ethyl-6-(4-(dimethylamino)benzyl)pyrazolo[3,4-d]pyrimidin-4-one;

r) 1-(2,4,6-trichlorophenyl)-3-ethyl-6-(2-(hydroxymethyl)benzyl)pyrazolo[3,4-d]pyrimidin-4-one;

s) 1-(2,6-dichlorophenyl)-3-ethyl-6-(4-hydroxybenzyl)pyrazolo[3,4-d]pyrimidin-4-one;

t) 1-(2,4,6-trichlorophenyl)-3-ethyl-6-(4-(methoxyaminocarbonylmethyl)benzyl)pyrazolo[3,4-d]pyrimidin-4-one;

u) 1-(2,6-dichlorophenyl)-3-ethyl-6-(3-methoxybenzyl)pyrazolo[3,4-d]pyrimidin-4-one;

v) 1-(2,6-dichlorophenyl)-3-ethyl-6-(4-hydroxybenzyl)pyrazolo[3,4-d]pyrimidin-4-one;

w) 1-(2-chloro-6-methylphenyl)-3-ethyl-6-(4-hydroxybenzyl)pyrazolo[3,4-d]pyrimidin-4-one;

x) 1-(2,4,6-trichlorophenyl)-3-ethyl-6-(3,5-dihydroxybenzyl)pyrazolo[3,4-d]pyrimidin-4-one;

y) 1-(2,4,6-trichlorophenyl)-3-ethyl-6-(4-hydroxy-3-methylbenzyl)pyrazolo[3,4-d]pyrimidin-4-one;

z) 1-(2,4,6-trichlorophenyl)-3-ethyl-6-(4-amino-3-nitrobenzyl)pyrazolo[3,4-d]pyrimidin-4-one;

aa) 1-(2,4,6-trichlorophenyl)-3-ethyl-6-(4-(methylaminocarbonylamino)benzyl)pyrazolo[3,4-d]pyrimidin-4-one;

ab) 1-(2,4,6-trichlorophenyl)-3-ethyl-6-(3-(methanesulfonamido)benzyl)pyrazolo[3,4-d]pyrimidin-4-one;

ac) 1-(2,4,6-trichlorophenyl)-3-ethyl-6-(4-(methanesulfonamido)benzyl)pyrazolo[3,4-d]pyrimidin-4-one;

ad) 1-(2,6-dichloro-4-(pyrid-3-ylaminocarbonyl)phenyl)-3-ethyl-6-(3-methoxybenzyl)pyrazolo[3,4-d]pyrimidin-4-one;

ae) 1-(2,6-dichloro-4-(pyrid-4-ylaminocarbonyl)phenyl)-3-ethyl-6-(3-methoxybenzyl)pyrazolo[3,4-d]pyrimidin-4-one;

af) 1-(2,6-dichloro-4-(cyclopropylaminocarbonyl)phenyl)-3-ethyl-6-(3-methoxybenzyl)pyrazolo[3,4-d]pyrimidin-4-one;

ag) 1-(2,6-dichloro-4-(N-(pyrid-3-ylmethyl)aminocarbonyl)phenyl)-3-ethyl-6-(3-methoxybenzyl)pyrazolo[3,4-d]pyrimidin-4-one;

ah) 1-(2,6-dichloro-4-(N-(pyrid-2-ylmethyl)aminocarbonyl)phenyl)-3-ethyl-6-(3-methoxybenzyl)pyrazolo[3,4-d]pyrimidin-4-one;

ai) 1-(2,6-dichloro-4-(ethylaminocarbonyl)phenyl)-3-ethyl-6-(3-methoxybenzyl)pyrazolo[3,4-d]pyrimidin-4-one;
aj) 1-(2,6-dichloro-4-(benzylaminocarbonyl)phenyl)-3-ethyl-6-(3-hydroxybenzyl)pyrazolo[3,4-d]pyrimidin-4-one;
ak) 1-(2,6-dichloro-4-(2-(dimethylamino)ethylaminocarbonyl)phenyl)-3-ethyl-6-(3-methoxybenzyl)pyrazolo[3,4-d]pyrimidin-4-one;
al) 1-(2,6-dichloro-4-(methylaminocarbonyl)phenyl)-3-ethyl-6-(4-methoxybenzyl)pyrazolo[3,4-d]pyrimidin-4-one;
am) 1-(2,4,6-trichlorophenyl)-3-ethyl-6-(3-(N,N-dimethylglycinamido)-2-methylbenzyl)pyrazolo[3,4-d]pyrimidin-4-one;
an) 1-(2,4,6-trichlorophenyl)-3-ethyl-6-(4-(N,N-dimethylglycinamido)benzyl)pyrazolo[3,4-d]pyrimidin-4-one;
ao) 1-(2,4,6-trichlorophenyl)-3-ethyl-6-(4-(N-methylglycinamido)benzyl)pyrazolo[3,4-d]pyrimidin-4-one;
ap) 1-(2,6-dichloro-4-bromophenyl)-3-ethyl-6-(4-hydroxybenzyl)pyrazolo[3,4-d]pyrimidin-4-one;
aq) 1-(2,4,6-trichlorophenyl)-3-isopropyl-6-(4-(methoxycarbonylamino)benzyl)pyrazolo[3,4-d]pyrimidin-4-one;
ar) 1-(2,4,6-trichlorophenyl)-3-isopropyl-6-(3-hydroxybenzyl)pyrazolo[3,4-d]pyrimidin-4-one;
as) 1-(2,4,6-trichlorophenyl)-3-isopropyl-6-(3-hydroxy-4-methoxybenzyl)pyrazolo[3,4-d]pyrimidin-4-one;
at) 1-(2,4,6-trichlorophenyl)-3-isopropyl-6-(3-aminobenzyl)pyrazolo[3,4-d]pyrimidin-4-one;
au) 1-(2,4,6-trichlorophenyl)-3-isopropyl-6-(3-(methanesulfonamido)benzyl)pyrazolo[3,4-d]pyrimidin-4-one;
av) 1-(2,4,6-trichlorophenyl)-3-isopropyl-6-(3-(difluoroacetamido)benzyl)pyrazolo[3,4-d]pyrimidin-4-one;
aw) 1-(2,4,6-trichlorophenyl)-3-isopropyl-6-(3-(acetamido)benzyl)pyrazolo[3,4-d]pyrimidin-4-one;
ax) 1-(2,4,6-trichlorophenyl)-3-isopropyl-6-(3-(methylaminocarbonylamino)benzyl)pyrazolo[3,4-d]pyrimidin-4-one;
ay) 1-(2,4,6-trichlorophenyl)-3-isopropyl-6-(3-methoxybenzyl)pyrazolo[3,4-d]pyrimidin-4-one;
az) 1-(2,4,6-trichlorophenyl)-3-isopropyl-6-(4-(azetidin-3-ylcarbonylamino)benzyl)pyrazolo[3,4-d]pyrimidin-4-one;
ba) 1-(2,4,6-trichlorophenyl)-3-isopropyl-6-(4-(2-aminoethylaminomethylcarbonylamino)benzyl)pyrazolo[3,4-d]pyrimidin-4-one;
bb) 1-(2,4,6-trichlorophenyl)-3-isopropyl-6-(4-(isopropylaminomethylcarbonylamino)benzyl)pyrazolo[3,4-d]pyrimidin-4-one;
bc) 1-(2,4,6-trichlorophenyl)-3-isopropyl-6-(4-(4-fluorobenzylaminomthylcarbonylamino)benzyl)pyrazolo[3,4-d]pyrimidin-4-one;
bd) 1-(2,4,6-trichlorophenyl)-3-isopropyl-6-(4-(pyrrolidin-1-ylmethylcarbonylamino)benzyl)pyrazolo[3,4-d]pyrimidin-4-one;
be) 1-(2,4,6-trichlorophenyl)-3-isopropyl-6-(4-(pyrid-2-ylmethylaminomethylcarbonylamino)benzyl)pyrazolo[3,4-d]pyrimidin-4-one;
bf) 1-(2,4,6-trichlorophenyl)-3-isopropyl-6-(4-(2-(t-butoxycarbonylamino)ethylaminomethylcarbonylamino)benzyl)pyrazolo[3,4-d]pyrimidin-4-one;
bg) 1-(2,4,6-trichlorophenyl)-3-isopropyl-6-(4-(pyrid-3-ylmethylaminomethylcarbonylamino)benzyl)pyrazolo[3,4-d]pyrimidin-4-one;
bh) 1-(2,4,6-trichlorophenyl)-3-isopropyl-6-(4-(pyrid-4-ylmethylaminomethylcarbonylamino)benzyl)pyrazolo[3,4-d]pyrimidin-4-one;
bi) 1-(2,4,6-trichlorophenyl)-3-isopropyl-6-(4-(2-(morpholin-4-yl)ethylaminomethylcarbonylamino)benzyl)pyrazolo[3,4-d]pyrimidin-4-one;
bj) 1-(2,6-dichlorophenyl)-3-isopropyl-6-(4-(methylaminocarbonylmethyl)benzyl)pyrazolo[3,4-d]pyrimidin-4-one;
bk) 1-(2,6-dichlorophenyl)-3-isopropyl-6-(4-(ethylaminocarbonylmethyl)benzyl)pyrazolo[3,4-d]pyrimidin-4-one;
bl) 1-(2,6-dichlorophenyl)-3-isopropyl-6-(4-(piperazin-1-ylcarbonylmethyl)benzyl)pyrazolo[3,4-d]pyrimidin-4-one;
bm) 1-(2,4,6-trichlorophenyl)-3-isopropyl-6-(4-methylpyrid-3-ylmethyl)pyrazolo[3,4-d]pyrimidin-4-one;
bn) 1-(2,6-dichlorophenyl)-3-isopropyl-6-(4-(2-(dimethylamino)ethylaminocarbonylmethyl)benzyl)pyrazolo[3,4-d]pyrimidin-4-one;
bo) 1-(2,4,6-trichlorophenyl)-3-isopropyl-6-(4-(2,2-dimethylhydrazin-1-ylcarbonylamino)benzyl)pyrazolo[3,4-d]pyrimidin-4-one;
bp) 1-(2,4,6-trichlorophenyl)-3-isopropyl-6-(4-(1-hydroxybut-4-ylaminocarbonylamino)benzyl)pyrazolo[3,4-d]pyrimidin-4-one;
bq) (+/−)1-(2,4,6-trichlorophenyl)-3-isopropyl-6-(4-(2-hydroxyprop-1-ylaminomethylcarbonylamino)benzyl)pyrazolo[3,4-d]pyrimidin-4-one;
br) (+/−)1-(2,4,6-trichlorophenyl)-3-isopropyl-6-(4-(1-hydroxyprop-2-ylaminomethylcarbonylamino)benzyl)pyrazolo[3,4-d]pyrimidin-4-one;
bs) 1-(2,4,6-trichlorophenyl)-3-isopropyl-6-(pyrid-3-ylmethyl)pyrazolo[3,4-d]pyrimidin-4-one;
bt) 1-(2,4,6-trichlorophenyl)-3-isopropyl-6-(4-aminobenzyl)pyrazolo[3,4-d]pyrimidin-4-one;
bu) 1-(2,4,6-trichlorophenyl)-3-isopropyl-6-(4-(dimethylamino)benzyl)pyrazolo[3,4-d]pyrimidin-4-one;
bv) 1-(2,4,6-trichlorophenyl)-3-isopropyl-6-(pyrid-4-ylmethyl)pyrazolo[3,4-d]pyrimidin-4-one;
bw) 1-(2,4,6-trichlorophenyl)-3-isopropyl-6-(4-(N,N-dimethylglycinamido)-3-hydroxybenzyl)pyrazolo[3,4-d]pyrimidin-4-one;
bx) 1-(2,4,6-trichlorophenyl)-3-isopropyl-6-(4-(N,N-dimethylglycinamido)-3-methoxybenzyl)pyrazolo[3,4-d]pyrimidin-4-one;
by) 1-(2,4,6-trichlorophenyl)-3-isopropyl-6-(4-(methylaminocarbonylamino)-3-methoxybenzyl)pyrazolo[3,4-d]pyrimidin-4-one;
bz) 1-(2,4,6-trichlorophenyl)-3-isopropyl-6-(4-(N-(3-(dimethylamino)propyl)aminocarbonylamino)benzyl)pyrazolo[3,4-d]pyrimidin-4-one;
ca) 1-(2,4,6-trichlorophenyl)-3-isopropyl-6-(benzoxazol-2-on-6-ylmethyl)pyrazolo[3,4-d]pyrimidin-4-one;
cb) 1-(2,6-dichlorophenyl)-3-isopropyl-6-(4-(4-methylpiperazin-1-ylcarbonylmethyl)benzyl)pyrazolo[3,4-d]pyrimidin-4-one;

cc) 1-(2,6-dichlorophenyl)-3-isopropyl-6-(4-(N-methyl, N-(2-(dimethylamino)ethyl)aminocarbonylmethyl) benzyl)-pyrazolo[3,4-d]pyrimidin-4-one;

cd) 1-(2,4,6-trichlorophenyl)-3-isopropyl-6-(4-(methylaminocarbonylamino)-3-hydroxybenzyl) pyrazolo[3,4-d]pyrimidin-4-one;

ce) 1-(2,4,6-trichlorophenyl)-3-isopropyl-6-(4-(4-methylpiperazin-1-ylmethylcarbonylamino)benzyl) pyrazolo[3,4-d]pyrimidin-4-one;

cf) 1-(2,4,6-trichlorophenyl)-3-isopropyl-6-(4-(piperazin-1-ylmethylcarbonylamino)benzyl)pyrazolo[3,4-d]pyrimidin-4-one;

cg) 1-(2,4,6-trichlorophenyl)-3-isopropyl-6-(4-(morpholin-4-ylmethylcarbonylamino)benzyl) pyrazolo[3,4-d]pyrimidin-4-one;

ch) 1-(2,4,6-trichlorophenyl)-3-isopropyl-6-(4-(imidazol-1-ylmethylcarbonylamino)benzyl)pyrazolo[3,4-d] pyrimidin-4-one;

ci) 1-(2,4,6-trichlorophenyl)-3-isopropyl-6-(4-(N-methyl-N-(1-methylpiperidin-4-yl) aminomethylcarbonylamino)benzyl)pyrazolo[3,4-d] pyrimidin-4-one;

cj) 1-(2,4,6-trichlorophenyl)-3-isopropyl-6-(4-(cyclopropylaminomethylcarbonylamino)benzyl) pyrazolo[3,4-d]pyrimidin-4-one;

ck) 1-(2,4,6-trichlorophenyl)-3-isopropyl-6-(4-(N,N-dimethylglycinamido)benzyl)pyrazolo[3,4-d] pyrimidin-4-one;

cl) 1-(2,4,6-trichlorophenyl)-3-isopropyl-6-(4-(methylaminomethylcarbonylamino)benzyl)pyrazolo [3,4-d]pypyrimidin-4-one;

cm) 1-(2,4,6-trichlorophenyl)-3-isopropyl-6-(3-aminoindazol-5-ylmethyl)pyrazolo[3,4-d]pyrimidin-4-one;

cn) 1-(2,4,6-trichlorophenyl)-3-isopropyl-6-(4-(N-ethyl, N-(2-(dimethylamino)ethyl) aminomethylcarbonylmino)benzyl)-pyrazolo[3,4-d] pyrimidin-4-one;

co) 1-(2,4,6-trichlorophenyl)-3-isopropyl-6-(4-(4-ethylpiperazin-1-ylcarbonylmethyl)benzyl)pyrazolo[3,4-d]pyrimidin-4-one;

cp) 1-(2,4,6-trichlorophenyl)-3-isopropyl-6-(4-(azetidin-1-ylmethylcarbonylamino)benzyl)pyrazolo[3,4-d] pyrimidin-4-one;

cq) 1-(2,4,6-trichlorophenyl)-3-isopropyl-6-(3-hydroxy-4-(imidazol-1-ylmethylcarbonylamino)benzyl) pyrazolo[3,4-d]pyrimidin-4-one;

cr) 1-(2,4,6-trichlorophenyl)-3-isopropyl-6-(4-(4-methylpiperazin-1-ylcarbonylamino)benzyl)pyrazolo [3,4-d]pyrimidin-4-one;

cs) 1-(2,4,6-trichlorophenyl)-3-isopropyl-6-(4-(3-(dimethylamino)prop-1-ylaminocarbonylamino) benzyl)pyrazolo[3,4-d]pyrimidin-4-one;

ct) 1-(2,4,6-trichlorophenyl)-3-isopropyl-6-(4-(4-methylhomopiperazin-1-ylcarbonylamino)benzyl) pyrazolo[3,4-d]pyrimidin-4-one;

cu) 1-(2,4,6-trichlorophenyl)-3-isopropyl-6-(4-(4-methylpiperazin-2-ylcarbonylamino)benzyl)pyrazolo [3,4-d]pyrimidin-4-one;

cv) 1-(2,4,6-trichlorophenyl)-3-isopropyl-6-(4-(t-butoxycarbonylaminosulfonamido)benzyl)pyrazolo[3,4-d]pyrimidin-4-one;

cw) 1-(2-chloro-6-methylphenyl)-3-isopropyl-6-(4-aminobenzyl)pyrazolo[3,4-d]pyrimidin-4-one;

cx) 1-(2,4,6-trichlorophenyl)-3-isopropyl-6-(4-(2-(morpholin-4-yl)ethylaminothiocarbonylamino) benzyl)pyrazolo[3,4-d]pyrimidin-4-one;

cy) 1-(2-chloro-6-methylphenyl)-3-isopropyl-6-(4-(N,N-dimethylglycinamido)benzyl)pyrazolo[3,4-d] pyrimidin-4-one;

cz) 1-(2,4,6-trichlorophenyl)-3-isopropyl-6-(4-bromobenzyl)pyrazolo[3,4-d]pyrimidin-4-one;

da) 1-(2,4,6-trichlorophenyl)-3-isopropyl-6-(4-(piperazin-2-ylcarbonylamino)benzyl)pyrazolo[3,4-d] pyrimidin-4-one;

db) 1-(2,4,6-trichlorophenyl)-3-isopropyl-6-(4-(1,4-dimethylpiperazin-2-ylcarbonylamino)benzyl) pyrazolo[3,4-d]pyrimidin-4-one;

dc) 1-(2,4,6-trichlorophenyl)-3-isopropyl-6-(4-(2-(dimethylamino)ethylsulfonamido)benzyl)pyrazolo[3,4-d]pyrimidin-4-one;

dd) 1-(2,4,6-trichlorophenyl)-3-isopropyl-6-(4-amino-3-methoxybenzyl)pyrazolo[3,4-d]pyrimidin-4-one;

de) 1-(2,4,6-trichlorophenyl)-3-isopropyl-6-(4-hydantoin-3-ylbenzyl)pyrazolo[3,4-d]pyrimidin-4-one;

df) 1-(2,4,6-trichlorophenyl)-3-isopropyl-6-(2H-1,4-benzoxazin-3-on-7-ylmethyl)pyrazolo[3,4-d] pyrimidin-4-one;

dg) 1-(2,4,6-trichlorophenyl)-3-isopropyl-6-(4-(N-(2-(dimethylamino)ethyl)aminocarbonylamino)benzyl) pyrazolo[3,4-d]pyrimidin-4-one;

dh) 1-(2,4,6-trichlorophenyl)-3-isopropyl-6-(4-(2-hydroxyethylaminocarbonylamino)benzyl)pyrazolo[3,4-d]pyrimidin-4-one;

di) 1-(2,4,6-trichlorophenyl)-3-isopropyl-6-(4-methylbenzyl)pyrazolo[3,4-d]pyrimidin-4-one;

dj) 1-(2,4,6-trichlorophenyl)-3-isopropyl-6-(2-methylbenzyl)pyrazolo[3,4-d]pyrimidin-4-one;

dk) 1-(2,4,6-trichlorophenyl)-3-isopropyl-6-(4-glycinamidobenzyl)pyrazolo[3,4-d]pyrimidin-4-one;

dl) 1-(2,4,6-trichlorophenyl)-3-isopropyl-6-(4-(N-methylglycinamido)benzyl)pyrazolo[3,4-d]pyrimidin-4-one;

dm) 1-(2,4,6-trichlorophenyl)-3-isopropyl-6-(4-(2-(dimethylamino)ethylaminomethylcarbonylamino) benzyl)pyrazolo[3,4-d]pyrimidin-4-one;

dn) 1-(2,4,6-trichlorophenyl)-3-isopropyl-6-(4-(4-(aminomethyl)piperidin-1-ylmethylcarbonylamino) benzyl)pyrazolo[3,4-d]pyrimidin-4-one;

do) 1-(2,4,6-trichlorophenyl)-3-isopropyl-6-(4-(homopiperazin-1-ylmethylcarbonylamino)benzyl) pyrazolo[3,4-d]pyrimidin-4-one;

dp) 1-(2,4,6-trichlorophenyl)-3-isopropyl-6-(4-(ethylaminomethylcarbonylamino)benzyl)pyrazolo[3,4-d]pyrimidin-4-one;

dq) 1-(2,4,6-trichlorophenyl)-3-isopropyl-6-(4-(dimethylaminomethyl)-3-hydroxybenzyl)pyrazolo[3,4-d]pyrimidin-4-one;

dr) (S)-1-(2,4,6-trichlorophenyl)-3-isopropyl-6-(4-(N-methylprolinamido)benzyl)pyrazolo[3,4-d]pyrimidin-4-one;

ds) (+/−)-1-(2,4,6-trichlorophenyl)-3-isopropyl-6-(4-(N-,N-dimethylalaninamido)benzyl)pyrazolo[3,4-d] pyrimidin-4-one;

dt) 1-(2,4,6-trichlorophenyl)-3-isopropyl-6-(4-(1,4,7-triazacyclonon-1-ylmethylcarbonylamino)benzyl) pyrazolo[3,4-d]pyrimidin-4-one;

du) 1-(2,4,6-trichlorophenyl)-3-isopropyl-6-(3-amino-2-methylbenzyl)pyrazolo[3,4-d]pyrimidin-4-one;

dv) 1-(2,4,6-trichlorophenyl)-3-isopropyl-6-(4-(2-(morpholin-4-yl)ethylaminocarbonylamino)benzyl)pyrazolo[3,4-d]pyrimidin-4-one;

dw) 1-(2,4,6-trichlorophenyl)-3-isopropyl-6-(3-(N-,N-dimethylglycinamido)-2-methylbenzyl)pyrazolo[3,4-d]pyrimidin-4-one;

dx) 1-(2,4,6-trichlorophenyl)-3-isopropyl-6-(4-(4-methylpiperazin-1-ylaminocarbonylamino)benzyl)pyrazolo[3,4-d]pyrimidin-4-one;

dy) 1-(2,4,6-trichlorophenyl)-3-isopropyl-6-(4-(morpholin-4-ylaminocarbonylamino)benzyl)pyrazolo[3,4-d]pyrimidin-4-one;

dz) 1-(2,4,6-trichlorophenyl)-3-isopropyl-6-(4-(methoxyaminocarbonylamino)benzyl)pyrazolo[3,4-d]pyrimidin-4-one;

ea) 1-(2,4,6-trichlorophenyl)-3-isopropyl-6-(4-(methanesulfonamidocarbonylamino)benzyl)pyrazolo[3,4-d]pyrimidin-4-one;

eb) 1-(2,4,6-trichlorophenyl)-3-isopropyl-6-(4-(N-methyl,N-(2-(dimethylamino)ethyl)aminocarbonylamino)benzyl)pyrazolo[3,4-d]pyrimidin-4-one;

ec) 1-(2,4,6-trichlorophenyl)-3-isopropyl-6-(4-(N-methyl,N-(1-methylpiperidin-4-yl)aminocarbonylamino)benzyl)pyrazolo[3,4-d]pyrimidin-4-one;

ed) (+/−)-1-(2,4,6-trichlorophenyl)-3-isopropyl-6-(4-(tetrahydrofur-2-ylmethylaminocarbonylamino)benzyl)-pyrazolo[3,4-d]pyrimidin-4-one;

ee) (+/−)-1-(2,4,6-trichlorophenyl)-3-isopropyl-6-(4-(1-hydroxypent-2-ylaminocarbonylamino)benzyl)pyrazolo[3,4-d]pyrimidin-4-one;

ef) (+/−)-1-(2,4,6-trichlorophenyl)-3-isopropyl-6-(4-(1-hydroxyprop-2-ylaminocarbonylamino)benzyl)pyrazolo[3,4-d]pyrimidin-4-one;

eg) (+/−)-1-(2,4,6-trichlorophenyl)-3-isopropyl-6-(4-(2-hydroxyprop-1-ylaminocarbonylamino)benzyl)pyrazolo[3,4-d]pyrimidin-4-one;

eh) (+/−)-1-(2,4,6-trichlorophenyl)-3-isopropyl-6-(4-(2-(dimethylamino)prop-1-ylaminocarbonylamino)benzyl)pyrazolo[3,4-d]pyrimidin-4-one;

ei) 1-(2,4,6-trichlorophenyl)-3-cyclopropyl-6-(3-hydroxy-4-methoxybenzyl)pyrazolo[3,4-d]pyrimidin-4-one;

ej) 1-(2,4,6-trichlorophenyl)-3-cyclopropyl-6-(indazol-6-ylmethyl)pyrazolo[3,4-d]pyrimidin-4-one;

ek) 1-(2,4,6-trichlorophenyl)-3-cyclopropyl-6-(indazol-5-ylmethyl)pyrazolo[3,4-d]pyrimidin-4-one;

el) 1-(2,4,6-trichlorophenyl)-3-cyclopropyl-6-(indazol-4-ylmethyl)pyrazolo[3,4-d]pyrimidin-4-one;

em) 1-(2,4,6-trichlorophenyl)-3-cyclopropyl-6-(benzoxazol-2-on-5-ylmethyl)pyrazolo[3,4-d]pyrimidin-4-one;

en) 1-(2,4,6-trichlorophenyl)-3-cyclopropyl-6-(3-hydroxy-4-nitrobenzyl)pyrazolo[3,4-d]pyrimidin-4-one;

eo) 1-(2,4,6-trichlorophenyl)-3-cyclopropyl-6-(4-aminobenzyl)pyrazolo[3,4-d]pyrimidin-4-one;

ep) 1-(2,4,6-trichlorophenyl)-3-cyclopropyl-6-(4-(N,N-dimethylglycinamido)benzyl)pyrazolo[3,4-d]pyrimidin-4-one;

eq) 1-(2,4,6-trichlorophenyl)-3-isopropyl-6-(4-(cis-3,4-dimethylpiperazin-1-ylmethylcarbonylamino)benzyl)pyrazolo[3,4-d]pyrimidin-4-one;

er) 1-(2,4,6-trichlorophenyl)-3-isopropyl-6-(4-(trans-2,5-dimethylpiperazin-1-ylmethylcarbonylamino)benzyl)pyrazolo[3,4-d]pyrimidin-4-one;

es) 1-(2,4,6-trichlorophenyl)-3-isopropyl-6-(4-(3-methylpiperazin-1-ylmethylcarbonylamino)benzyl)pyrazolo[3,4-d]pyrimidin-4-one;

et) 1-(2,4,6-trichlorophenyl)-3-isopropyl-6-(5-(dimethylaminomethyl)-1-methylpyrrol-2-yl)pyrazolo[3,4-d]pyrimidin-4-one;

eu) 1-(2,4,6-trichlorophenyl)-3-isopropyl-6-(4-(4-methylpiperazin-1-ylaminocarbony)benzyl)pyrazolo[3,4-d]pyrimidin-4-one;

ev) 1-(2,4,6-trichlorophenyl)-3-isopropyl-6-(3-(N-methyl, N-(2-(dimethylamino)ethyl)aminocarbonylamino)benzyl)pyrazolo[3,4-d]pyrimidin-4-one;

ew) 1-(2-chloro-6-methylphenyl)-3-isopropyl-6-(4-(N-methyl,N-(1-methylpiperidin-4-yl)aminocarbonylamino)benzyl)pyrazolo[3,4-d]pyrimidin-4-one;

ex) 1-(2-chloro-6-methylphenyl)-3-isopropyl-6-(4-(N-methyl-N-(1-methylpiperidin-4-yl)aminomethylcarbonylamino)benzyl)pyrazolo[3,4-d]pyrimidin-4-one;

ey) 1-(2,4,6-trichlorophenyl)-3-ethyl-6-(4-(N-methyl,N-((3S,4S)-4-dimethylaminotetrahydrofur-3-yl)aminocarbonylamino)benzyl)pyrazolo[3,4-d]pyrimidin-4-one;

ez) 1-(2,4,6-trichlorophenyl)-3-isopropyl-6-(3-(N-methyl, N-(2-(dimethylamino)ethyl)aminocarbonyl)benzyl)pyrazolo[3,4-d]pyrimidin-4-one;

fa) 1-(2,4,6-trichlorophenyl)-3-isopropyl-6-(4-(2-pyrrolidin-1-ylethylaminocarbonyamino)benzyl)pyrazolo[3,4-]pyrimidin-4-one;

fb) 1-(2,6-dichlorophenyl)-3-isopropyl-6-(4-(N-methyl,N-(2-(dimethylamino)ethyl)aminocarbonymethyl)benzyl)pyrazolo[3,4-d]pyrimidin-4-one;

fc) 1-(2,6-dichlorophenyl)-3-isopropyl-6-(4-(N-(2-(dimethylamino)ethyl)aminocarbonymethyl)benzyl)pyrazolo[3,4-d]pyrimidin-4-one;

fd) 1-(2,4,6-trichlorophenyl)-3-isopropyl-6-(4-(N-(2-(dimethylamino)ethyl)aminocarbonyl)benzyl)pyrazolo[3,4-d]pyrimidin-4-one;

fe) 1-(2,4,6-trichlorophenyl)-3-isopropyl-6-(4-(methylamino)benzyl)pyrazolo[3,4-d]pyrimidin-4-one;

ff) 1-(2,4,6-trichlorophenyl)-3-isopropyl-6-(4-(N-methyl-N-(1-methylpiperidin-4-yl)aminocarbonylamino)benzyl)pyrazolo[3,4-d]pyrimidin-4-one;

fg) 1-(2,4,6-trichlorophenyl)-3-isopropyl-6-(4-(N-methyl, N-(2-(dimethylamino)ethyl)aminocarbonylamino)benzyl)pyrazolo[3,4-d]pyrimidin-4-one;

fh) 1-(2,6-dichloro-4-sulfonamidophenyl)-3-isopropyl-6-(3-methoxybenzyl)pyrazolo[3,4-d]pyrimidin-4-one; and fi) 1-(4-aminomethyl-2,6-dichlorophenyl)-3-isopropyl-6-(3-methoxybenzyl)pyrazolo[3,4-d]pyrimidin-4-one.

6. A pharmaceutical composition, comprising: a pharmaceutically acceptable carrier in combination with a therapeutically effective amount of a compound of any one of claims 1, 2, 3, 4, or 5.

7. A method of inhibiting cyclin dependent kinase enzymatic activity in a patient, comprising: administering to the patient in need of such treatment a therapeutically effective amount of a compound of any one of claims 1, 2, 3, 4, or 5, or a pharmaceutically acceptable salt form thereof.

8. A method of treating cancer or other proliferative diseases, comprising: administering to a host in need of such treatment a therapeutically effective amount of:

(a) a compound of claim 1, or a pharmaceutically acceptable salt form thereof; and, (b) at least one compound selected from the group consisting of anti-cancer agents and anti-proliferative agents.

\* \* \* \* \*